US009945860B2

(12) United States Patent
Yang et al.

(10) Patent No.: US 9,945,860 B2
(45) Date of Patent: Apr. 17, 2018

(54) NICOTINAMIDE ADENINE DINUCLEOTIDE INDICATORS, METHODS OF PREPARATION AND APPLICATION THEREOF

(71) Applicant: East China University of Science and Technology, Shanghai (CN)

(72) Inventors: Yi Yang, Shanghai (CN); Yuzheng Zhao, Shanghai (CN); Jing Jin, Shanghai (CN); Qingxun Hu, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 15/426,621

(22) Filed: Feb. 7, 2017

(65) Prior Publication Data

US 2017/0219584 A1 Aug. 3, 2017

Related U.S. Application Data

(62) Division of application No. 14/347,575, filed as application No. PCT/CN2012/081977 on Sep. 26, 2012, now Pat. No. 9,606,121.

(30) Foreign Application Priority Data

Sep. 26, 2011 (CN) .......................... 2011 1 0288807

(51) Int. Cl.
*C07K 14/32* (2006.01)
*G01N 33/573* (2006.01)
*G01N 33/58* (2006.01)
*G01N 33/50* (2006.01)

(52) U.S. Cl.
CPC ......... *G01N 33/5735* (2013.01); *C07K 14/32* (2013.01); *G01N 33/5011* (2013.01); *G01N 33/582* (2013.01)

(58) Field of Classification Search
None
See application file for complete search history.

(56) References Cited

U.S. PATENT DOCUMENTS 6,469,154 B1 10/2002 Tsien et al.

FOREIGN PATENT DOCUMENTS

CN 1821751 8/2006

OTHER PUBLICATIONS

Wang, et al., "Structure and functional properties of the Bacillus subtilis transcriptional repressor Rex," Molecular Microbiology, vol. 69, issue 2, Jun. 2008, pp. 466-478.

Office Action in related Chinese application Serial No. 201110288807.6 dated Aug. 22, 2016 (English translation attached).

Office Action in related Chinese application Serial No. 201410499267.X dated Aug. 22, 2016 (English translation).

Office Action in related Chinese application Serial No. 201410499305.1 dated Oct. 31, 2016, 7 pages. (English translation attached).

McLaughlin, et al., "Structural Basis for NADH/NAD+ Redox Sensing by a Rex Family Repressor," Molecular Cell, vol. 38, pp. 563-575, May 2010.

Rich, et. al., "The molecular machinery of Keilin's Respiratory Chain", Biochem Soc Trans. 2003, vol. 31, issue 6, pp. 1095-1105.

Belenky, et. al., "NAD+ metabolism in health and disease" Trends in Biochemical Sciences, Dec. 11, 2006, vol. 32, issue 1, pp. 12-19.

Sauve, et. al., "NAD+ and Vitamin B3: From Metabolism to Therapies"; J Pharmacol Exp Ther. 2008, vol. 324, issue 3, pp. 883-893.

Lin, et. al., "Nicotinamide adenine dinucleotide, a metabolic regulator of transcription, longevity and disease" Current Opinion in Cell Biology, 2003, vol. 15, issue 2, pp. 241-246.

Zhang, et. al., "Regulation of Corepressor Function by Nuclear NADH", Science, 2002, vol. 295, issue 5561, pp. 1895-1897.

Heim, et. al., "Wavelength mutations and posttranslational autoxidation of green fluorescent protein", Proc Natl Acad Sci U S A., 1994, vol. 91, issue 26, pp. 12501-12504.

Nagai, et. al., "Circularly permuted green fluorescent proteins engineered to sense CA2+", Proc Natl Acad Sci U.S.A., 2001, vol. 98, issue 6, pp. 3197-3202.

Brekasis, et. al., "A novel sensor of NADH/NAD+ redox poise in Streptomyces coelicolor A3(2)", EMBO J., 2003, vol. 22, issue 18, pp. 4856-4865.

Wang, et. al., "Structure and functional properties of the Bacillus subtilis transcriptional repressor Rex" Mol Microbiol, 2008, vol. 69, issue 2, pp. 466-478.

Mei, et. al., "Quantitative detection of NADH by in vitro bacterial luciferase bioluminescent, Acta Microbiologica Sinica", 2009, vol. 49, issue 9, pp. 1223-1228 (A) (English translation of Abstract attached).

(Continued)

*Primary Examiner* — Suzanne M Noakes
(74) *Attorney, Agent, or Firm* — Hovey Williams LLP

(57) ABSTRACT

The invention relates to a genetically encoded fluorescent sensor for nicotinamide adenine dinucleotide, as well as methods of preparation and uses thereof. In one aspect, this invention relates to a sensor for detecting nicotinamide adenine dinucleotide, particularly, a recombinant fluorescent fusion protein sensor for detecting nicotinamide adenine dinucleotide. In one specific aspect, this invention relates to a recombinant fluorescent fusion protein sensor for detecting reduced nicotinamide adenine dinucleotide (NADH); in another specific aspect, this invention relates to a recombinant fluorescent fusion protein sensor for detecting oxidized nicotinamide adenine dinucleotide ($NAD^+$); in yet another aspect, the invention relates to a recombinant fluorescent fusion protein sensor for detecting the ratio of reduced to oxidized nicotinamide adenine dinucleotide. This invention also relates to the method of preparing the sensors, and uses of the sensors in detecting NADH, $NAD^+$, $NADH/NAD^+$ ratio, screening drugs and measuring NADH metabolism.

21 Claims, 9 Drawing Sheets

(56) References Cited

OTHER PUBLICATIONS

Liu, et. al., "Determinaton of Human Red Blood Cells' NADH by Enzyme Cycling Fluorimetry", Chinese Journal of Spectroscopy Laboratory, 2010, vol. 27, issue 2), pp. 602-605 (English translation of Abstract attached).

International Preliminary Report on Patentability in corresponding PCT/CN2012/081977 dated Apr. 1, 2014 (English Translation) (10 pages).

Jin, "A novel fluorescent sensor for nicotinamide adenine dinucleotide", Fulltext Database of Selected Chinese M.Sc. Thesis, Fundamental Sciences, May 15, 2012 (dissertation in Chinese with Abstract in English on pp. 3-4),138 pages.

Office Action dated Nov. 12, 2012 in corresponding Chinese application Serial No. 201110288807.6 (7 pages) and Brief English Translation (3 pages).

Office Action dated Apr. 23, 2013 in corresponding Chinese application Serial No. 201110288807.6 (6 pages) and Brief English Translation (1 page).

Decision on Rejection dated Sep. 2, 2013 in corresponding Chinese application Serial No. 201110288807.6 (4 pages) and Brief English Translation (1 page1).

Office Action dated Jul. 14, 2014 in corresponding Chinese application Serial No. 201110288807.6 (3 pages) and Brief English Translation (1 page).

Yu, el al. "Two-Photon Autofluorescence Dynamics Imaging Reveals Sensitivity of Intracellular NADH Concentration and Conformation to Cell Physiology at the Single-Cell Level", J. Photochem. Photobiol. B., Apr. 2, 2009 (30 pages).

Zhao, et. al. "Genetically Encloded Fluorescent Sensors for Intracellular NADH Detection", Cell Metabolism, Oct. 5, 2011, pp. 555-566.

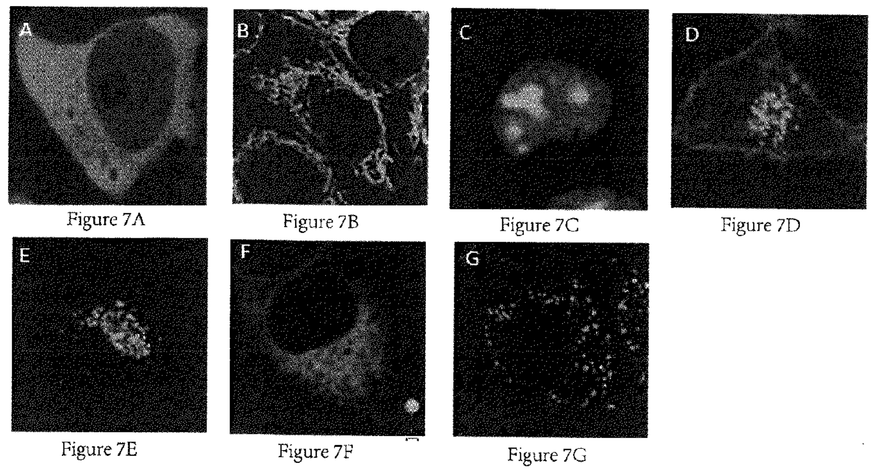
Figure 7A Figure 7B Figure 7C Figure 7D
Figure 7E Figure 7F Figure 7G
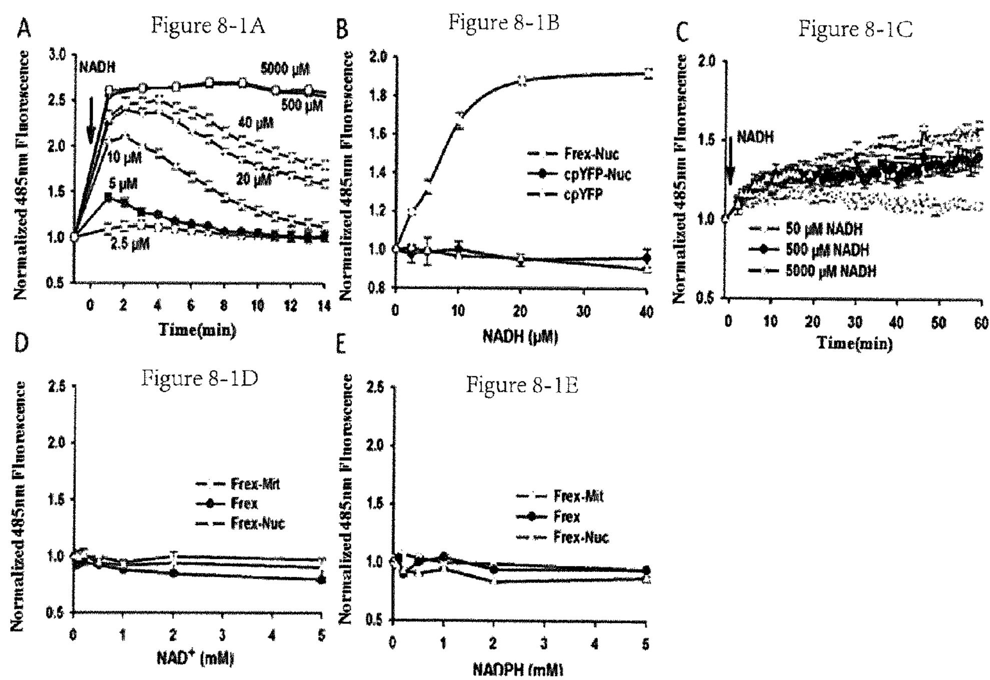

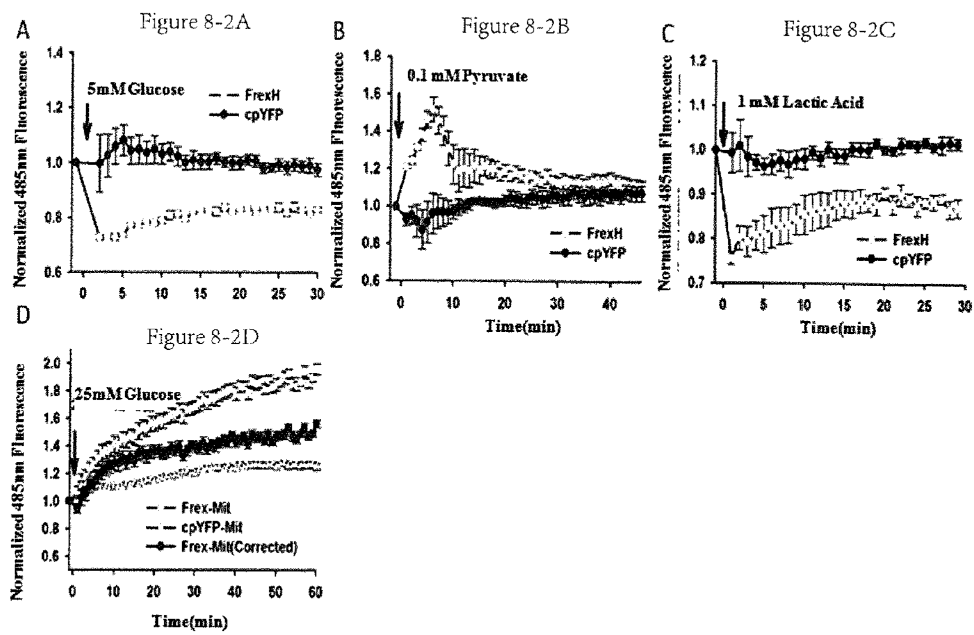
A
Figure 8-2A
5mM Glucose
FrexH
cpYFP
Normalized 485nm Fluorescence
B
Figure 8-2B
0.1 mM Pyruvate
FrexH
cpYFP
Time(min)
C
Figure 8-2C
1 mM Lactic Acid
FrexH
cpYFP
Time(min)
D
Figure 8-2D
25mM Glucose
Frex-Mit
cpYFP-Mit
Frex-Mit(Corrected)
Time(min)
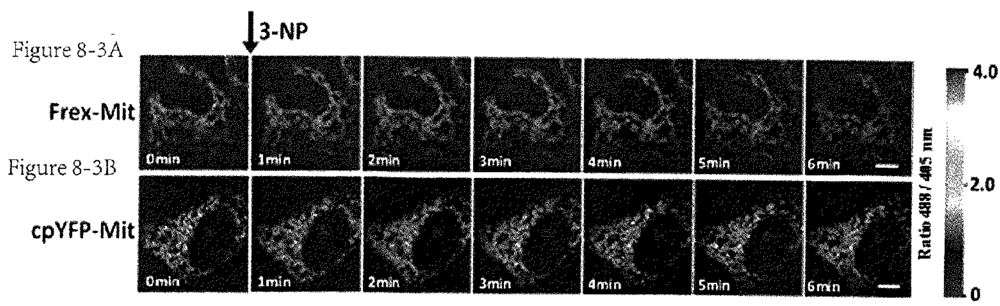
3-NP
Figure 8-3A
Frex-Mit
Figure 8-3B
cpYFP-Mit
0min
1min
2min
3min
4min
5min
6min
Ratio 488 / 485 nm
4.0
2.0
0
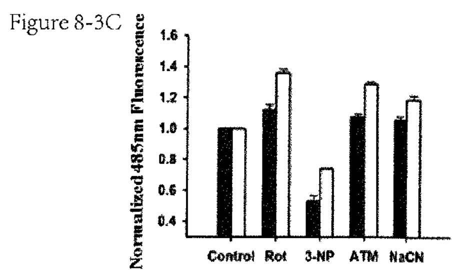
Figure 8-3C
Normalized 485nm Fluorescence
Control
Rot
3-NP
ATM
NaCN

SEQUENCE LISTING

<160> NUMBER OF SEQ ID NOS: 159

<210> SEQ ID NO 1
<211> LENGTH: 636
<212> TYPE: DNA
<213> ORGANISM: Thermus aquaticus

<400> SEQUENCE: 1
atgaaggtcc ccgaagcggc catcagccgc ctgatcacct acctccgcat cttggaggag 60
ctggaggccc agggggttca ccggacgagc tccgagcagc ttggggagct cgcccaggtc 120
acggccttcc aggtgcggaa ggacctttcc tacttcggct cctacgggac gcgcggggtg 180
gggtacaccg tccccgtcct gaagcgggag ctccgccaca tcctggggct caaccgcaag 240
tggggcctgt gcatcgtggg catgggccgg ctcgggagcg ccctggccga ctacccgggg 300
ttcggggaga gctttgagct taggggcttc tttgacgtgg acccggagaa ggtgggccgc 360
ccggtgcggg gcggggtcat tgagcacgtg gacctcctgc cccagcgggt tcccggccgc 420
attgagatcg ccctcctcac cgtgccccgg gaagcggccc agaaggcggc ggacctgttg 480
gtggcggcgg ggatcaaggg gatcctgaac ttcgccccgg tggtcctcga ggtgcccaag 540
gaggtggcgg tggagaacgt ggacttcttg gcggggctca cgcggctttc tttcgctatc 600
ctgaacccca agtggcggga agagatgatg gggtga 636

<210> SEQ ID NO 2
<211> LENGTH: 777
<212> TYPE: DNA
<213> ORGANISM: Streptomyces coelicolor A3(2)

<400> SEQUENCE: 2
atggcaactg gccgagcaca ccgaccggcg acccgcagcc gagggattcc cgaggccacc 60
gtcgccaggc ttccgctgta cctccgcgca ctgaccgcgc tgtccgagcg ctcggtgccc 120
acggtctcct ccgaggagct ggcggccgcc gcgggggtca actccgcgaa gctgcgcaag 180
gacttctcct acctcggctc ctacgggacc cgcggtgtcg gctacgacgt cgagtatctc 240
gtctaccaga tctcgcgcga actcggcctc acccaggact ggccggttgt gatcgtcggt 300
atcggcaacc tcggtgccgc gctcgccaac tacggtggtt tcgcctcccg cgggttccgc 360
gtcgccgcgc tcatcgacgc cgatccggga atggccggaa agcccgtcgc cggcatcccg 420
gtgcagcaca ccgacgagct ggagaagatc atccaggacg acggtgtctc gatcggtgtg 480
atcgcgaccc ccgccggcgc cgcccagcag gtctgcgacc gcctcgtggc cgccggtgtc 540

```
acctccatcc tgaacttcgc gccgaccgtg ctgaacgtcc ccgagggcgt cgacgtgcgc    600

aaggtcgacc tctccatcga gctgcagatc ctcgccttcc acgagcagcg caaggcgggc    660

gaggaggccg cggccgacgg cgccgcaccg cccgtcgccg cccgcaagca gcagcgctcc    720

accggctccg ccgaccaggg acccgacggg gacgtacccg ccgtgatgcc ggcatga       777


<210> SEQ ID NO 3
<211> LENGTH: 648
<212> TYPE: DNA
<213> ORGANISM: Bacillus subtilis strain 168

<400> SEQUENCE: 3

atgaataagg atcaatcaaa aattccgcag gcgacggcga aacggctgcc gctttactat     60

cgctttttaa agaatctgca tgcgtcagga aaacagcgtg tatcatccgc tgaactcagt    120

gatgccgtaa aggttgattc tgccacgatt cggagggatt tttcctattt tggagctctt    180

ggcaaaaaag gatacggata taatgtggat tatttgctgt ctttttttccg gaaaacgctt   240

gatcaggatg agatgacaga cgtcatcttg attggtgtcg ggaacttggg aacggcattt    300

cttcactata atttcacaaa aaacaataac acaaaaattt ctatggcttt tgatataaat    360

gagagtaaaa taggaactga ggtaggcggc gtgcccgtct ataaccttga tgaccttgaa    420

caacacgtaa aagatgaatc agttgccatt cttacagtgc cagcagttgc cgctcaatcc    480

attacagaca gattggtcgc attaggaatc aagggaatcc ttaattttac gccggcccgt    540

ttgaatgtgc cggaacacat tcgaattcat catatagatt tagcagttga gcttcagtca    600

ctggtttatt ttttgaagca ttattcagtt ttagaggaaa tcgaatag                 648


<210> SEQ ID NO 4
<211> LENGTH: 629
<212> TYPE: PRT
<213> ORGANISM: artificial sequence
<220> FEATURE:
<223> OTHER INFORMATION: synthetic fluorescent sensor

<400> SEQUENCE: 4

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160
```

```
Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Ser Tyr Asn Ser Asp Asn Val
                245                 250                 255

Tyr Ile Met Ala Asp Lys Gln Lys Asn Gly Ile Lys Ala Asn Phe Lys
            260                 265                 270

Ile Arg His Asn Val Glu Asp Gly Ser Val Gln Leu Ala Asp His Tyr
        275                 280                 285

Gln Gln Asn Thr Pro Ile Gly Asp Gly Pro Val Leu Leu Pro Asp Asn
    290                 295                 300

His Tyr Leu Ser Phe Gln Ser Val Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Asn Val Asp Gly Gly Ser Gly Gly Thr
            340                 345                 350

Gly Ser Lys Gly Glu Glu Leu Phe Thr Gly Val Val Pro Ile Leu Val
        355                 360                 365

Glu Leu Asp Gly Asp Val Asn Gly His Lys Phe Ser Val Ser Gly Glu
    370                 375                 380

Gly Glu Gly Asp Ala Thr Tyr Gly Lys Leu Thr Leu Lys Leu Ile Cys
385                 390                 395                 400

Thr Thr Gly Lys Leu Pro Val Pro Trp Pro Thr Leu Val Thr Thr Leu
                405                 410                 415

Gly Tyr Gly Leu Lys Cys Phe Ala Arg Tyr Pro Asp His Met Lys Gln
            420                 425                 430

His Asp Phe Phe Lys Ser Ala Met Pro Glu Gly Tyr Val Gln Glu Arg
        435                 440                 445

Thr Ile Phe Phe Lys Asp Asp Gly Asn Tyr Lys Thr Arg Ala Glu Val
    450                 455                 460

Lys Phe Glu Gly Asp Thr Leu Val Asn Arg Ile Glu Leu Lys Gly Ile
465                 470                 475                 480

Gly Phe Lys Glu Asp Gly Asn Ile Leu Gly His Lys Leu Glu Tyr Asn
                485                 490                 495

Gly Thr Met Thr Asp Val Ile Leu Ile Gly Val Gly Asn Leu Gly Thr
            500                 505                 510

Ala Phe Leu His Tyr Asn Phe Thr Lys Asn Asn Asn Thr Lys Ile Ser
        515                 520                 525

Met Ala Phe Asp Ile Asn Glu Ser Lys Ile Gly Thr Glu Val Gly Gly
    530                 535                 540

Val Pro Val Tyr Asn Leu Asp Asp Leu Glu Gln His Val Lys Asp Glu
545                 550                 555                 560

Ser Val Ala Ile Leu Thr Val Pro Ala Val Ala Ala Gln Ser Ile Thr
                565                 570                 575

Asp Arg Leu Val Ala Leu Gly Ile Lys Gly Ile Leu Asn Phe Thr Pro
```

```
            580                 585                 590

Ala Arg Leu Asn Val Pro Glu His Ile Arg Ile His His Ile Asp Leu
        595                 600                 605

Ala Val Glu Leu Gln Ser Leu Val Tyr Phe Leu Lys His Tyr Ser Val
    610                 615                 620

Leu Glu Glu Ile Glu
625


<210> SEQ ID NO 5
<211> LENGTH: 897
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 5

Met Asn Lys Asp Gln Ser Lys Ile Pro Gln Ala Thr Ala Lys Arg Leu
1               5                   10                  15

Pro Leu Tyr Tyr Arg Phe Leu Lys Asn Leu His Ala Ser Gly Lys Gln
            20                  25                  30

Arg Val Ser Ser Ala Glu Leu Ser Asp Ala Val Lys Val Asp Ser Ala
        35                  40                  45

Thr Ile Arg Arg Asp Phe Ser Tyr Phe Gly Ala Leu Gly Lys Lys Gly
    50                  55                  60

Tyr Gly Tyr Asn Val Asp Tyr Leu Leu Ser Phe Phe Arg Lys Thr Leu
65                  70                  75                  80

Asp Gln Asp Glu Met Thr Asp Val Ile Leu Ile Gly Val Gly Asn Leu
                85                  90                  95

Gly Thr Ala Phe Leu His Tyr Asn Phe Thr Lys Asn Asn Asn Thr Lys
            100                 105                 110

Ile Ser Met Ala Phe Asp Ile Asn Glu Ser Lys Ile Gly Thr Glu Val
        115                 120                 125

Gly Gly Val Pro Val Tyr Asn Leu Asp Asp Leu Glu Gln His Val Lys
    130                 135                 140

Asp Glu Ser Val Ala Ile Leu Thr Val Pro Ala Val Ala Ala Gln Ser
145                 150                 155                 160

Ile Thr Asp Arg Leu Val Ala Leu Gly Ile Lys Gly Ile Leu Asn Phe
                165                 170                 175

Thr Pro Ala Arg Leu Asn Val Pro Glu His Ile Arg Ile His His Ile
            180                 185                 190

Asp Leu Ala Val Glu Leu Gln Ser Leu Val Tyr Phe Leu Lys His Tyr
        195                 200                 205

Ser Val Leu Glu Glu Ile Glu Thr Ser Tyr Asn Ser Asp Asn Val Tyr
    210                 215                 220

Ile Met Ala Asp Lys Gln Lys Asn Gly Ile Lys Ala Asn Phe Lys Ile
225                 230                 235                 240

Arg His Asn Val Glu Asp Gly Ser Val Gln Leu Ala Asp His Tyr Gln
                245                 250                 255

Gln Asn Thr Pro Ile Gly Asp Gly Pro Val Leu Leu Pro Asp Asn His
            260                 265                 270

Tyr Leu Ser Phe Gln Ser Val Leu Ser Lys Asp Pro Asn Glu Lys Arg
        275                 280                 285

Asp His Met Val Leu Leu Glu Phe Val Thr Ala Ala Gly Ile Thr Leu
    290                 295                 300
```

```
Gly Met Asp Glu Leu Tyr Asn Val Asp Gly Gly Ser Gly Gly Thr Gly
305                 310                 315                 320

Ser Lys Gly Glu Glu Leu Phe Thr Gly Val Val Pro Ile Leu Val Glu
                325                 330                 335

Leu Asp Gly Asp Val Asn Gly His Lys Phe Ser Val Ser Gly Glu Gly
            340                 345                 350

Glu Gly Asp Ala Thr Tyr Gly Lys Leu Thr Leu Lys Leu Ile Cys Thr
        355                 360                 365

Thr Gly Lys Leu Pro Val Pro Trp Pro Thr Leu Val Thr Thr Leu Gly
    370                 375                 380

Tyr Gly Leu Lys Cys Phe Ala Arg Tyr Pro Asp His Met Lys Gln His
385                 390                 395                 400

Asp Phe Phe Lys Ser Ala Met Pro Glu Gly Tyr Val Gln Glu Arg Thr
                405                 410                 415

Ile Phe Phe Lys Asp Asp Gly Asn Tyr Lys Thr Arg Ala Glu Val Lys
            420                 425                 430

Phe Glu Gly Asp Thr Leu Val Asn Arg Ile Glu Leu Lys Gly Ile Gly
        435                 440                 445

Phe Lys Glu Asp Gly Asn Ile Leu Gly His Lys Leu Glu Tyr Asn Gly
    450                 455                 460

Thr Met Asn Lys Asp Gln Ser Lys Ile Pro Gln Ala Thr Ala Lys Arg
465                 470                 475                 480

Leu Pro Leu Tyr Tyr Arg Phe Leu Lys Asn Leu His Ala Ser Gly Lys
                485                 490                 495

Gln Arg Val Ser Ser Ala Glu Leu Ser Asp Ala Val Lys Val Asp Ser
            500                 505                 510

Ala Thr Ile Arg Arg Asp Phe Ser Tyr Phe Gly Ala Leu Gly Lys Lys
        515                 520                 525

Gly Tyr Gly Tyr Asn Val Asp Tyr Leu Leu Ser Phe Phe Arg Lys Thr
    530                 535                 540

Leu Asp Gln Asp Glu Met Thr Asp Val Ile Leu Ile Gly Val Gly Asn
545                 550                 555                 560

Leu Gly Thr Ala Phe Leu His Tyr Asn Phe Thr Lys Asn Asn Asn Thr
                565                 570                 575

Lys Ile Ser Met Ala Phe Asp Ile Asn Glu Ser Lys Ile Gly Thr Glu
            580                 585                 590

Val Gly Gly Val Pro Val Tyr Asn Leu Asp Asp Leu Glu Gln His Val
        595                 600                 605

Lys Asp Glu Ser Val Ala Ile Leu Thr Val Pro Ala Val Ala Ala Gln
    610                 615                 620

Ser Ile Thr Asp Arg Leu Val Ala Leu Gly Ile Lys Gly Ile Leu Asn
625                 630                 635                 640

Phe Thr Pro Ala Arg Leu Asn Val Pro Glu His Ile Arg Ile His His
                645                 650                 655

Ile Asp Leu Ala Val Glu Leu Gln Ser Leu Val Tyr Phe Leu Lys His
            660                 665                 670

Tyr Ser Val Leu Glu Glu Ile Glu Lys Leu Met Asn Lys Asp Gln Ser
        675                 680                 685

Lys Ile Pro Gln Ala Thr Ala Lys Arg Leu Pro Leu Tyr Tyr Arg Phe
    690                 695                 700

Leu Lys Asn Leu His Ala Ser Gly Lys Gln Arg Val Ser Ser Ala Glu
705                 710                 715                 720

Leu Ser Asp Ala Val Lys Val Asp Ser Ala Thr Ile Arg Arg Asp Phe
```

```
                725                 730                 735

Ser Tyr Phe Gly Ala Leu Gly Lys Lys Gly Tyr Gly Tyr Asn Val Asp
            740                 745                 750

Tyr Leu Leu Ser Phe Phe Arg Lys Thr Leu Asp Gln Asp Glu Met Thr
        755                 760                 765

Asp Val Ile Leu Ile Gly Val Gly Asn Leu Gly Thr Ala Phe Leu His
    770                 775                 780

Tyr Asn Phe Thr Lys Asn Asn Asn Thr Lys Ile Ser Met Ala Phe Asp
785                 790                 795                 800

Ile Asn Glu Ser Lys Ile Gly Thr Glu Val Gly Gly Val Pro Val Tyr
                805                 810                 815

Asn Leu Asp Asp Leu Glu Gln His Val Lys Asp Glu Ser Val Ala Ile
            820                 825                 830

Leu Thr Val Pro Ala Val Ala Ala Gln Ser Ile Thr Asp Arg Leu Val
        835                 840                 845

Ala Leu Gly Ile Lys Gly Ile Leu Asn Phe Thr Pro Ala Arg Leu Asn
    850                 855                 860

Val Pro Glu His Ile Arg Ile His His Ile Asp Leu Ala Val Glu Leu
865                 870                 875                 880

Gln Ser Leu Val Tyr Phe Leu Lys His Tyr Ser Val Leu Glu Glu Ile
                885                 890                 895

Glu


<210> SEQ ID NO 6
<211> LENGTH: 697
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
```

-continued

```
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Thr
225                 230                 235                 240

Ser Met Asn Lys Asp Gln Ser Lys Ile Pro Gln Ala Thr Ala Lys Arg
                245                 250                 255

Leu Pro Leu Tyr Tyr Arg Phe Leu Lys Asn Leu His Ala Ser Gly Lys
            260                 265                 270

Gln Arg Val Ser Ser Ala Glu Leu Ser Asp Ala Val Lys Val Asp Ser
        275                 280                 285

Ala Thr Ile Arg Arg Asp Phe Ser Tyr Phe Gly Ala Leu Gly Lys Lys
    290                 295                 300

Gly Tyr Gly Tyr Asn Val Asp Tyr Leu Leu Ser Phe Phe Arg Lys Thr
305                 310                 315                 320

Leu Asp Gln Asp Glu Met Thr Asp Val Ile Leu Ile Gly Val Gly Asn
                325                 330                 335

Leu Gly Thr Ala Phe Leu His Tyr Asn Phe Thr Lys Asn Asn Asn Thr
            340                 345                 350

Lys Ile Ser Met Ala Phe Asp Ile Asn Glu Ser Lys Ile Gly Thr Glu
        355                 360                 365

Val Gly Gly Val Pro Val Tyr Asn Leu Asp Asp Leu Glu Gln His Val
    370                 375                 380

Lys Asp Glu Ser Val Ala Ile Leu Thr Val Pro Ala Val Ala Ala Gln
385                 390                 395                 400

Ser Ile Thr Asp Arg Leu Val Ala Leu Gly Ile Lys Gly Ile Leu Asn
                405                 410                 415

Phe Thr Pro Ala Arg Leu Asn Val Pro Glu His Ile Arg Ile His His
            420                 425                 430

Ile Asp Leu Ala Val Glu Leu Gln Ser Leu Val Tyr Phe Leu Lys His
        435                 440                 445

Tyr Ser Val Leu Glu Glu Ile Glu Gly Thr Met Val Ser Lys Gly Glu
    450                 455                 460

Glu Leu Phe Thr Gly Val Val Pro Ile Leu Val Glu Leu Asp Gly Asp
465                 470                 475                 480

Val Asn Gly His Lys Phe Ser Val Ser Gly Glu Gly Glu Gly Asp Ala
                485                 490                 495

Thr Tyr Gly Lys Leu Thr Leu Lys Phe Ile Cys Thr Thr Gly Lys Leu
            500                 505                 510

Pro Val Pro Trp Pro Thr Leu Val Thr Thr Leu Thr Trp Gly Val Gln
        515                 520                 525

Cys Phe Ser Arg Tyr Pro Asp His Met Lys Gln His Asp Phe Phe Lys
    530                 535                 540

Ser Ala Met Pro Glu Gly Tyr Val Gln Glu Arg Thr Ile Phe Phe Lys
545                 550                 555                 560

Asp Asp Gly Asn Tyr Lys Thr Arg Ala Glu Val Lys Phe Glu Gly Asp
                565                 570                 575

Thr Leu Val Asn Arg Ile Glu Leu Lys Gly Ile Asp Phe Lys Glu Asp
            580                 585                 590

Gly Asn Ile Leu Gly His Lys Leu Glu Tyr Asn Tyr Ile Ser His Asn
        595                 600                 605
```

```
Val Tyr Ile Thr Ala Asp Lys Gln Lys Asn Gly Ile Lys Ala Asn Phe
    610                 615                 620

Lys Ile Arg His Asn Ile Glu Asp Gly Ser Val Gln Leu Ala Asp His
625                 630                 635                 640

Tyr Gln Gln Asn Thr Pro Ile Gly Asp Gly Pro Val Leu Leu Pro Asp
                645                 650                 655

Asn His Tyr Leu Ser Thr Gln Ser Ala Leu Ser Lys Asp Pro Asn Glu
            660                 665                 670

Lys Arg Asp His Met Val Leu Leu Glu Phe Val Thr Ala Ala Gly Ile
        675                 680                 685

Thr Leu Gly Met Asp Glu Leu Tyr Lys
    690                 695


<210> SEQ ID NO 7
<211> LENGTH: 463
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 7

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
```

```
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Gly Thr Gly Leu Ala Gly Leu Thr Arg Leu
        435                 440                 445

Ser Phe Ala Ile Leu Asn Pro Lys Trp Arg Glu Glu Met Met Gly
    450                 455                 460


<210> SEQ ID NO 8
<211> LENGTH: 680
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 8

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160
```

```
Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Gly Thr Gly Leu Ala Gly Leu Thr Arg Leu
        435                 440                 445

Ser Phe Ala Ile Leu Asn Pro Lys Trp Arg Glu Glu Met Met Gly Lys
    450                 455                 460

Leu Met Asn Lys Asp Gln Ser Lys Ile Pro Gln Ala Thr Ala Lys Arg
465                 470                 475                 480

Leu Pro Leu Tyr Tyr Arg Phe Leu Lys Asn Leu His Ala Ser Gly Lys
                485                 490                 495

Gln Arg Val Ser Ser Ala Glu Leu Ser Asp Ala Val Lys Val Asp Ser
            500                 505                 510

Ala Thr Ile Arg Arg Asp Phe Ser Tyr Phe Gly Ala Leu Gly Lys Lys
        515                 520                 525

Gly Tyr Gly Tyr Asn Val Asp Tyr Leu Leu Ser Phe Phe Arg Lys Thr
    530                 535                 540

Leu Asp Gln Asp Glu Met Thr Asp Val Ile Leu Ile Gly Val Gly Asn
545                 550                 555                 560

Leu Gly Thr Ala Phe Leu His Tyr Asn Phe Thr Lys Asn Asn Asn Thr
                565                 570                 575

Lys Ile Ser Met Ala Phe Asp Ile Asn Glu Ser Lys Ile Gly Thr Glu
```

```
            580                 585                 590

Val Gly Gly Val Pro Val Tyr Asn Leu Asp Asp Leu Glu Gln His Val
        595                 600                 605

Lys Asp Glu Ser Val Ala Ile Leu Thr Val Pro Ala Val Ala Ala Gln
    610                 615                 620

Ser Ile Thr Asp Arg Leu Val Ala Leu Gly Ile Lys Gly Ile Leu Asn
625                 630                 635                 640

Phe Thr Pro Ala Arg Leu Asn Val Pro Glu His Ile Arg Ile His His
                645                 650                 655

Ile Asp Leu Ala Val Glu Leu Gln Ser Leu Val Tyr Phe Leu Lys His
            660                 665                 670

Tyr Ser Val Leu Glu Glu Ile Glu
        675                 680


<210> SEQ ID NO 9
<211> LENGTH: 1890
<212> TYPE: DNA
<213> ORGANISM: artificial sequence
<220> FEATURE:
<223> OTHER INFORMATION: Synthetic polynucleotide

<400> SEQUENCE: 9

atgcggggtt ctcatcatca tcatcatcat ggtatggcta gcatgactgg tggacagcaa      60

atgggtcggg atctgtacga cgatgacgat aaggatccga tgaataagga tcaatcaaaa     120

attccgcagg cgacggcgaa acggctgccg ctttactatc gctttttaaa gaatctgcat     180

gcgtcaggaa aacagcgtgt atcatccgct gaactcagtg atgccgtaaa ggttgattct     240

gccacgattc ggagggattt ttcctatttt ggagctcttg gcaaaaaagg atacggatat     300

aatgtggatt atttgctgtc ttttttccgg aaaacgcttg atcaggatga gatgacagac     360

gtcatcttga ttggtgtcgg gaacttggga acggcatttc ttcactataa tttcacaaaa     420

aacaataaca caaaaatttc tatggctttt gatataaatg agagtaaaat aggaactgag     480

gtaggcggcg tgcccgtcta taaccttgat gaccttgaac aacacgtaaa agatgaatca     540

gttgccattc ttacagtgcc agcagttgcc gctcaatcca ttacagacag attggtcgca     600

ttaggaatca agggaatcct taattttacg ccggcccgtt tgaatgtgcc ggaacacatt     660

cgaattcatc atatagattt agcagttgag cttcagtcac tggtttattt tttgaagcat     720

tattcagttt tagaggaaat cgaaactagt tacaacagcg acaacgtcta tatcatggcc     780

gacaagcaga agaacggcat caaggccaac ttcaagatcc gccacaacgt cgaggacggc     840

agcgtgcagc tcgccgacca ctaccagcag aacaccccca tcggcgacgg ccccgtgctg     900

ctgcccgaca accactacct gagcttccag tccgtcctga gcaaagaccc caacgagaag     960

cgcgatcaca tggtcctgct ggagttcgtg accgccgccg ggatcactct cggcatggac    1020

gagctgtaca acgtggatgg cggtagcggt ggcaccggca gcaagggcga ggagctgttc    1080

accggggtgg tgcccatcct ggtcgagctg gacggcgacg taaacggcca caagttcagc    1140

gtgtccggcg agggcgaggg cgatgccacc tacggcaagc tgaccctgaa gctgatctgc    1200

accaccggca agctgcccgt gccctggccc accctcgtga ccaccctcgg ctacggcctg    1260

aagtgcttcg cccgctaccc cgaccacatg aagcagcacg acttcttcaa gtccgccatg    1320

cccgaaggct acgtccagga gcgcaccatc ttcttcaagg acgacggcaa ctacaagacc    1380

cgcgccgagg tgaagttcga gggcgacacc ctggtgaacc gcatcgagct gaagggcatc    1440

ggcttcaagg aggacggcaa catcctgggg cacaagctgg agtacaacgg taccatgaca    1500
```

```
gacgtcatct tgattggtgt cgggaacttg ggaacggcat ttcttcacta taatttcaca   1560

aaaaacaata acacaaaaat ttctatggct tttgatataa atgagagtaa aataggaact   1620

gaggtaggcg gcgtgcccgt ctataacctt gatgaccttg aacaacacgt aaaagatgaa   1680

tcagttgcca ttcttacagt gccagcagtt gccgctcaat ccattacaga cagattggtc   1740

gcattaggaa tcaagggaat ccttaatttt acgccggccc gtttgaatgt gccggaacac   1800

attcgaattc atcatataga tttagcagtt gagcttcagt cactggttta tttttgaag   1860

cattattcag ttttagagga aatcgaatag                                    1890
```

<210> SEQ ID NO 10
<211> LENGTH: 2694
<212> TYPE: DNA
<213> ORGANISM: artificial sequence
<220> FEATURE:
<223> OTHER INFORMATION: Synthetic nucleotide sequence encoding for Frex

<400> SEQUENCE: 10

```
atgaataagg atcaatcaaa aattccgcag gcgacggcga aacggctgcc gctttactat     60

cgctttttaa agaatctgca tgcgtcagga aaacagcgtg tatcatccgc tgaactcagt    120

gatgccgtaa aggttgattc tgccacgatt cggagggatt tttcctattt tggagctctt    180

ggcaaaaaag gatacggata taatgtggat tatttgctgt ctttttttccg gaaaacgctt    240

gatcaggatg agatgacaga cgtcatcttg attggtgtcg ggaacttggg aacggcattt    300

cttcactata atttcacaaa aaacaataac acaaaaattt ctatggcttt tgatataaat    360

gagagtaaaa taggaactga ggtaggcggc gtgcccgtct ataaccttga tgaccttgaa    420

caacacgtaa aagatgaatc agttgccatt cttacagtgc cagcagttgc cgctcaatcc    480

attacagaca gattggtcgc attaggaatc aagggaatcc ttaattttac gccggcccgt    540

ttgaatgtgc cggaacacat tcgaattcat catatagatt tagcagttga gcttcagtca    600

ctggtttatt ttttgaagca ttattcagtt ttagaggaaa tcgaaactag ttacaacagc    660

gacaacgtct atatcatggc cgacaagcag aagaacggca tcaaggccaa cttcaagatc    720

cgccacaacg tcgaggacgg cagcgtgcag ctcgccgacc actaccagca gaacaccccc    780

atcggcgacg gccccgtgct gctgcccgac aaccactacc tgagcttcca gtccgtcctg    840

agcaaagacc ccaacgagaa gcgcgatcac atggtcctgc tggagttcgt gaccgccgcc    900

gggatcactc tcggcatgga cgagctgtac aacgtggatg gcggtagcgg tggcaccggc    960

agcaagggcg aggagctgtt caccggggtg gtgcccatcc tggtcgagct ggacggcgac   1020

gtaaacggcc acaagttcag cgtgtccggc gagggcgagg gcgatgccac ctacggcaag   1080

ctgaccctga agctgatctg caccaccggc aagctgcccg tgccctggcc caccctcgtg   1140

accaccctcg gctacggcct gaagtgcttc gcccgctacc ccgaccacat gaagcagcac   1200

gacttcttca agtccgccat gcccgaaggc tacgtccagg agcgcaccat cttcttcaag   1260

gacgacggca actacaagac ccgcgccgag gtgaagttcg agggcgacac cctggtgaac   1320

cgcatcgagc tgaagggcat cggcttcaag gaggacggca acatcctggg gcacaagctg   1380

gagtacaacg gtaccatgaa taaggatcaa tcaaaaattc cgcaggcgac ggcgaaacgg   1440

ctgccgcttt actatcgctt tttaaagaat ctgcatgcgt caggaaaaca gcgtgtatca   1500

tccgctgaac tcagtgatgc cgtaaaggtt gattctgcca cgattcggag ggatttttcc   1560

tattttggag ctcttggcaa aaaaggatac ggatataatg tggattattt gctgtctttt   1620
```

```
ttccggaaaa cgcttgatca ggatgagatg acagacgtca tcttgattgg tgtcgggaac   1680

ttgggaacgg catttcttca ctataatttc acaaaaaaca ataacacaaa aatttctatg   1740

gcttttgata taaatgagag taaaatagga actgaggtag gcggcgtgcc cgtctataac   1800

cttgatgacc ttgaacaaca cgtaaaagat gaatcagttg ccattcttac agtgccagca   1860

gttgccgctc aatccattac agacagattg gtcgcattag gaatcaaggg aatccttaat   1920

tttacgccgg cccgtttgaa tgtgccggaa cacattcgaa ttcatcatat agatttagca   1980

gttgagcttc agtcactggt ttattttttg aagcattatt cagttttaga ggaaatcgaa   2040

aagcttatga ataaggatca atcaaaaatt ccgcaggcga cggcgaaacg gctgccgctt   2100

tactatcgct ttttaaagaa tctgcatgcg tcaggaaaac agcgtgtatc atccgctgaa   2160

ctcagtgatg ccgtaaaggt tgattctgcc acgattcgga gggatttttc ctattttgga   2220

gctcttggca aaaaaggata cggatataat gtggattatt tgctgtcttt tttccggaaa   2280

acgcttgatc aggatgagat gacagacgtc atcttgattg gtgtcgggaa cttgggaacg   2340

gcatttcttc actataattt cacaaaaaac aataacacaa aaatttctat ggcttttgat   2400

ataaatgaga gtaaaatagg aactgaggta ggcggcgtgc ccgtctataa ccttgatgac   2460

cttgaacaac acgtaaaaga tgaatcagtt gccattctta cagtgccagc agttgccgct   2520

caatccatta cagacagatt ggtcgcatta ggaatcaagg gaatccttaa ttttacgccg   2580

gcccgtttga atgtgccgga acacattcga attcatcata tagatttagc agttgagctt   2640

cagtcactgg tttatttttt gaagcattat tcagttttag aggaaatcga atag         2694
```

<210> SEQ ID NO 11
<211> LENGTH: 2094
<212> TYPE: DNA
<213> ORGANISM: artificial sequence
<220> FEATURE:
<223> OTHER INFORMATION: Synthetic nucleotide sequence encoding for Frex

<400> SEQUENCE: 11

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccttcggcta cggcctgatg tgcttcgccc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagct accagtccgc cctgagcaaa gaccccaacg agaagcgcga tcacatggtc    660

ctgctggagt tcgtgaccgc cgccgggatc actctcggca tggacgagct gtacaagact    720

agtatgaata aggatcaatc aaaaattccg caggcgacgg cgaaacggct gccgctttac    780

tatcgctttt taaagaatct gcatgcgtca ggaaaacagc gtgtatcatc cgctgaactc    840

agtgatgccg taaaggttga ttctgccacg attcggaggg atttttccta ttttggagct    900

cttggcaaaa aaggatacgg atataatgtg gattatttgc tgtctttttt ccggaaaacg    960

cttgatcagg atgagatgac agacgtcatc ttgattggtg tcgggaactt gggaacggca   1020
```

```
tttcttcact ataatttcac aaaaaacaat aacacaaaaa tttctatggc ttttgatata   1080
aatgagagta aaataggaac tgaggtaggc ggcgtgcccg tctataacct tgatgacctt   1140
gaacaacacg taaaagatga atcagttgcc attcttacag tgccagcagt tgccgctcaa   1200
tccattacag acagattggt cgcattagga atcaagggaa tccttaattt tacgccggcc   1260
cgtttgaatg tgccggaaca cattcgaatt catcatatag atttagcagt tgagcttcag   1320
tcactggttt attttttgaa gcattattca gttttagagg aaatcgaagg taccatggtg   1380
agcaagggcg aggagctgtt caccggggtg gtgcccatcc tggtcgagct ggacggcgac   1440
gtaaacggcc acaagttcag cgtgtccggc gagggcgagg gcgatgccac ctacggcaag   1500
ctgaccctga agttcatctg caccaccggc aagctgcccg tgccctggcc caccctcgtg   1560
accaccctga cctggggcgt gcagtgcttc agccgctacc ccgaccacat gaagcagcac   1620
gacttcttca agtccgccat gcccgaaggc tacgtccagg agcgcaccat cttcttcaag   1680
gacgacggca actacaagac ccgcgccgag gtgaagttcg agggcgacac cctggtgaac   1740
cgcatcgagc tgaagggcat cgacttcaag gaggacggca acatcctggg gcacaagctg   1800
gagtacaact acatcagcca caacgtctat atcaccgccg acaagcagaa gaacggcatc   1860
aaggccaact tcaagatccg ccacaacatc gaggacggca gcgtgcagct cgccgaccac   1920
taccagcaga acacccccat cggcgacggc cccgtgctgc tgcccgacaa ccactacctg   1980
agcacccagt ccgccctgag caaagacccc aacgagaagc gcgatcacat ggtcctgctg   2040
gagttcgtga ccgccgccgg gatcactctc ggcatggacg agctgtacaa gtaa         2094
```

<210> SEQ ID NO 12
<211> LENGTH: 1392
<212> TYPE: DNA
<213> ORGANISM: artificial sequence
<220> FEATURE:
<223> OTHER INFORMATION: Synthetic nucleotide sequence encoding for Frex

<400> SEQUENCE: 12

```
atgaaggtgc ccgaggccgc catcagccgg ctgatcacct acctgcggat tctggaggag     60
ctggaggccc agggcgtgca ccggaccagc agcgagcagc tgggcgagct ggcccaggtg    120
accgccttcc aggtgcggaa ggacctgagc tacttcggca gctacggcac ccggggcgtg    180
ggctacaccg tgcccgtgct gaagcgggag ctgcggcaca tcctgggcct gaaccggaag    240
tggggcctgt gcatcgtggg catgggccgg ctgggcagcg ccctggccga ctaccccggc    300
ttcggcgaga gcttcgagct gcggggcttc ttcgacgtcg accccgagaa ggtgggccgg    360
cccgtgcggg gcggcgtgat cgagcacgta gatctgctgc cccagcgggt gcccggccgg    420
atcgagatcg ccctgctgac cgtgccccgg gaggccgccc agaaggccgc cgacctgctg    480
gtggccgccg gcatcaaggg catcctgaac ttcgcaccgg tggtgctgga ggtgcccaag    540
gaggtggccg tggagaacgt ggacttctct gcaggctaca acagcgacaa cgtctatatc    600
atggccgaca agcagaagaa cggcatcaag gccaacttca agatccgcca caacgtcgag    660
gacggcagcg tgcagctcgc cgaccactac cagcagaaca cccccatcgg cgacggcccc    720
gtgctgctgc ccgacaacca ctacctgagc ttccagtccg tcctgagcaa agaccccaac    780
gagaagcgcg atcacatggt cctgctggag ttcgtgaccg ccgccgggat cactctcggc    840
atggacgagc tgtacaacgt ggatggcggt agcggtggca ccggcagcaa gggcgaggag    900
ctgttcaccg gggtggtgcc catcctggtc gagctggacg gcgacgtaaa cggccacaag    960
```

```
ttcagcgtgt ccggcgaggg cgagggcgat gccacctacg gcaagctgac cctgaagctg   1020

atctgcacca ccggcaagct gcccgtgccc tggcccaccc tcgtgaccac cctcggctac   1080

ggcctgaagt gcttcgcccg ctaccccgac cacatgaagc agcacgactt cttcaagtcc   1140

gccatgcccg aaggctacgt ccaggagcgc accatcttct tcaaggacga cggcaactac   1200

aagacccgcg ccgaggtgaa gttcgagggc gacaccctgg tgaaccgcat cgagctgaag   1260

ggcatcggct tcaaggagga cggcaacatc ctggggcaca agctggagta caacggtacc   1320

ggcctggccg gcctgacccg gctgagcttc gccatcctga accccaagtg gcgggaggag   1380

atgatgggct aa                                                       1392
```

```
<210> SEQ ID NO 13
<211> LENGTH: 2043
<212> TYPE: DNA
<213> ORGANISM: artificial sequence
<220> FEATURE:
<223> OTHER INFORMATION: Synthetic nucleotide sequence encoding for Frex

<400> SEQUENCE: 13

atgaaggtgc ccgaggccgc catcagccgg ctgatcacct acctgcggat tctggaggag     60

ctggaggccc agggcgtgca ccggaccagc agcgagcagc tgggcgagct ggcccaggtg    120

accgccttcc aggtgcggaa ggacctgagc tacttcggca gctacggcac ccggggcgtg    180

ggctacaccg tgcccgtgct gaagcgggag ctgcggcaca tcctgggcct gaaccggaag    240

tggggcctgt gcatcgtggg catgggccgg ctgggcagcg ccctggccga ctaccccggc    300

ttcggcgaga gcttcgagct gcggggcttc ttcgacgtcg accccgagaa ggtgggccgg    360

cccgtgcggg gcggcgtgat cgagcacgta gatctgctgc cccagcgggt gcccggccgg    420

atcgagatcg ccctgctgac cgtgccccgg gaggccgccc agaaggccgc cgacctgctg    480

gtggccgccg gcatcaaggg catcctgaac ttcgcaccgg tggtgctgga ggtgcccaag    540

gaggtggccg tggagaacgt ggacttctct gcaggctaca acagcgacaa cgtctatatc    600

atggccgaca agcagaagaa cggcatcaag gccaacttca agatccgcca caacgtcgag    660

gacggcagcg tgcagctcgc cgaccactac cagcagaaca cccccatcgg cgacggcccc    720

gtgctgctgc ccgacaacca ctacctgagc ttccagtccg tcctgagcaa agaccccaac    780

gagaagcgcg atcacatggt cctgctggag ttcgtgaccg ccgccgggat cactctcggc    840

atggacgagc tgtacaacgt ggatggcggt agcggtggca ccggcagcaa gggcgaggag    900

ctgttcaccg gggtggtgcc catcctggtc gagctggacg gcgacgtaaa cggccacaag    960

ttcagcgtgt ccggcgaggg cgagggcgat gccacctacg gcaagctgac cctgaagctg   1020

atctgcacca ccggcaagct gcccgtgccc tggcccaccc tcgtgaccac cctcggctac   1080

ggcctgaagt gcttcgcccg ctaccccgac cacatgaagc agcacgactt cttcaagtcc   1140

gccatgcccg aaggctacgt ccaggagcgc accatcttct tcaaggacga cggcaactac   1200

aagacccgcg ccgaggtgaa gttcgagggc gacaccctgg tgaaccgcat cgagctgaag   1260

ggcatcggct tcaaggagga cggcaacatc ctggggcaca agctggagta caacggtacc   1320

ggcctggccg gcctgacccg gctgagcttc gccatcctga accccaagtg gcgggaggag   1380

atgatgggca agcttatgaa taaggatcaa tcaaaaattc cgcaggcgac ggcgaaacgg   1440

ctgccgcttt actatcgctt tttaaagaat ctgcatgcgt caggaaaaca gcgtgtatca   1500

tccgctgaac tcagtgatgc cgtaaaggtt gattctgcca cgattcggag ggatttttcc   1560

tattttggag ctcttggcaa aaaaggatac ggatataatg tggattattt gctgtctttt   1620
```

```
ttccggaaaa cgcttgatca ggatgagatg acagacgtca tcttgattgg tgtcgggaac   1680

ttgggaacgg catttcttca ctataatttc acaaaaaaca ataacacaaa aatttctatg   1740

gcttttgata taaatgagag taaaatagga actgaggtag gcggcgtgcc cgtctataac   1800

cttgatgacc ttgaacaaca cgtaaaagat gaatcagttg ccattcttac agtgccagca   1860

gttgccgctc aatccattac agacagattg gtcgcattag gaatcaaggg aatccttaat   1920

tttacgccgg cccgtttgaa tgtgccggaa cacattcgaa ttcatcatat agatttagca   1980

gttgagcttc agtcactggt ttattttttg aagcattatt cagttttaga ggaaatcgaa   2040

taa                                                                 2043

<210> SEQ ID NO 14
<211> LENGTH: 84
<212> TYPE: PRT
<213> ORGANISM: Bacillus subtilis strain 168

<400> SEQUENCE: 14

Met Asn Lys Asp Gln Ser Lys Ile Pro Gln Ala Thr Ala Lys Arg Leu
1               5                   10                  15

Pro Leu Tyr Tyr Arg Phe Leu Lys Asn Leu His Ala Ser Gly Lys Gln
            20                  25                  30

Arg Val Ser Ser Ala Glu Leu Ser Asp Ala Val Lys Val Asp Ser Ala
        35                  40                  45

Thr Ile Arg Arg Asp Phe Ser Tyr Phe Gly Ala Leu Gly Lys Lys Gly
    50                  55                  60

Tyr Gly Tyr Asn Val Asp Tyr Leu Leu Ser Phe Phe Arg Lys Thr Leu
65                  70                  75                  80

Asp Gln Asp Glu


<210> SEQ ID NO 15
<211> LENGTH: 79
<212> TYPE: PRT
<213> ORGANISM: Thermus aquaticus

<400> SEQUENCE: 15

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg
65                  70                  75


<210> SEQ ID NO 16
<211> LENGTH: 110
<212> TYPE: PRT
<213> ORGANISM: Bacillus subtilis strain 168

<400> SEQUENCE: 16

Met Thr Asp Val Ile Leu Ile Gly Val Gly Asn Leu Gly Thr Ala Phe
1               5                   10                  15

Leu His Tyr Asn Phe Thr Lys Asn Asn Asn Thr Lys Ile Ser Met Ala
            20                  25                  30
```

```
Phe Asp Ile Asn Glu Ser Lys Ile Gly Thr Glu Val Gly Gly Val Pro
        35                  40                  45

Val Tyr Asn Leu Asp Asp Leu Glu Gln His Val Lys Asp Glu Ser Val
    50                  55                  60

Ala Ile Leu Thr Val Pro Ala Val Ala Ala Gln Ser Ile Thr Asp Arg
65                  70                  75                  80

Leu Val Ala Leu Gly Ile Lys Gly Ile Leu Asn Phe Thr Pro Ala Arg
                85                  90                  95

Leu Asn Val Pro Glu His Ile Arg Ile His His Ile Asp Leu
            100                 105                 110


<210> SEQ ID NO 17
<211> LENGTH: 110
<212> TYPE: PRT
<213> ORGANISM: Thermus aquaticus

<400> SEQUENCE: 17

Lys Trp Gly Leu Cys Ile Val Gly Met Gly Arg Leu Gly Ser Ala Leu
1               5                   10                  15

Ala Asp Tyr Pro Gly Phe Gly Glu Ser Phe Glu Leu Arg Gly Phe Phe
            20                  25                  30

Asp Val Asp Pro Glu Lys Val Gly Arg Pro Val Arg Gly Gly Val Ile
        35                  40                  45

Glu His Val Asp Leu Leu Pro Gln Arg Val Pro Gly Arg Ile Glu Ile
    50                  55                  60

Ala Leu Leu Thr Val Pro Arg Glu Ala Ala Gln Lys Ala Ala Asp Leu
65                  70                  75                  80

Leu Val Ala Ala Gly Ile Lys Gly Ile Leu Asn Phe Ala Pro Val Val
                85                  90                  95

Leu Glu Val Pro Lys Glu Val Ala Val Glu Asn Val Asp Phe
            100                 105                 110


<210> SEQ ID NO 18
<211> LENGTH: 96
<212> TYPE: PRT
<213> ORGANISM: Bacillus subtilis strain 168

<400> SEQUENCE: 18

Asn Glu Ser Lys Ile Gly Thr Glu Val Gly Gly Val Pro Val Tyr Asn
1               5                   10                  15

Leu Asp Asp Leu Glu Gln His Val Lys Asp Glu Ser Val Ala Ile Leu
            20                  25                  30

Thr Val Pro Ala Val Ala Ala Gln Ser Ile Thr Asp Arg Leu Val Ala
        35                  40                  45

Leu Gly Ile Lys Gly Ile Leu Asn Phe Thr Pro Ala Arg Leu Asn Val
    50                  55                  60

Pro Glu His Ile Arg Ile His His Ile Asp Leu Ala Val Glu Leu Gln
65                  70                  75                  80

Ser Leu Val Tyr Phe Leu Lys His Tyr Ser Val Leu Glu Glu Ile Glu
                85                  90                  95


<210> SEQ ID NO 19
<211> LENGTH: 98
<212> TYPE: PRT
<213> ORGANISM: Thermus aquaticus

<400> SEQUENCE: 19

Asp Pro Glu Lys Val Gly Arg Pro Val Arg Gly Gly Val Ile Glu His
```

```
1               5                   10                  15

Val Asp Leu Leu Pro Gln Arg Val Pro Gly Arg Ile Glu Ile Ala Leu
            20                  25                  30

Leu Thr Val Pro Arg Glu Ala Ala Gln Lys Ala Ala Asp Leu Leu Val
        35                  40                  45

Ala Ala Gly Ile Lys Gly Ile Leu Asn Phe Ala Pro Val Val Leu Glu
    50                  55                  60

Val Pro Lys Glu Val Ala Val Glu Asn Val Asp Phe Leu Ala Gly Leu
65                  70                  75                  80

Thr Arg Leu Ser Phe Ala Ile Leu Asn Pro Lys Trp Arg Glu Glu Met
                85                  90                  95

Met Gly


<210> SEQ ID NO 20
<211> LENGTH: 238
<212> TYPE: PRT
<213> ORGANISM: Aequorea victoria

<400> SEQUENCE: 20

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 21
<211> LENGTH: 239
<212> TYPE: PRT
<213> ORGANISM: Aequorea victoria

<400> SEQUENCE: 21
```

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 22
<211> LENGTH: 246
<212> TYPE: PRT
<213> ORGANISM: Aequorea victoria

<400> SEQUENCE: 22

Tyr Asn Ser Asp Asn Val Tyr Ile Met Ala Asp Lys Gln Lys Asn Gly
1               5                   10                  15

Ile Lys Ala Asn Phe Lys Ile Arg His Asn Val Glu Asp Gly Ser Val
            20                  25                  30

Gln Leu Ala Asp His Tyr Gln Gln Asn Thr Pro Ile Gly Asp Gly Pro
        35                  40                  45

Val Leu Leu Pro Asp Asn His Tyr Leu Ser Phe Gln Ser Val Leu Ser
    50                  55                  60

Lys Asp Pro Asn Glu Lys Arg Asp His Met Val Leu Leu Glu Phe Val
65                  70                  75                  80

Thr Ala Ala Gly Ile Thr Leu Gly Met Asp Glu Leu Tyr Asn Val Asp
                85                  90                  95

Gly Gly Ser Gly Gly Thr Gly Ser Lys Gly Glu Glu Leu Phe Thr Gly
            100                 105                 110

Val Val Pro Ile Leu Val Glu Leu Asp Gly Asp Val Asn Gly His Lys
        115                 120                 125

Phe Ser Val Ser Gly Glu Gly Glu Gly Asp Ala Thr Tyr Gly Lys Leu
```

```
    130                 135                 140

Thr Leu Lys Leu Ile Cys Thr Thr Gly Lys Leu Pro Val Pro Trp Pro
145                 150                 155                 160

Thr Leu Val Thr Thr Leu Gly Tyr Gly Leu Lys Cys Phe Ala Arg Tyr
                165                 170                 175

Pro Asp His Met Lys Gln His Asp Phe Phe Lys Ser Ala Met Pro Glu
            180                 185                 190

Gly Tyr Val Gln Glu Arg Thr Ile Phe Phe Lys Asp Asp Gly Asn Tyr
        195                 200                 205

Lys Thr Arg Ala Glu Val Lys Phe Glu Gly Asp Thr Leu Val Asn Arg
    210                 215                 220

Ile Glu Leu Lys Gly Ile Gly Phe Lys Glu Asp Gly Asn Ile Leu Gly
225                 230                 235                 240

His Lys Leu Glu Tyr Asn
                245


<210> SEQ ID NO 23
<211> LENGTH: 39
<212> TYPE: DNA
<213> ORGANISM: artificial sequence
<220> FEATURE:
<223> OTHER INFORMATION: primer P1

<400> SEQUENCE: 23

gaaatcgaaa ctagttacaa cagccacaac gtctatatc                            39


<210> SEQ ID NO 24
<211> LENGTH: 35
<212> TYPE: DNA
<213> ORGANISM: artificial sequence
<220> FEATURE:
<223> OTHER INFORMATION: primer P2

<400> SEQUENCE: 24

ccaagcttcg ggtaccgtt gtactccagc ttgtg                                 35


<210> SEQ ID NO 25
<211> LENGTH: 33
<212> TYPE: DNA
<213> ORGANISM: artificial sequence
<220> FEATURE:
<223> OTHER INFORMATION: primer ydiH 1F

<400> SEQUENCE: 25

ccggatccat gaataaggat caatcaaaaa ttc                                  33


<210> SEQ ID NO 26
<211> LENGTH: 34
<212> TYPE: DNA
<213> ORGANISM: artificial sequence
<220> FEATURE:
<223> OTHER INFORMATION: primer ydiH 1R

<400> SEQUENCE: 26

gctgttgtaa ctagtttcga tttcctctaa aact                                 34


<210> SEQ ID NO 27
<211> LENGTH: 34
<212> TYPE: DNA
<213> ORGANISM: artificial sequence
<220> FEATURE:
<223> OTHER INFORMATION: primer ydiH(D2) 2F
```

<400> SEQUENCE: 27
cggggtacca tgacagacgt catcttgatt ggtg 34

<210> SEQ ID NO 28
<211> LENGTH: 30
<212> TYPE: DNA
<213> ORGANISM: artificial sequence
<220> FEATURE:
<223> OTHER INFORMATION: primer ydiH 2R

<400> SEQUENCE: 28
cccaagcttc tattcgattt cctctaaaac 30

<210> SEQ ID NO 29
<211> LENGTH: 36
<212> TYPE: DNA
<213> ORGANISM: artificial sequence
<220> FEATURE:
<223> OTHER INFORMATION: primer P1

<400> SEQUENCE: 29
gaatctgcag gctacaacag ccacaacgtc tatatc 36

<210> SEQ ID NO 30
<211> LENGTH: 35
<212> TYPE: DNA
<213> ORGANISM: artificial sequence
<220> FEATURE:
<223> OTHER INFORMATION: primer P2

<400> SEQUENCE: 30
ccaagcttcg ggtaccgtt gtactccagc ttgtg 35

<210> SEQ ID NO 31
<211> LENGTH: 34
<212> TYPE: DNA
<213> ORGANISM: artificial sequence
<220> FEATURE:
<223> OTHER INFORMATION: primer P3

<400> SEQUENCE: 31
ccggatccga tgaataagga tcaatcaaaa attc 34

<210> SEQ ID NO 32
<211> LENGTH: 30
<212> TYPE: DNA
<213> ORGANISM: artificial sequence
<220> FEATURE:
<223> OTHER INFORMATION: primer P4

<400> SEQUENCE: 32
cccaagcttc tattcgattt cctctaaaac 30

<210> SEQ ID NO 33
<211> LENGTH: 33
<212> TYPE: DNA
<213> ORGANISM: artificial sequence
<220> FEATURE:
<223> OTHER INFORMATION: primer P5

<400> SEQUENCE: 33
ataggtaccg gcctggccgg cctgacccgg ctg 33

<210> SEQ ID NO 34
<211> LENGTH: 37

<212> TYPE: DNA
<213> ORGANISM: artificial sequence
<220> FEATURE:
<223> OTHER INFORMATION: primer P6

<400> SEQUENCE: 34
atactgcaga gaagtccacg ttctccacgg ccacctc 37

<210> SEQ ID NO 35
<211> LENGTH: 28
<212> TYPE: DNA
<213> ORGANISM: artificial sequence
<220> FEATURE:
<223> OTHER INFORMATION: C9 reverse primer

<400> SEQUENCE: 35
gatttcctct aaaactgaat aatgcttc 28

<210> SEQ ID NO 36
<211> LENGTH: 25
<212> TYPE: DNA
<213> ORGANISM: artificial sequence
<220> FEATURE:
<223> OTHER INFORMATION: C8 reverse primer

<400> SEQUENCE: 36
ttcctctaaa actgaataat gcttc 25

<210> SEQ ID NO 37
<211> LENGTH: 33
<212> TYPE: DNA
<213> ORGANISM: artificial sequence
<220> FEATURE:
<223> OTHER INFORMATION: C6 reverse primer

<400> SEQUENCE: 37
taaaactgaa taatgcttca aaaaataaac cag 33

<210> SEQ ID NO 38
<211> LENGTH: 30
<212> TYPE: DNA
<213> ORGANISM: artificial sequence
<220> FEATURE:
<223> OTHER INFORMATION: C5 reverse primer

<400> SEQUENCE: 38
aactgaataa tgcttcaaaa aataaaccag 30

<210> SEQ ID NO 39
<211> LENGTH: 27
<212> TYPE: DNA
<213> ORGANISM: artificial sequence
<220> FEATURE:
<223> OTHER INFORMATION: C4 reverse primer

<400> SEQUENCE: 39
tgaataatgc ttcaaaaaat aaaccag 27

<210> SEQ ID NO 40
<211> LENGTH: 26
<212> TYPE: DNA
<213> ORGANISM: artificial sequence
<220> FEATURE:
<223> OTHER INFORMATION: C3 reverse primer

<400> SEQUENCE: 40
ataatgcttc aaaaaataaa ccagtg 26

<210> SEQ ID NO 41
<211> LENGTH: 27
<212> TYPE: DNA
<213> ORGANISM: artificial sequence
<220> FEATURE:
<223> OTHER INFORMATION: C2 reverse primer

<400> SEQUENCE: 41
atgcttcaaa aaataaacca gtgactg 27

<210> SEQ ID NO 42
<211> LENGTH: 28
<212> TYPE: DNA
<213> ORGANISM: artificial sequence
<220> FEATURE:
<223> OTHER INFORMATION: C1 reverse primer

<400> SEQUENCE: 42
cttcaaaaaa taaaccagtg actgaagc 28

<210> SEQ ID NO 43
<211> LENGTH: 18
<212> TYPE: DNA
<213> ORGANISM: artificial sequence
<220> FEATURE:
<223> OTHER INFORMATION: C9 forward primer

<400> SEQUENCE: 43
tacaacagcg acaacgtc 18

<210> SEQ ID NO 44
<211> LENGTH: 22
<212> TYPE: DNA
<213> ORGANISM: artificial sequence
<220> FEATURE:
<223> OTHER INFORMATION: C7 reverse primer

<400> SEQUENCE: 44
ctctaaaact gaataatgct tc 22

<210> SEQ ID NO 45
<211> LENGTH: 22
<212> TYPE: DNA
<213> ORGANISM: artificial sequence
<220> FEATURE:
<223> OTHER INFORMATION: Del GT forward primer

<400> SEQUENCE: 45
atgacagacg tcatcttgat tg 22

<210> SEQ ID NO 46
<211> LENGTH: 20
<212> TYPE: DNA
<213> ORGANISM: artificial sequence
<220> FEATURE:
<223> OTHER INFORMATION: Del GT reverse primer

<400> SEQUENCE: 46
gttgtactcc agcttgtgcc 20

<210> SEQ ID NO 47
<211> LENGTH: 27
<212> TYPE: DNA
<213> ORGANISM: artificial sequence
<220> FEATURE:
<223> OTHER INFORMATION: Del TS forward primer

<400> SEQUENCE: 47
tacaacagcg acaacgtcta tatcatg 27

<210> SEQ ID NO 48
<211> LENGTH: 28
<212> TYPE: DNA
<213> ORGANISM: artificial sequence
<220> FEATURE:
<223> OTHER INFORMATION: Del TS reverse primer

<400> SEQUENCE: 48
ttcgatttcc tctaaaactg aataatgc 28

<210> SEQ ID NO 49
<211> LENGTH: 30
<212> TYPE: DNA
<213> ORGANISM: artificial sequence
<220> FEATURE:
<223> OTHER INFORMATION: Del T(1)forward primer

<400> SEQUENCE: 49
agttacaaca gcgacaacgt ctatatcatg 30

<210> SEQ ID NO 50
<211> LENGTH: 31
<212> TYPE: DNA
<213> ORGANISM: artificial sequence
<220> FEATURE:
<223> OTHER INFORMATION: Del S reverse primer

<400> SEQUENCE: 50
agtttcgatt tcctctaaaa ctgaataatg c 31

<210> SEQ ID NO 51
<211> LENGTH: 25
<212> TYPE: DNA
<213> ORGANISM: artificial sequence
<220> FEATURE:
<223> OTHER INFORMATION: Del G forward primer

<400> SEQUENCE: 51
accatgacag acgtcatctt gattg 25

<210> SEQ ID NO 52
<211> LENGTH: 23
<212> TYPE: DNA
<213> ORGANISM: artificial sequence
<220> FEATURE:
<223> OTHER INFORMATION: Del T(2) reverse primer

<400> SEQUENCE: 52
accgttgtac tccagcttgt gcc 23

<210> SEQ ID NO 53
<211> LENGTH: 27
<212> TYPE: DNA
<213> ORGANISM: artificial sequence
<220> FEATURE:
<223> OTHER INFORMATION: D118K forward primer

<400> SEQUENCE: 53
ttttaagata aatgagagta aaatagg 27

```
<210> SEQ ID NO 54
<211> LENGTH: 24
<212> TYPE: DNA
<213> ORGANISM: artificial sequence
<220> FEATURE:
<223> OTHER INFORMATION: 118/120 mutation reverse primer

<400> SEQUENCE: 54

gccatagaaa tttttgtgtt attg                                              24


<210> SEQ ID NO 55
<211> LENGTH: 27
<212> TYPE: DNA
<213> ORGANISM: artificial sequence
<220> FEATURE:
<223> OTHER INFORMATION: D118R forward primer

<400> SEQUENCE: 55

ttttcggata aatgagagta aaatagg                                           27


<210> SEQ ID NO 56
<211> LENGTH: 27
<212> TYPE: DNA
<213> ORGANISM: artificial sequence
<220> FEATURE:
<223> OTHER INFORMATION: N120K forward primer

<400> SEQUENCE: 56

ttttgatata aaggagagta aaatagg                                           27


<210> SEQ ID NO 57
<211> LENGTH: 27
<212> TYPE: DNA
<213> ORGANISM: artificial sequence
<220> FEATURE:
<223> OTHER INFORMATION: N120R forward primer

<400> SEQUENCE: 57

ttttgatata cgggagagta aaatagg                                           27


<210> SEQ ID NO 58
<211> LENGTH: 27
<212> TYPE: DNA
<213> ORGANISM: artificial sequence
<220> FEATURE:
<223> OTHER INFORMATION: N120E forward primer

<400> SEQUENCE: 58

ttttgatata gaagagagta aaatagg                                           27


<210> SEQ ID NO 59
<211> LENGTH: 27
<212> TYPE: DNA
<213> ORGANISM: artificial sequence
<220> FEATURE:
<223> OTHER INFORMATION: N120D forward primer

<400> SEQUENCE: 59

ttttgatata gatgagagta aaatagg                                           27


<210> SEQ ID NO 60
<211> LENGTH: 23
<212> TYPE: DNA
<213> ORGANISM: artificial sequence
<220> FEATURE:
<223> OTHER INFORMATION: D193N forward primer
```

<400> SEQUENCE: 60
taaatttagc agttgagctt cag 23

<210> SEQ ID NO 61
<211> LENGTH: 22
<212> TYPE: DNA
<213> ORGANISM: artificial sequence
<220> FEATURE:
<223> OTHER INFORMATION: 193/194 mutation reverse primer

<400> SEQUENCE: 61
tatgatgaat tcgaatgtgt tc 22

<210> SEQ ID NO 62
<211> LENGTH: 23
<212> TYPE: DNA
<213> ORGANISM: artificial sequence
<220> FEATURE:
<223> OTHER INFORMATION: D193K forward primer

<400> SEQUENCE: 62
taaagttagc agttgagctt cag 23

<210> SEQ ID NO 63
<211> LENGTH: 23
<212> TYPE: DNA
<213> ORGANISM: artificial sequence
<220> FEATURE:
<223> OTHER INFORMATION: D193R forward primer

<400> SEQUENCE: 63
tacggttagc agttgagctt cag 23

<210> SEQ ID NO 64
<211> LENGTH: 23
<212> TYPE: DNA
<213> ORGANISM: artificial sequence
<220> FEATURE:
<223> OTHER INFORMATION: L194E forward primer

<400> SEQUENCE: 64
tagatgaagc agttgagctt cag 23

<210> SEQ ID NO 65
<211> LENGTH: 23
<212> TYPE: DNA
<213> ORGANISM: artificial sequence
<220> FEATURE:
<223> OTHER INFORMATION: L194D forward primer

<400> SEQUENCE: 65
tagatgatgc agttgagctt cag 23

<210> SEQ ID NO 66
<211> LENGTH: 23
<212> TYPE: DNA
<213> ORGANISM: artificial sequence
<220> FEATURE:
<223> OTHER INFORMATION: L194K forward primer

<400> SEQUENCE: 66
tagataaggc agttgagctt cag 23

<210> SEQ ID NO 67

<211> LENGTH: 23
<212> TYPE: DNA
<213> ORGANISM: artificial sequence
<220> FEATURE:
<223> OTHER INFORMATION: L194R forward primer

<400> SEQUENCE: 67
tagatcgggc agttgagctt cag 23

<210> SEQ ID NO 68
<211> LENGTH: 24
<212> TYPE: DNA
<213> ORGANISM: artificial sequence
<220> FEATURE:
<223> OTHER INFORMATION: 189/190-N1 forward primer

<400> SEQUENCE: 68
gcaggctaca acagcgacaa cgtc 24

<210> SEQ ID NO 69
<211> LENGTH: 24
<212> TYPE: DNA
<213> ORGANISM: artificial sequence
<220> FEATURE:
<223> OTHER INFORMATION: 189/190-N1 reverse primer

<400> SEQUENCE: 69
gaagtccacg ttctccacgg ccac 24

<210> SEQ ID NO 70
<211> LENGTH: 30
<212> TYPE: DNA
<213> ORGANISM: artificial sequence
<220> FEATURE:
<223> OTHER INFORMATION: 189/190-N2 forward primer

<400> SEQUENCE: 70
ggctacaaca gcgacaacgt ctatatcatg 30

<210> SEQ ID NO 71
<211> LENGTH: 29
<212> TYPE: DNA
<213> ORGANISM: artificial sequence
<220> FEATURE:
<223> OTHER INFORMATION: 189/190-N3 forward primer

<400> SEQUENCE: 71
tacaacagcg acaacgtcta tatcatggc 29

<210> SEQ ID NO 72
<211> LENGTH: 23
<212> TYPE: DNA
<213> ORGANISM: artificial sequence
<220> FEATURE:
<223> OTHER INFORMATION: 189/190-C1 forward primer

<400> SEQUENCE: 72
ctggccggcc tgacccggct gag 23

<210> SEQ ID NO 73
<211> LENGTH: 31
<212> TYPE: DNA
<213> ORGANISM: artificial sequence
<220> FEATURE:
<223> OTHER INFORMATION: 189/190-C1 reverse primer

<400> SEQUENCE: 73
ggtaccgttg tactccagct tgtgccccag g 31

<210> SEQ ID NO 74
<211> LENGTH: 31
<212> TYPE: DNA
<213> ORGANISM: artificial sequence
<220> FEATURE:
<223> OTHER INFORMATION: 189/190-C2 reverse primer

<400> SEQUENCE: 74
accgttgtac tccagcttgt gccccaggat g 31

<210> SEQ ID NO 75
<211> LENGTH: 32
<212> TYPE: DNA
<213> ORGANISM: artificial sequence
<220> FEATURE:
<223> OTHER INFORMATION: 189/190-C3 reverse primer

<400> SEQUENCE: 75
gttgtactcc agcttgtgcc ccaggatgtt gc 32

<210> SEQ ID NO 76
<211> LENGTH: 21
<212> TYPE: DNA
<213> ORGANISM: artificial sequence
<220> FEATURE:
<223> OTHER INFORMATION: Trex(D2)forward primer

<400> SEQUENCE: 76
atgaaccgga agtggggcct g 21

<210> SEQ ID NO 77
<211> LENGTH: 25
<212> TYPE: DNA
<213> ORGANISM: artificial sequence
<220> FEATURE:
<223> OTHER INFORMATION: Trex(D2) reverse primer

<400> SEQUENCE: 77
cggatcctta tcgtcatcgt cgtac 25

<210> SEQ ID NO 78
<211> LENGTH: 21
<212> TYPE: DNA
<213> ORGANISM: artificial sequence
<220> FEATURE:
<223> OTHER INFORMATION: D112SV113H forward primer

<400> SEQUENCE: 78
catgaccccg agaaggtggg c 21

<210> SEQ ID NO 79
<211> LENGTH: 21
<212> TYPE: DNA
<213> ORGANISM: artificial sequence
<220> FEATURE:
<223> OTHER INFORMATION: D112SV113H reverse primer

<400> SEQUENCE: 79
cgagaagaag ccccgcagct c 21

<210> SEQ ID NO 80
<211> LENGTH: 32
<212> TYPE: DNA

```
<213> ORGANISM: artificial sequence
<220> FEATURE:
<223> OTHER INFORMATION: Cyto primer F

<400> SEQUENCE: 80

ctagcatggc ggatccacta gtaagcttaa gc                                 32


<210> SEQ ID NO 81
<211> LENGTH: 32
<212> TYPE: DNA
<213> ORGANISM: artificial sequence
<220> FEATURE:
<223> OTHER INFORMATION: Cyto primer R

<400> SEQUENCE: 81

tcgagcttaa gcttactagt ggatccgcca tg                                 32


<210> SEQ ID NO 82
<211> LENGTH: 128
<212> TYPE: DNA
<213> ORGANISM: artificial sequence
<220> FEATURE:
<223> OTHER INFORMATION: Localization signal Mito

<400> SEQUENCE: 82

ctggctagca tgaggaagat gctcgcggcc gtctcccgcg tgctgtctgg cgcttctcag     60

aagccggcaa gcagagtgct ggtagcatcc cgtaattttg caaatgatgc tacatttaag    120

gatccact                                                            128


<210> SEQ ID NO 83
<211> LENGTH: 272
<212> TYPE: DNA
<213> ORGANISM: artificial sequence
<220> FEATURE:
<223> OTHER INFORMATION: Localization signal Golgi

<400> SEQUENCE: 83

gctggctagc atggcgaggc ttcgggagcc gctcctgagc ggcagcgccg cgatgccagg     60

cgcgtcccta cagcgggcct gccgcctgct cgtggccgtc tgcgctctgc accttggcgt    120

caccctcgtt tactacctgg ctggccgcga cctgagccgc ctgccccaac tggtcggagt    180

ctccacaccg ctgcagggcg gctcgaacag tgccgccgcc atcgggcagt cctccgggga    240

gctccggacc ggaggggccg cggatccact ag                                 272


<210> SEQ ID NO 84
<211> LENGTH: 79
<212> TYPE: DNA
<213> ORGANISM: artificial sequence
<220> FEATURE:
<223> OTHER INFORMATION: Nuc primer F

<400> SEQUENCE: 84

agcttgatcc aaaaaagaag agaaaggtag atccaaaaaa gaagagaaag gtagatccaa     60

aaaagaagag aaaggtagc                                                 79


<210> SEQ ID NO 85
<211> LENGTH: 79
<212> TYPE: DNA
<213> ORGANISM: artificial sequence
<220> FEATURE:
<223> OTHER INFORMATION: Nuc primer R

<400> SEQUENCE: 85
```

tcgagctacc tttctcttct tttttggatc tacctttctc ttcttttttg gatctacctt 60
tctcttcttt tttggatca 79

<210> SEQ ID NO 86
<211> LENGTH: 71
<212> TYPE: DNA
<213> ORGANISM: artificial sequence
<220> FEATURE:
<223> OTHER INFORMATION: Mem primer F

<400> SEQUENCE: 86
ctagcatggc gctgtgctgt atgagaagaa ccaaacaggt tgaaaagaat gatgaggacc 60
aaaagatcgc g 71

<210> SEQ ID NO 87
<211> LENGTH: 71
<212> TYPE: DNA
<213> ORGANISM: artificial sequence
<220> FEATURE:
<223> OTHER INFORMATION: Mem primer R

<400> SEQUENCE: 87
gatccgcgat cttttggtcc tcatcattct tttcaacctg tttggttctt ctcatacagc 60
acagcgccat g 71

<210> SEQ ID NO 88
<211> LENGTH: 62
<212> TYPE: DNA
<213> ORGANISM: artificial sequence
<220> FEATURE:
<223> OTHER INFORMATION: ER primer F

<400> SEQUENCE: 88
ctagcatggc gctgctatcc gtgccgttgc tgctcggcct cctcggcctg gccgtcgccg 60
cg 62

<210> SEQ ID NO 89
<211> LENGTH: 62
<212> TYPE: DNA
<213> ORGANISM: artificial sequence
<220> FEATURE:
<223> OTHER INFORMATION: ER primer R

<400> SEQUENCE: 89
gatccgcggc gacggccagg ccgaggaggc cgagcagcaa cggcacggat agcagcgcca 60
tg 62

<210> SEQ ID NO 90
<211> LENGTH: 18
<212> TYPE: DNA
<213> ORGANISM: artificial sequence
<220> FEATURE:
<223> OTHER INFORMATION: Peroxi primer F

<400> SEQUENCE: 90
agctttccaa gctgtaac 18

<210> SEQ ID NO 91
<211> LENGTH: 18
<212> TYPE: DNA
<213> ORGANISM: artificial sequence
<220> FEATURE:

<223> OTHER INFORMATION: Peroxi primer R

<400> SEQUENCE: 91
tcgagttaca gcttggaa 18

<210> SEQ ID NO 92
<211> LENGTH: 620
<212> TYPE: PRT
<213> ORGANISM: artificial sequence
<220> FEATURE:
<223> OTHER INFORMATION: Synthetic fluorescent sensor, mutant

<400> SEQUENCE: 92

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys Tyr
225                 230                 235                 240

Asn Ser Asp Asn Val Tyr Ile Met Ala Asp Lys Gln Lys Asn Gly Ile
                245                 250                 255

Lys Ala Asn Phe Lys Ile Arg His Asn Val Glu Asp Gly Ser Val Gln
            260                 265                 270

Leu Ala Asp His Tyr Gln Gln Asn Thr Pro Ile Gly Asp Gly Pro Val
        275                 280                 285

Leu Leu Pro Asp Asn His Tyr Leu Ser Phe Gln Ser Val Leu Ser Lys
    290                 295                 300

Asp Pro Asn Glu Lys Arg Asp His Met Val Leu Leu Glu Phe Val Thr
305                 310                 315                 320

Ala Ala Gly Ile Thr Leu Gly Met Asp Glu Leu Tyr Asn Val Asp Gly
                325                 330                 335
```

```
Gly Ser Gly Gly Thr Gly Ser Lys Gly Glu Glu Leu Phe Thr Gly Val
            340                 345                 350

Val Pro Ile Leu Val Glu Leu Asp Gly Asp Val Asn Gly His Lys Phe
        355                 360                 365

Ser Val Ser Gly Glu Gly Glu Gly Asp Ala Thr Tyr Gly Lys Leu Thr
    370                 375                 380

Leu Lys Leu Ile Cys Thr Thr Gly Lys Leu Pro Val Pro Trp Pro Thr
385                 390                 395                 400

Leu Val Thr Thr Leu Gly Tyr Gly Leu Lys Cys Phe Ala Arg Tyr Pro
                405                 410                 415

Asp His Met Lys Gln His Asp Phe Phe Lys Ser Ala Met Pro Glu Gly
            420                 425                 430

Tyr Val Gln Glu Arg Thr Ile Phe Phe Lys Asp Asp Gly Asn Tyr Lys
        435                 440                 445

Thr Arg Ala Glu Val Lys Phe Glu Gly Asp Thr Leu Val Asn Arg Ile
    450                 455                 460

Glu Leu Lys Gly Ile Gly Phe Lys Glu Asp Gly Asn Ile Leu Gly His
465                 470                 475                 480

Lys Leu Glu Tyr Asn Gly Thr Met Thr Asp Val Ile Leu Ile Gly Val
                485                 490                 495

Gly Asn Leu Gly Thr Ala Phe Leu His Tyr Asn Phe Thr Lys Asn Asn
            500                 505                 510

Asn Thr Lys Ile Ser Met Ala Phe Asp Ile Asn Glu Ser Lys Ile Gly
        515                 520                 525

Thr Glu Val Gly Gly Val Pro Val Tyr Asn Leu Asp Asp Leu Glu Gln
    530                 535                 540

His Val Lys Asp Glu Ser Val Ala Ile Leu Thr Val Pro Ala Val Ala
545                 550                 555                 560

Ala Gln Ser Ile Thr Asp Arg Leu Val Ala Leu Gly Ile Lys Gly Ile
                565                 570                 575

Leu Asn Phe Thr Pro Ala Arg Leu Asn Val Pro Glu His Ile Arg Ile
            580                 585                 590

His His Ile Asp Leu Ala Val Glu Leu Gln Ser Leu Val Tyr Phe Leu
        595                 600                 605

Lys His Tyr Ser Val Leu Glu Glu Ile Glu Lys Leu
    610                 615                 620


<210> SEQ ID NO 93
<211> LENGTH: 621
<212> TYPE: PRT
<213> ORGANISM: artificial sequence
<220> FEATURE:
<223> OTHER INFORMATION: Synthetic fluorescent sensor, mutant

<400> SEQUENCE: 93

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80
```

```
Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Asn Ser Asp Asn Val Tyr Ile Met Ala Asp Lys Gln Lys Asn Gly
                245                 250                 255

Ile Lys Ala Asn Phe Lys Ile Arg His Asn Val Glu Asp Gly Ser Val
            260                 265                 270

Gln Leu Ala Asp His Tyr Gln Gln Asn Thr Pro Ile Gly Asp Gly Pro
        275                 280                 285

Val Leu Leu Pro Asp Asn His Tyr Leu Ser Phe Gln Ser Val Leu Ser
    290                 295                 300

Lys Asp Pro Asn Glu Lys Arg Asp His Met Val Leu Leu Glu Phe Val
305                 310                 315                 320

Thr Ala Ala Gly Ile Thr Leu Gly Met Asp Glu Leu Tyr Asn Val Asp
                325                 330                 335

Gly Gly Ser Gly Gly Thr Gly Ser Lys Gly Glu Glu Leu Phe Thr Gly
            340                 345                 350

Val Val Pro Ile Leu Val Glu Leu Asp Gly Asp Val Asn Gly His Lys
        355                 360                 365

Phe Ser Val Ser Gly Glu Gly Glu Gly Asp Ala Thr Tyr Gly Lys Leu
    370                 375                 380

Thr Leu Lys Leu Ile Cys Thr Thr Gly Lys Leu Pro Val Pro Trp Pro
385                 390                 395                 400

Thr Leu Val Thr Thr Leu Gly Tyr Gly Leu Lys Cys Phe Ala Arg Tyr
                405                 410                 415

Pro Asp His Met Lys Gln His Asp Phe Phe Lys Ser Ala Met Pro Glu
            420                 425                 430

Gly Tyr Val Gln Glu Arg Thr Ile Phe Phe Lys Asp Asp Gly Asn Tyr
        435                 440                 445

Lys Thr Arg Ala Glu Val Lys Phe Glu Gly Asp Thr Leu Val Asn Arg
    450                 455                 460

Ile Glu Leu Lys Gly Ile Gly Phe Lys Glu Asp Gly Asn Ile Leu Gly
465                 470                 475                 480

His Lys Leu Glu Tyr Asn Gly Thr Met Thr Asp Val Ile Leu Ile Gly
                485                 490                 495

Val Gly Asn Leu Gly Thr Ala Phe Leu His Tyr Asn Phe Thr Lys Asn
```

```
            500                 505                 510

Asn Asn Thr Lys Ile Ser Met Ala Phe Asp Ile Asn Glu Ser Lys Ile
        515                 520                 525

Gly Thr Glu Val Gly Gly Val Pro Val Tyr Asn Leu Asp Asp Leu Glu
    530                 535                 540

Gln His Val Lys Asp Glu Ser Val Ala Ile Leu Thr Val Pro Ala Val
545                 550                 555                 560

Ala Ala Gln Ser Ile Thr Asp Arg Leu Val Ala Leu Gly Ile Lys Gly
                565                 570                 575

Ile Leu Asn Phe Thr Pro Ala Arg Leu Asn Val Pro Glu His Ile Arg
            580                 585                 590

Ile His His Ile Asp Leu Ala Val Glu Leu Gln Ser Leu Val Tyr Phe
        595                 600                 605

Leu Lys His Tyr Ser Val Leu Glu Glu Ile Glu Lys Leu
    610                 615                 620


<210> SEQ ID NO 94
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 94

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
```

```
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620
```

<210> SEQ ID NO 95
<211> LENGTH: 623
<212> TYPE: PRT
<213> ORGANISM: artificial sequence
<220> FEATURE:
<223> OTHER INFORMATION: Synthetic fluorescent sensor, mutant

<400> SEQUENCE: 95

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Tyr Asn Ser Asp Asn Val Tyr Ile Met Ala Asp Lys Gln Lys
                245                 250                 255

Asn Gly Ile Lys Ala Asn Phe Lys Ile Arg His Asn Val Glu Asp Gly
            260                 265                 270

Ser Val Gln Leu Ala Asp His Tyr Gln Gln Asn Thr Pro Ile Gly Asp
        275                 280                 285

Gly Pro Val Leu Leu Pro Asp Asn His Tyr Leu Ser Phe Gln Ser Val
    290                 295                 300

Leu Ser Lys Asp Pro Asn Glu Lys Arg Asp His Met Val Leu Leu Glu
305                 310                 315                 320

Phe Val Thr Ala Ala Gly Ile Thr Leu Gly Met Asp Glu Leu Tyr Asn
                325                 330                 335

Val Asp Gly Gly Ser Gly Gly Thr Gly Ser Lys Gly Glu Glu Leu Phe
            340                 345                 350

Thr Gly Val Val Pro Ile Leu Val Glu Leu Asp Gly Asp Val Asn Gly
        355                 360                 365

His Lys Phe Ser Val Ser Gly Glu Gly Glu Gly Asp Ala Thr Tyr Gly
    370                 375                 380

Lys Leu Thr Leu Lys Leu Ile Cys Thr Thr Gly Lys Leu Pro Val Pro
385                 390                 395                 400

Trp Pro Thr Leu Val Thr Thr Leu Gly Tyr Gly Leu Lys Cys Phe Ala
                405                 410                 415
```

```
Arg Tyr Pro Asp His Met Lys Gln His Asp Phe Phe Lys Ser Ala Met
            420                 425                 430

Pro Glu Gly Tyr Val Gln Glu Arg Thr Ile Phe Phe Lys Asp Asp Gly
        435                 440                 445

Asn Tyr Lys Thr Arg Ala Glu Val Lys Phe Glu Gly Asp Thr Leu Val
    450                 455                 460

Asn Arg Ile Glu Leu Lys Gly Ile Gly Phe Lys Glu Asp Gly Asn Ile
465                 470                 475                 480

Leu Gly His Lys Leu Glu Tyr Asn Gly Thr Met Thr Asp Val Ile Leu
                485                 490                 495

Ile Gly Val Gly Asn Leu Gly Thr Ala Phe Leu His Tyr Asn Phe Thr
            500                 505                 510

Lys Asn Asn Asn Thr Lys Ile Ser Met Ala Phe Asp Ile Asn Glu Ser
        515                 520                 525

Lys Ile Gly Thr Glu Val Gly Gly Val Pro Val Tyr Asn Leu Asp Asp
    530                 535                 540

Leu Glu Gln His Val Lys Asp Glu Ser Val Ala Ile Leu Thr Val Pro
545                 550                 555                 560

Ala Val Ala Ala Gln Ser Ile Thr Asp Arg Leu Val Ala Leu Gly Ile
                565                 570                 575

Lys Gly Ile Leu Asn Phe Thr Pro Ala Arg Leu Asn Val Pro Glu His
            580                 585                 590

Ile Arg Ile His His Ile Asp Leu Ala Val Glu Leu Gln Ser Leu Val
        595                 600                 605

Tyr Phe Leu Lys His Tyr Ser Val Leu Glu Glu Ile Glu Lys Leu
    610                 615                 620


<210> SEQ ID NO 96
<211> LENGTH: 624
<212> TYPE: PRT
<213> ORGANISM: artificial sequence
<220> FEATURE:
<223> OTHER INFORMATION: Synthetic fluorescent sensor, mutant

<400> SEQUENCE: 96

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160
```

```
Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Tyr Asn Ser Asp Asn Val Tyr Ile Met Ala Asp Lys Gln
                245                 250                 255

Lys Asn Gly Ile Lys Ala Asn Phe Lys Ile Arg His Asn Val Glu Asp
            260                 265                 270

Gly Ser Val Gln Leu Ala Asp His Tyr Gln Gln Asn Thr Pro Ile Gly
        275                 280                 285

Asp Gly Pro Val Leu Leu Pro Asp Asn His Tyr Leu Ser Phe Gln Ser
    290                 295                 300

Val Leu Ser Lys Asp Pro Asn Glu Lys Arg Asp His Met Val Leu Leu
305                 310                 315                 320

Glu Phe Val Thr Ala Ala Gly Ile Thr Leu Gly Met Asp Glu Leu Tyr
                325                 330                 335

Asn Val Asp Gly Gly Ser Gly Gly Thr Gly Ser Lys Gly Glu Glu Leu
            340                 345                 350

Phe Thr Gly Val Val Pro Ile Leu Val Glu Leu Asp Gly Asp Val Asn
        355                 360                 365

Gly His Lys Phe Ser Val Ser Gly Glu Gly Glu Gly Asp Ala Thr Tyr
    370                 375                 380

Gly Lys Leu Thr Leu Lys Leu Ile Cys Thr Thr Gly Lys Leu Pro Val
385                 390                 395                 400

Pro Trp Pro Thr Leu Val Thr Thr Leu Gly Tyr Gly Leu Lys Cys Phe
                405                 410                 415

Ala Arg Tyr Pro Asp His Met Lys Gln His Asp Phe Phe Lys Ser Ala
            420                 425                 430

Met Pro Glu Gly Tyr Val Gln Glu Arg Thr Ile Phe Phe Lys Asp Asp
        435                 440                 445

Gly Asn Tyr Lys Thr Arg Ala Glu Val Lys Phe Glu Gly Asp Thr Leu
    450                 455                 460

Val Asn Arg Ile Glu Leu Lys Gly Ile Gly Phe Lys Glu Asp Gly Asn
465                 470                 475                 480

Ile Leu Gly His Lys Leu Glu Tyr Asn Gly Thr Met Thr Asp Val Ile
                485                 490                 495

Leu Ile Gly Val Gly Asn Leu Gly Thr Ala Phe Leu His Tyr Asn Phe
            500                 505                 510

Thr Lys Asn Asn Asn Thr Lys Ile Ser Met Ala Phe Asp Ile Asn Glu
        515                 520                 525

Ser Lys Ile Gly Thr Glu Val Gly Gly Val Pro Val Tyr Asn Leu Asp
    530                 535                 540

Asp Leu Glu Gln His Val Lys Asp Glu Ser Val Ala Ile Leu Thr Val
545                 550                 555                 560

Pro Ala Val Ala Ala Gln Ser Ile Thr Asp Arg Leu Val Ala Leu Gly
                565                 570                 575
```

```
Ile Lys Gly Ile Leu Asn Phe Thr Pro Ala Arg Leu Asn Val Pro Glu
            580                 585                 590

His Ile Arg Ile His His Ile Asp Leu Ala Val Glu Leu Gln Ser Leu
        595                 600                 605

Val Tyr Phe Leu Lys His Tyr Ser Val Leu Glu Glu Ile Glu Lys Leu
    610                 615                 620


<210> SEQ ID NO 97
<211> LENGTH: 625
<212> TYPE: PRT
<213> ORGANISM: artificial sequence
<220> FEATURE:
<223> OTHER INFORMATION: Synthetic fluorescent sensor, mutant

<400> SEQUENCE: 97

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
            85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Tyr Asn Ser Asp Asn Val Tyr Ile Met Ala Asp Lys
                245                 250                 255

Gln Lys Asn Gly Ile Lys Ala Asn Phe Lys Ile Arg His Asn Val Glu
            260                 265                 270

Asp Gly Ser Val Gln Leu Ala Asp His Tyr Gln Gln Asn Thr Pro Ile
        275                 280                 285

Gly Asp Gly Pro Val Leu Leu Pro Asp Asn His Tyr Leu Ser Phe Gln
    290                 295                 300

Ser Val Leu Ser Lys Asp Pro Asn Glu Lys Arg Asp His Met Val Leu
305                 310                 315                 320
```

```
Leu Glu Phe Val Thr Ala Ala Gly Ile Thr Leu Gly Met Asp Glu Leu
                325                 330                 335

Tyr Asn Val Asp Gly Gly Ser Gly Gly Thr Gly Ser Lys Gly Glu Glu
            340                 345                 350

Leu Phe Thr Gly Val Val Pro Ile Leu Val Glu Leu Asp Gly Asp Val
        355                 360                 365

Asn Gly His Lys Phe Ser Val Ser Gly Glu Gly Glu Gly Asp Ala Thr
    370                 375                 380

Tyr Gly Lys Leu Thr Leu Lys Leu Ile Cys Thr Thr Gly Lys Leu Pro
385                 390                 395                 400

Val Pro Trp Pro Thr Leu Val Thr Thr Leu Gly Tyr Gly Leu Lys Cys
                405                 410                 415

Phe Ala Arg Tyr Pro Asp His Met Lys Gln His Asp Phe Phe Lys Ser
            420                 425                 430

Ala Met Pro Glu Gly Tyr Val Gln Glu Arg Thr Ile Phe Phe Lys Asp
        435                 440                 445

Asp Gly Asn Tyr Lys Thr Arg Ala Glu Val Lys Phe Glu Gly Asp Thr
    450                 455                 460

Leu Val Asn Arg Ile Glu Leu Lys Gly Ile Gly Phe Lys Glu Asp Gly
465                 470                 475                 480

Asn Ile Leu Gly His Lys Leu Glu Tyr Asn Gly Thr Met Thr Asp Val
                485                 490                 495

Ile Leu Ile Gly Val Gly Asn Leu Gly Thr Ala Phe Leu His Tyr Asn
            500                 505                 510

Phe Thr Lys Asn Asn Asn Thr Lys Ile Ser Met Ala Phe Asp Ile Asn
        515                 520                 525

Glu Ser Lys Ile Gly Thr Glu Val Gly Gly Val Pro Val Tyr Asn Leu
    530                 535                 540

Asp Asp Leu Glu Gln His Val Lys Asp Glu Ser Val Ala Ile Leu Thr
545                 550                 555                 560

Val Pro Ala Val Ala Ala Gln Ser Ile Thr Asp Arg Leu Val Ala Leu
                565                 570                 575

Gly Ile Lys Gly Ile Leu Asn Phe Thr Pro Ala Arg Leu Asn Val Pro
            580                 585                 590

Glu His Ile Arg Ile His His Ile Asp Leu Ala Val Glu Leu Gln Ser
        595                 600                 605

Leu Val Tyr Phe Leu Lys His Tyr Ser Val Leu Glu Glu Ile Glu Lys
    610                 615                 620

Leu
625


<210> SEQ ID NO 98
<211> LENGTH: 626
<212> TYPE: PRT
<213> ORGANISM: artificial sequence
<220> FEATURE:
<223> OTHER INFORMATION: Synthetic fluorescent sensor, mutant

<400> SEQUENCE: 98

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45
```

```
Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Tyr Asn Ser Asp Asn Val Tyr Ile Met Ala Asp
                245                 250                 255

Lys Gln Lys Asn Gly Ile Lys Ala Asn Phe Lys Ile Arg His Asn Val
            260                 265                 270

Glu Asp Gly Ser Val Gln Leu Ala Asp His Tyr Gln Gln Asn Thr Pro
        275                 280                 285

Ile Gly Asp Gly Pro Val Leu Leu Pro Asp Asn His Tyr Leu Ser Phe
    290                 295                 300

Gln Ser Val Leu Ser Lys Asp Pro Asn Glu Lys Arg Asp His Met Val
305                 310                 315                 320

Leu Leu Glu Phe Val Thr Ala Ala Gly Ile Thr Leu Gly Met Asp Glu
                325                 330                 335

Leu Tyr Asn Val Asp Gly Gly Ser Gly Gly Thr Gly Ser Lys Gly Glu
            340                 345                 350

Glu Leu Phe Thr Gly Val Val Pro Ile Leu Val Glu Leu Asp Gly Asp
        355                 360                 365

Val Asn Gly His Lys Phe Ser Val Ser Gly Glu Gly Glu Gly Asp Ala
    370                 375                 380

Thr Tyr Gly Lys Leu Thr Leu Lys Leu Ile Cys Thr Thr Gly Lys Leu
385                 390                 395                 400

Pro Val Pro Trp Pro Thr Leu Val Thr Thr Leu Gly Tyr Gly Leu Lys
                405                 410                 415

Cys Phe Ala Arg Tyr Pro Asp His Met Lys Gln His Asp Phe Phe Lys
            420                 425                 430

Ser Ala Met Pro Glu Gly Tyr Val Gln Glu Arg Thr Ile Phe Phe Lys
        435                 440                 445

Asp Asp Gly Asn Tyr Lys Thr Arg Ala Glu Val Lys Phe Glu Gly Asp
    450                 455                 460

Thr Leu Val Asn Arg Ile Glu Leu Lys Gly Ile Gly Phe Lys Glu Asp
```

```
465                 470                 475                 480

Gly Asn Ile Leu Gly His Lys Leu Glu Tyr Asn Gly Thr Met Thr Asp
                485                 490                 495

Val Ile Leu Ile Gly Val Gly Asn Leu Gly Thr Ala Phe Leu His Tyr
            500                 505                 510

Asn Phe Thr Lys Asn Asn Asn Thr Lys Ile Ser Met Ala Phe Asp Ile
        515                 520                 525

Asn Glu Ser Lys Ile Gly Thr Glu Val Gly Gly Val Pro Val Tyr Asn
    530                 535                 540

Leu Asp Asp Leu Glu Gln His Val Lys Asp Glu Ser Val Ala Ile Leu
545                 550                 555                 560

Thr Val Pro Ala Val Ala Ala Gln Ser Ile Thr Asp Arg Leu Val Ala
                565                 570                 575

Leu Gly Ile Lys Gly Ile Leu Asn Phe Thr Pro Ala Arg Leu Asn Val
            580                 585                 590

Pro Glu His Ile Arg Ile His His Ile Asp Leu Ala Val Glu Leu Gln
        595                 600                 605

Ser Leu Val Tyr Phe Leu Lys His Tyr Ser Val Leu Glu Glu Ile Glu
    610                 615                 620

Lys Leu
625


<210> SEQ ID NO 99
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 99

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
```

-continued

```
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
        595                 600                 605

Gln Ser Leu Val Tyr Phe Leu Lys His Tyr Ser Val Leu Glu Glu Ile
    610                 615                 620
```

```
Glu Lys Leu
625

<210> SEQ ID NO 100
<211> LENGTH: 628
<212> TYPE: PRT
<213> ORGANISM: artificial sequence
<220> FEATURE:
<223> OTHER INFORMATION: Synthetic fluorescent sensor, mutant

<400> SEQUENCE: 100

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Tyr Asn Ser Asp Asn Val Tyr Ile Met
                245                 250                 255

Ala Asp Lys Gln Lys Asn Gly Ile Lys Ala Asn Phe Lys Ile Arg His
            260                 265                 270

Asn Val Glu Asp Gly Ser Val Gln Leu Ala Asp His Tyr Gln Gln Asn
        275                 280                 285

Thr Pro Ile Gly Asp Gly Pro Val Leu Leu Pro Asp Asn His Tyr Leu
    290                 295                 300

Ser Phe Gln Ser Val Leu Ser Lys Asp Pro Asn Glu Lys Arg Asp His
305                 310                 315                 320

Met Val Leu Leu Glu Phe Val Thr Ala Ala Gly Ile Thr Leu Gly Met
                325                 330                 335

Asp Glu Leu Tyr Asn Val Asp Gly Gly Ser Gly Gly Thr Gly Ser Lys
            340                 345                 350
```

```
Gly Glu Glu Leu Phe Thr Gly Val Val Pro Ile Leu Val Glu Leu Asp
        355                 360                 365

Gly Asp Val Asn Gly His Lys Phe Ser Val Ser Gly Glu Gly Glu Gly
    370                 375                 380

Asp Ala Thr Tyr Gly Lys Leu Thr Leu Lys Leu Ile Cys Thr Thr Gly
385                 390                 395                 400

Lys Leu Pro Val Pro Trp Pro Thr Leu Val Thr Thr Leu Gly Tyr Gly
                405                 410                 415

Leu Lys Cys Phe Ala Arg Tyr Pro Asp His Met Lys Gln His Asp Phe
            420                 425                 430

Phe Lys Ser Ala Met Pro Glu Gly Tyr Val Gln Glu Arg Thr Ile Phe
        435                 440                 445

Phe Lys Asp Asp Gly Asn Tyr Lys Thr Arg Ala Glu Val Lys Phe Glu
    450                 455                 460

Gly Asp Thr Leu Val Asn Arg Ile Glu Leu Lys Gly Ile Gly Phe Lys
465                 470                 475                 480

Glu Asp Gly Asn Ile Leu Gly His Lys Leu Glu Tyr Asn Gly Thr Met
                485                 490                 495

Thr Asp Val Ile Leu Ile Gly Val Gly Asn Leu Gly Thr Ala Phe Leu
            500                 505                 510

His Tyr Asn Phe Thr Lys Asn Asn Asn Thr Lys Ile Ser Met Ala Phe
        515                 520                 525

Asp Ile Asn Glu Ser Lys Ile Gly Thr Glu Val Gly Gly Val Pro Val
    530                 535                 540

Tyr Asn Leu Asp Asp Leu Glu Gln His Val Lys Asp Glu Ser Val Ala
545                 550                 555                 560

Ile Leu Thr Val Pro Ala Val Ala Ala Gln Ser Ile Thr Asp Arg Leu
                565                 570                 575

Val Ala Leu Gly Ile Lys Gly Ile Leu Asn Phe Thr Pro Ala Arg Leu
            580                 585                 590

Asn Val Pro Glu His Ile Arg Ile His His Ile Asp Leu Ala Val Glu
        595                 600                 605

Leu Gln Ser Leu Val Tyr Phe Leu Lys His Tyr Ser Val Leu Glu Glu
    610                 615                 620

Ile Glu Lys Leu
625


<210> SEQ ID NO 101
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 101

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80
```

```
Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Ser Tyr Asn Ser Asp Asn Val Tyr
                245                 250                 255

Ile Met Ala Asp Lys Gln Lys Asn Gly Ile Lys Ala Asn Phe Lys Ile
            260                 265                 270

Arg His Asn Val Glu Asp Gly Ser Val Gln Leu Ala Asp His Tyr Gln
        275                 280                 285

Gln Asn Thr Pro Ile Gly Asp Gly Pro Val Leu Leu Pro Asp Asn His
    290                 295                 300

Tyr Leu Ser Phe Gln Ser Val Leu Ser Lys Asp Pro Asn Glu Lys Arg
305                 310                 315                 320

Asp His Met Val Leu Leu Glu Phe Val Thr Ala Ala Gly Ile Thr Leu
                325                 330                 335

Gly Met Asp Glu Leu Tyr Asn Val Asp Gly Gly Ser Gly Gly Thr Gly
            340                 345                 350

Ser Lys Gly Glu Glu Leu Phe Thr Gly Val Val Pro Ile Leu Val Glu
        355                 360                 365

Leu Asp Gly Asp Val Asn Gly His Lys Phe Ser Val Ser Gly Glu Gly
    370                 375                 380

Glu Gly Asp Ala Thr Tyr Gly Lys Leu Thr Leu Lys Leu Ile Cys Thr
385                 390                 395                 400

Thr Gly Lys Leu Pro Val Pro Trp Pro Thr Leu Val Thr Thr Leu Gly
                405                 410                 415

Tyr Gly Leu Lys Cys Phe Ala Arg Tyr Pro Asp His Met Lys Gln His
            420                 425                 430

Asp Phe Phe Lys Ser Ala Met Pro Glu Gly Tyr Val Gln Glu Arg Thr
        435                 440                 445

Ile Phe Phe Lys Asp Asp Gly Asn Tyr Lys Thr Arg Ala Glu Val Lys
    450                 455                 460

Phe Glu Gly Asp Thr Leu Val Asn Arg Ile Glu Leu Lys Gly Ile Gly
465                 470                 475                 480

Phe Lys Glu Asp Gly Asn Ile Leu Gly His Lys Leu Glu Tyr Asn Gly
                485                 490                 495
```

```
Thr Met Thr Asp Val Ile Leu Ile Gly Val Gly Asn Leu Gly Thr Ala
            500                 505                 510

Phe Leu His Tyr Asn Phe Thr Lys Asn Asn Asn Thr Lys Ile Ser Met
        515                 520                 525

Ala Phe Asp Ile Asn Glu Ser Lys Ile Gly Thr Glu Val Gly Gly Val
    530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
    610                 615                 620

Glu Glu Ile Glu Lys Leu
625                 630


<210> SEQ ID NO 102
<211> LENGTH: 629
<212> TYPE: PRT
<213> ORGANISM: artificial sequence
<220> FEATURE:
<223> OTHER INFORMATION: Synthetic fluorescent sensor, mutant

<400> SEQUENCE: 102

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220
```

```
Ile Asp Leu Ala Val Glu Leu Gln Ser Leu Val Tyr Phe Leu Lys His
225                 230                 235                 240

Tyr Ser Val Leu Glu Glu Ile Glu Thr Ser Tyr Asn Ser Asp Asn Val
                245                 250                 255

Tyr Ile Met Ala Asp Lys Gln Lys Asn Gly Ile Lys Ala Asn Phe Lys
            260                 265                 270

Ile Arg His Asn Val Glu Asp Gly Ser Val Gln Leu Ala Asp His Tyr
        275                 280                 285

Gln Gln Asn Thr Pro Ile Gly Asp Gly Pro Val Leu Leu Pro Asp Asn
    290                 295                 300

His Tyr Leu Ser Phe Gln Ser Val Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Asn Val Asp Gly Gly Ser Gly Gly Thr
            340                 345                 350

Gly Ser Lys Gly Glu Glu Leu Phe Thr Gly Val Val Pro Ile Leu Val
        355                 360                 365

Glu Leu Asp Gly Asp Val Asn Gly His Lys Phe Ser Val Ser Gly Glu
    370                 375                 380

Gly Glu Gly Asp Ala Thr Tyr Gly Lys Leu Thr Leu Lys Leu Ile Cys
385                 390                 395                 400

Thr Thr Gly Lys Leu Pro Val Pro Trp Pro Thr Leu Val Thr Thr Leu
                405                 410                 415

Gly Tyr Gly Leu Lys Cys Phe Ala Arg Tyr Pro Asp His Met Lys Gln
            420                 425                 430

His Asp Phe Phe Lys Ser Ala Met Pro Glu Gly Tyr Val Gln Glu Arg
        435                 440                 445

Thr Ile Phe Phe Lys Asp Asp Gly Asn Tyr Lys Thr Arg Ala Glu Val
    450                 455                 460

Lys Phe Glu Gly Asp Thr Leu Val Asn Arg Ile Glu Leu Lys Gly Ile
465                 470                 475                 480

Gly Phe Lys Glu Asp Gly Asn Ile Leu Gly His Lys Leu Glu Tyr Asn
                485                 490                 495

Met Thr Asp Val Ile Leu Ile Gly Val Gly Asn Leu Gly Thr Ala Phe
            500                 505                 510

Leu His Tyr Asn Phe Thr Lys Asn Asn Asn Thr Lys Ile Ser Met Ala
        515                 520                 525

Phe Asp Ile Asn Glu Ser Lys Ile Gly Thr Glu Val Gly Gly Val Pro
    530                 535                 540

Val Tyr Asn Leu Asp Asp Leu Glu Gln His Val Lys Asp Glu Ser Val
545                 550                 555                 560

Ala Ile Leu Thr Val Pro Ala Val Ala Ala Gln Ser Ile Thr Asp Arg
                565                 570                 575

Leu Val Ala Leu Gly Ile Lys Gly Ile Leu Asn Phe Thr Pro Ala Arg
            580                 585                 590

Leu Asn Val Pro Glu His Ile Arg Ile His His Ile Asp Leu Ala Val
        595                 600                 605

Glu Leu Gln Ser Leu Val Tyr Phe Leu Lys His Tyr Ser Val Leu Glu
    610                 615                 620

Glu Ile Glu Lys Leu
625
```

<210> SEQ ID NO 103
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 103

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Ser Tyr Asn Ser Asp Asn Val
                245                 250                 255

Tyr Ile Met Ala Asp Lys Gln Lys Asn Gly Ile Lys Ala Asn Phe Lys
            260                 265                 270

Ile Arg His Asn Val Glu Asp Gly Ser Val Gln Leu Ala Asp His Tyr
        275                 280                 285

Gln Gln Asn Thr Pro Ile Gly Asp Gly Pro Val Leu Leu Pro Asp Asn
    290                 295                 300

His Tyr Leu Ser Phe Gln Ser Val Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Asn Val Asp Gly Gly Ser Gly Gly Thr
            340                 345                 350

Gly Ser Lys Gly Glu Glu Leu Phe Thr Gly Val Val Pro Ile Leu Val
        355                 360                 365

Glu Leu Asp Gly Asp Val Asn Gly His Lys Phe Ser Val Ser Gly Glu
```

```
    370                 375                 380

Gly Glu Gly Asp Ala Thr Tyr Gly Lys Leu Thr Leu Lys Leu Ile Cys
385                 390                 395                 400

Thr Thr Gly Lys Leu Pro Val Pro Trp Pro Thr Leu Val Thr Thr Leu
                405                 410                 415

Gly Tyr Gly Leu Lys Cys Phe Ala Arg Tyr Pro Asp His Met Lys Gln
            420                 425                 430

His Asp Phe Phe Lys Ser Ala Met Pro Glu Gly Tyr Val Gln Glu Arg
        435                 440                 445

Thr Ile Phe Phe Lys Asp Asp Gly Asn Tyr Lys Thr Arg Ala Glu Val
    450                 455                 460

Lys Phe Glu Gly Asp Thr Leu Val Asn Arg Ile Glu Leu Lys Gly Ile
465                 470                 475                 480

Gly Phe Lys Glu Asp Gly Asn Ile Leu Gly His Lys Leu Glu Tyr Asn
                485                 490                 495

Thr Met Thr Asp Val Ile Leu Ile Gly Val Gly Asn Leu Gly Thr Ala
            500                 505                 510

Phe Leu His Tyr Asn Phe Thr Lys Asn Asn Asn Thr Lys Ile Ser Met
        515                 520                 525

Ala Phe Asp Ile Asn Glu Ser Lys Ile Gly Thr Glu Val Gly Gly Val
    530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
    610                 615                 620

Glu Glu Ile Glu Lys Leu
625                 630


<210> SEQ ID NO 104
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 104

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
```

```
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Ser Tyr Asn Ser Asp Asn Val
                245                 250                 255

Tyr Ile Met Ala Asp Lys Gln Lys Asn Gly Ile Lys Ala Asn Phe Lys
            260                 265                 270

Ile Arg His Asn Val Glu Asp Gly Ser Val Gln Leu Ala Asp His Tyr
        275                 280                 285

Gln Gln Asn Thr Pro Ile Gly Asp Gly Pro Val Leu Leu Pro Asp Asn
    290                 295                 300

His Tyr Leu Ser Phe Gln Ser Val Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Asn Val Asp Gly Gly Ser Gly Gly Thr
            340                 345                 350

Gly Ser Lys Gly Glu Glu Leu Phe Thr Gly Val Val Pro Ile Leu Val
        355                 360                 365

Glu Leu Asp Gly Asp Val Asn Gly His Lys Phe Ser Val Ser Gly Glu
    370                 375                 380

Gly Glu Gly Asp Ala Thr Tyr Gly Lys Leu Thr Leu Lys Leu Ile Cys
385                 390                 395                 400

Thr Thr Gly Lys Leu Pro Val Pro Trp Pro Thr Leu Val Thr Thr Leu
                405                 410                 415

Gly Tyr Gly Leu Lys Cys Phe Ala Arg Tyr Pro Asp His Met Lys Gln
            420                 425                 430

His Asp Phe Phe Lys Ser Ala Met Pro Glu Gly Tyr Val Gln Glu Arg
        435                 440                 445

Thr Ile Phe Phe Lys Asp Asp Gly Asn Tyr Lys Thr Arg Ala Glu Val
    450                 455                 460

Lys Phe Glu Gly Asp Thr Leu Val Asn Arg Ile Glu Leu Lys Gly Ile
465                 470                 475                 480

Gly Phe Lys Glu Asp Gly Asn Ile Leu Gly His Lys Leu Glu Tyr Asn
                485                 490                 495

Gly Met Thr Asp Val Ile Leu Ile Gly Val Gly Asn Leu Gly Thr Ala
            500                 505                 510

Phe Leu His Tyr Asn Phe Thr Lys Asn Asn Asn Thr Lys Ile Ser Met
        515                 520                 525
```

```
Ala Phe Asp Ile Asn Glu Ser Lys Ile Gly Thr Glu Val Gly Gly Val
    530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
    610                 615                 620

Glu Glu Ile Glu Lys Leu
625                 630


<210> SEQ ID NO 105
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 105

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Arg Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255
```

```
Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Arg Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620
```

<210> SEQ ID NO 106
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 106

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Lys Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415
```

```
Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Lys Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620


<210> SEQ ID NO 107
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 107

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Arg Glu Ser Lys Ile Gly Thr Glu
145                 150                 155                 160
```

```
Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Arg Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
```

```
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620


<210> SEQ ID NO 108
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 108

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Glu Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
```

```
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Glu Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620


<210> SEQ ID NO 109
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 109

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
```

-continued

```
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asp Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495
```

```
Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asp Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620


<210> SEQ ID NO 110
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 110

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asn Leu Ala Val Glu Leu Gln Ser Leu Val Tyr Phe Leu Lys His
225                 230                 235                 240
```

```
Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asn Leu Ala Val Glu Leu Gln Ser Leu Val Tyr
        595                 600                 605

Phe Leu Lys His Tyr Ser Val Leu Glu Glu Ile Glu Lys Leu
    610                 615                 620
```

<210> SEQ ID NO 111
<211> LENGTH: 622
<212> TYPE: PRT
<213> ORGANISM: artificial sequence
<220> FEATURE:

<223> OTHER INFORMATION: Synthetic fluorescent sensor, mutant

<400> SEQUENCE: 111

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Lys Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400
```

```
Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Lys Leu Ala Val Glu Leu Gln Ser Leu Val Tyr
        595                 600                 605

Phe Leu Lys His Tyr Ser Val Leu Glu Glu Ile Glu Lys Leu
    610                 615                 620
```

<210> SEQ ID NO 112
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 112

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140
```

```
Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Lys Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
```

```
                565                 570                 575

Gly Ile Leu Asn Phe Thr Pro Ala Arg Leu Asn Val Pro Glu His Ile
            580                 585                 590

Arg Ile His His Ile Asp Lys Ala Val Glu Leu Gln Ser Leu Val Tyr
        595                 600                 605

Phe Leu Lys His Tyr Ser Val Leu Glu Glu Ile Glu Lys Leu
    610                 615                 620


<210> SEQ ID NO 113
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 113

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Arg Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
```

305 310 315 320

Val Thr Ala Ala Gly Ile Thr Leu Gly Met Asp Glu Leu Tyr Asn Val
325 330 335

Asp Gly Gly Ser Gly Gly Thr Gly Ser Lys Gly Glu Glu Leu Phe Thr
340 345 350

Gly Val Val Pro Ile Leu Val Glu Leu Asp Gly Asp Val Asn Gly His
355 360 365

Lys Phe Ser Val Ser Gly Glu Gly Glu Gly Asp Ala Thr Tyr Gly Lys
370 375 380

Leu Thr Leu Lys Leu Ile Cys Thr Thr Gly Lys Leu Pro Val Pro Trp
385 390 395 400

Pro Thr Leu Val Thr Thr Leu Gly Tyr Gly Leu Lys Cys Phe Ala Arg
405 410 415

Tyr Pro Asp His Met Lys Gln His Asp Phe Phe Lys Ser Ala Met Pro
420 425 430

Glu Gly Tyr Val Gln Glu Arg Thr Ile Phe Phe Lys Asp Asp Gly Asn
435 440 445

Tyr Lys Thr Arg Ala Glu Val Lys Phe Glu Gly Asp Thr Leu Val Asn
450 455 460

Arg Ile Glu Leu Lys Gly Ile Gly Phe Lys Glu Asp Gly Asn Ile Leu
465 470 475 480

Gly His Lys Leu Glu Tyr Asn Gly Thr Met Thr Asp Val Ile Leu Ile
485 490 495

Gly Val Gly Asn Leu Gly Thr Ala Phe Leu His Tyr Asn Phe Thr Lys
500 505 510

Asn Asn Asn Thr Lys Ile Ser Met Ala Phe Asp Ile Asn Glu Ser Lys
515 520 525

Ile Gly Thr Glu Val Gly Gly Val Pro Val Tyr Asn Leu Asp Asp Leu
530 535 540

Glu Gln His Val Lys Asp Glu Ser Val Ala Ile Leu Thr Val Pro Ala
545 550 555 560

Val Ala Ala Gln Ser Ile Thr Asp Arg Leu Val Ala Leu Gly Ile Lys
565 570 575

Gly Ile Leu Asn Phe Thr Pro Ala Arg Leu Asn Val Pro Glu His Ile
580 585 590

Arg Ile His His Ile Asp Arg Ala Val Glu Leu Gln Ser Leu Val Tyr
595 600 605

Phe Leu Lys His Tyr Ser Val Leu Glu Glu Ile Glu Lys Leu
610 615 620

<210> SEQ ID NO 114
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 114

Met Arg Gly Ser His His His His His His Gly Met Ala Ser Met Thr
1 5 10 15

Gly Gly Gln Gln Met Gly Arg Asp Leu Tyr Asp Asp Asp Asp Lys Asp
20 25 30

Pro Met Asn Lys Asp Gln Ser Lys Ile Pro Gln Ala Thr Ala Lys Arg
35 40 45

Leu Pro Leu Tyr Tyr Arg Phe Leu Lys Asn Leu His Ala Ser Gly Lys

```
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Glu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480
```

```
Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Glu Ala Val Glu Leu Gln Ser Leu Val Tyr
        595                 600                 605

Phe Leu Lys His Tyr Ser Val Leu Glu Glu Ile Glu Lys Leu
    610                 615                 620


<210> SEQ ID NO 115
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 115

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220
```

```
Ile Asp Asp Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Asp Ala Val Glu Leu Gln Ser Leu Val Tyr
        595                 600                 605

Phe Leu Lys His Tyr Ser Val Leu Glu Glu Ile Glu Lys Leu
    610                 615                 620
```

<210> SEQ ID NO 116
<211> LENGTH: 627

```
<212> TYPE: PRT
<213> ORGANISM: artificial sequence
<220> FEATURE:
<223> OTHER INFORMATION: Synthetic fluorescent sensor, mutant

<400> SEQUENCE: 116

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Arg Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380
```

```
Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Arg
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625


<210> SEQ ID NO 117
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 117

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110
```

```
Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Lys Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Lys Glu Ser Lys Ile Gly Thr Glu Val Gly Gly Val Pro Val Tyr
```

```
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625


<210> SEQ ID NO 118
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 118

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Arg Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
```

```
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Arg Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625
```

<210> SEQ ID NO 119
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 119

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Glu Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415
```

```
Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Glu Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625
```

<210> SEQ ID NO 120
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 120

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140
```

```
Lys Ile Ser Met Ala Phe Asp Ile Asp Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asp Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560
```

```
Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625


<210> SEQ ID NO 121
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 121

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asn Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285
```

```
Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asn Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625
```

<210> SEQ ID NO 122
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 122

```
Met Arg Gly Ser His His His His His His Gly Met Ala Ser Met Thr
1               5                   10                  15
```

```
Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Lys Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
```

```
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Lys Leu Ala Val Glu Leu
        595                 600                 605

Gln Ser Leu Val Tyr Phe Leu Lys His Tyr Ser Val Leu Glu Glu Ile
    610                 615                 620

Glu Lys Leu
625


<210> SEQ ID NO 123
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 123

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
```

```
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Lys Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590
```

```
Val Pro Glu His Ile Arg Ile His His Ile Asp Lys Ala Val Glu Leu
        595                 600                 605

Gln Ser Leu Val Tyr Phe Leu Lys His Tyr Ser Val Leu Glu Glu Ile
    610                 615                 620

Glu Lys Leu
625


<210> SEQ ID NO 124
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 124

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Arg Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320
```

```
Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Arg Ala Val Glu Leu
        595                 600                 605

Gln Ser Leu Val Tyr Phe Leu Lys His Tyr Ser Val Leu Glu Glu Ile
    610                 615                 620

Glu Lys Leu
625
```

<210> SEQ ID NO 125
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 125

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45
```

```
Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Glu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460
```

```
Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Asp
        515                 520                 525

Ile Asn Glu Ser Lys Ile Gly Thr Glu Val Gly Gly Val Pro Val Tyr
    530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Glu Ala Val Glu Leu
        595                 600                 605

Gln Ser Leu Val Tyr Phe Leu Lys His Tyr Ser Val Leu Glu Glu Ile
    610                 615                 620

Glu Lys Leu
625
```

<210> SEQ ID NO 126
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 126

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190
```

```
Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Tyr Asn Ser Asp Asn Val Tyr
                245                 250                 255

Ile Met Ala Asp Lys Gln Lys Asn Gly Ile Lys Ala Asn Phe Lys Ile
            260                 265                 270

Arg His Asn Val Glu Asp Gly Ser Val Gln Leu Ala Asp His Tyr Gln
        275                 280                 285

Gln Asn Thr Pro Ile Gly Asp Gly Pro Val Leu Leu Pro Asp Asn His
    290                 295                 300

Tyr Leu Ser Phe Gln Ser Val Leu Ser Lys Asp Pro Asn Glu Lys Arg
305                 310                 315                 320

Asp His Met Val Leu Leu Glu Phe Val Thr Ala Ala Gly Ile Thr Leu
                325                 330                 335

Gly Met Asp Glu Leu Tyr Asn Val Asp Gly Gly Ser Gly Gly Thr Gly
            340                 345                 350

Ser Lys Gly Glu Glu Leu Phe Thr Gly Val Val Pro Ile Leu Val Glu
        355                 360                 365

Leu Asp Gly Asp Val Asn Gly His Lys Phe Ser Val Ser Gly Glu Gly
    370                 375                 380

Glu Gly Asp Ala Thr Tyr Gly Lys Leu Thr Leu Lys Leu Ile Cys Thr
385                 390                 395                 400

Thr Gly Lys Leu Pro Val Pro Trp Pro Thr Leu Val Thr Thr Leu Gly
                405                 410                 415

Tyr Gly Leu Lys Cys Phe Ala Arg Tyr Pro Asp His Met Lys Gln His
            420                 425                 430

Asp Phe Phe Lys Ser Ala Met Pro Glu Gly Tyr Val Gln Glu Arg Thr
        435                 440                 445

Ile Phe Phe Lys Asp Asp Gly Asn Tyr Lys Thr Arg Ala Glu Val Lys
    450                 455                 460

Phe Glu Gly Asp Thr Leu Val Asn Arg Ile Glu Leu Lys Gly Ile Gly
465                 470                 475                 480

Phe Lys Glu Asp Gly Asn Ile Leu Gly His Lys Leu Glu Tyr Asn Gly
                485                 490                 495

Thr Met Thr Asp Val Ile Leu Ile Gly Val Gly Asn Leu Gly Thr Ala
            500                 505                 510

Phe Leu His Tyr Asn Phe Thr Lys Asn Asn Asn Thr Lys Ile Ser Met
        515                 520                 525

Ala Phe Asp Ile Asn Glu Ser Lys Ile Gly Thr Glu Val Gly Gly Val
    530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
```

610 615 620

Glu Glu Ile Glu Lys Leu
625 630

<210> SEQ ID NO 127
<211> LENGTH: 463
<212> TYPE: PRT
<213> ORGANISM: artificial sequence
<220> FEATURE:
<223> OTHER INFORMATION: Synthetic fluorescent sensor, mutant

<400> SEQUENCE: 127

Met Lys Val Pro Glu Ala Ala Ile Ser Arg Leu Ile Thr Tyr Leu Arg
1 5 10 15

Ile Leu Glu Glu Leu Glu Ala Gln Gly Val His Arg Thr Ser Ser Glu
20 25 30

Gln Leu Gly Glu Leu Ala Gln Val Thr Ala Phe Gln Val Arg Lys Asp
35 40 45

Leu Ser Tyr Phe Gly Ser Tyr Gly Thr Arg Gly Val Gly Tyr Thr Val
50 55 60

Pro Val Leu Lys Arg Glu Leu Arg His Ile Leu Gly Leu Asn Arg Lys
65 70 75 80

Trp Gly Leu Cys Ile Val Gly Met Gly Arg Leu Gly Ser Ala Leu Ala
85 90 95

Asp Tyr Pro Gly Phe Gly Glu Ser Phe Glu Leu Arg Gly Phe Phe Asp
100 105 110

Val Asp Pro Glu Lys Val Gly Arg Pro Val Arg Gly Gly Val Ile Glu
115 120 125

His Val Asp Leu Leu Pro Gln Arg Val Pro Gly Arg Ile Glu Ile Ala
130 135 140

Leu Leu Thr Val Pro Arg Glu Ala Ala Gln Lys Ala Ala Asp Leu Leu
145 150 155 160

Val Ala Ala Gly Ile Lys Gly Ile Leu Asn Phe Ala Pro Val Val Leu
165 170 175

Glu Val Pro Lys Glu Val Ala Val Glu Asn Val Asp Phe Ser Ala Gly
180 185 190

Tyr Asn Ser Asp Asn Val Tyr Ile Met Ala Asp Lys Gln Lys Asn Gly
195 200 205

Ile Lys Ala Asn Phe Lys Ile Arg His Asn Val Glu Asp Gly Ser Val
210 215 220

Gln Leu Ala Asp His Tyr Gln Gln Asn Thr Pro Ile Gly Asp Gly Pro
225 230 235 240

Val Leu Leu Pro Asp Asn His Tyr Leu Ser Phe Gln Ser Val Leu Ser
245 250 255

Lys Asp Pro Asn Glu Lys Arg Asp His Met Val Leu Leu Glu Phe Val
260 265 270

Thr Ala Ala Gly Ile Thr Leu Gly Met Asp Glu Leu Tyr Asn Val Asp
275 280 285

Gly Gly Ser Gly Gly Thr Gly Ser Lys Gly Glu Glu Leu Phe Thr Gly
290 295 300

Val Val Pro Ile Leu Val Glu Leu Asp Gly Asp Val Asn Gly His Lys
305 310 315 320

Phe Ser Val Ser Gly Glu Gly Glu Gly Asp Ala Thr Tyr Gly Lys Leu
325 330 335

Thr Leu Lys Leu Ile Cys Thr Thr Gly Lys Leu Pro Val Pro Trp Pro

```
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Gly Thr Gly Leu Ala Gly Leu Thr Arg Leu
        435                 440                 445

Ser Phe Ala Ile Leu Asn Pro Lys Trp Arg Glu Glu Met Met Gly
    450                 455                 460


<210> SEQ ID NO 128
<211> LENGTH: 462
<212> TYPE: PRT
<213> ORGANISM: artificial sequence
<220> FEATURE:
<223> OTHER INFORMATION: Synthetic fluorescent sensor, mutant

<400> SEQUENCE: 128

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
            180                 185                 190

Asn Ser Asp Asn Val Tyr Ile Met Ala Asp Lys Gln Lys Asn Gly Ile
        195                 200                 205

Lys Ala Asn Phe Lys Ile Arg His Asn Val Glu Asp Gly Ser Val Gln
    210                 215                 220

Leu Ala Asp His Tyr Gln Gln Asn Thr Pro Ile Gly Asp Gly Pro Val
225                 230                 235                 240

Leu Leu Pro Asp Asn His Tyr Leu Ser Phe Gln Ser Val Leu Ser Lys
```

```
                245                 250                 255

Asp Pro Asn Glu Lys Arg Asp His Met Val Leu Leu Glu Phe Val Thr
            260                 265                 270

Ala Ala Gly Ile Thr Leu Gly Met Asp Glu Leu Tyr Asn Val Asp Gly
        275                 280                 285

Gly Ser Gly Gly Thr Gly Ser Lys Gly Glu Glu Leu Phe Thr Gly Val
    290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
            340                 345                 350

Leu Val Thr Thr Leu Gly Tyr Gly Leu Lys Cys Phe Ala Arg Tyr Pro
        355                 360                 365

Asp His Met Lys Gln His Asp Phe Phe Lys Ser Ala Met Pro Glu Gly
    370                 375                 380

Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
            420                 425                 430

Lys Leu Glu Tyr Asn Gly Thr Gly Leu Ala Gly Leu Thr Arg Leu Ser
        435                 440                 445

Phe Ala Ile Leu Asn Pro Lys Trp Arg Glu Glu Met Met Gly
    450                 455                 460


<210> SEQ ID NO 129
<211> LENGTH: 461
<212> TYPE: PRT
<213> ORGANISM: artificial sequence
<220> FEATURE:
<223> OTHER INFORMATION: Synthetic fluorescent sensor, mutant

<400> SEQUENCE: 129

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
```

```
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
        355                 360                 365

His Met Lys Gln His Asp Phe Phe Lys Ser Ala Met Pro Glu Gly Tyr
    370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415

Leu Lys Gly Ile Gly Phe Lys Glu Asp Gly Asn Ile Leu Gly His Lys
            420                 425                 430

Leu Glu Tyr Asn Gly Thr Gly Leu Ala Gly Leu Thr Arg Leu Ser Phe
        435                 440                 445

Ala Ile Leu Asn Pro Lys Trp Arg Glu Glu Met Met Gly
    450                 455                 460


<210> SEQ ID NO 130
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 130

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
```

```
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
        195                 200                 205

Asn Phe Lys Ile Arg His Asn Val Glu Asp Gly Ser Val Gln Leu Ala
    210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
                245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
        275                 280                 285

Gly Gly Thr Gly Ser Lys Gly Glu Glu Leu Phe Thr Gly Val Val Pro
    290                 295                 300

Ile Leu Val Glu Leu Asp Gly Asp Val Asn Gly His Lys Phe Ser Val
305                 310                 315                 320

Ser Gly Glu Gly Glu Gly Asp Ala Thr Tyr Gly Lys Leu Thr Leu Lys
                325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
        355                 360                 365

Met Lys Gln His Asp Phe Phe Lys Ser Ala Met Pro Glu Gly Tyr Val
    370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
                405                 410                 415

Lys Gly Ile Gly Phe Lys Glu Asp Gly Asn Ile Leu Gly His Lys Leu
            420                 425                 430

Glu Tyr Asn Gly Thr Gly Leu Ala Gly Leu Thr Arg Leu Ser Phe Ala
        435                 440                 445

Ile Leu Asn Pro Lys Trp Arg Glu Glu Met Met Gly
    450                 455                 460
```

<210> SEQ ID NO 131

<211> LENGTH: 462
<212> TYPE: PRT
<213> ORGANISM: artificial sequence
<220> FEATURE:
<223> OTHER INFORMATION: Synthetic fluorescent sensor, mutant

<400> SEQUENCE: 131

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380
```

```
Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Gly Thr Leu Ala Gly Leu Thr Arg Leu Ser
        435                 440                 445

Phe Ala Ile Leu Asn Pro Lys Trp Arg Glu Glu Met Met Gly
    450                 455                 460


<210> SEQ ID NO 132
<211> LENGTH: 461
<212> TYPE: PRT
<213> ORGANISM: artificial sequence
<220> FEATURE:
<223> OTHER INFORMATION: Synthetic fluorescent sensor, mutant

<400> SEQUENCE: 132

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285
```

```
Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Gly Leu Ala Gly Leu Thr Arg Leu Ser Phe
        435                 440                 445

Ala Ile Leu Asn Pro Lys Trp Arg Glu Glu Met Met Gly
    450                 455                 460
```

<210> SEQ ID NO 133
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 133

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190
```

```
Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Leu Ala Gly Leu Thr Arg Leu Ser Phe Ala
        435                 440                 445

Ile Leu Asn Pro Lys Trp Arg Glu Glu Met Met Gly
    450                 455                 460


<210> SEQ ID NO 134
<211> LENGTH: 461
<212> TYPE: PRT
<213> ORGANISM: artificial sequence
<220> FEATURE:
<223> OTHER INFORMATION: Synthetic fluorescent sensor, mutant

<400> SEQUENCE: 134

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95
```

```
Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
            180                 185                 190

Asn Ser Asp Asn Val Tyr Ile Met Ala Asp Lys Gln Lys Asn Gly Ile
        195                 200                 205

Lys Ala Asn Phe Lys Ile Arg His Asn Val Glu Asp Gly Ser Val Gln
    210                 215                 220

Leu Ala Asp His Tyr Gln Gln Asn Thr Pro Ile Gly Asp Gly Pro Val
225                 230                 235                 240

Leu Leu Pro Asp Asn His Tyr Leu Ser Phe Gln Ser Val Leu Ser Lys
                245                 250                 255

Asp Pro Asn Glu Lys Arg Asp His Met Val Leu Leu Glu Phe Val Thr
            260                 265                 270

Ala Ala Gly Ile Thr Leu Gly Met Asp Glu Leu Tyr Asn Val Asp Gly
        275                 280                 285

Gly Ser Gly Gly Thr Gly Ser Lys Gly Glu Glu Leu Phe Thr Gly Val
    290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
            340                 345                 350

Leu Val Thr Thr Leu Gly Tyr Gly Leu Lys Cys Phe Ala Arg Tyr Pro
        355                 360                 365

Asp His Met Lys Gln His Asp Phe Phe Lys Ser Ala Met Pro Glu Gly
    370                 375                 380

Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
            420                 425                 430

Lys Leu Glu Tyr Asn Gly Thr Leu Ala Gly Leu Thr Arg Leu Ser Phe
        435                 440                 445

Ala Ile Leu Asn Pro Lys Trp Arg Glu Glu Met Met Gly
    450                 455                 460
```

<210> SEQ ID NO 135
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 135

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
        355                 360                 365

His Met Lys Gln His Asp Phe Phe Lys Ser Ala Met Pro Glu Gly Tyr
    370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415
```

```
Leu Lys Gly Ile Gly Phe Lys Glu Asp Gly Asn Ile Leu Gly His Lys
            420                 425                 430

Leu Glu Tyr Asn Gly Thr Leu Ala Gly Leu Thr Arg Leu Ser Phe Ala
        435                 440                 445

Ile Leu Asn Pro Lys Trp Arg Glu Glu Met Met Gly
    450                 455                 460


<210> SEQ ID NO 136
<211> LENGTH: 459
<212> TYPE: PRT
<213> ORGANISM: artificial sequence
<220> FEATURE:
<223> OTHER INFORMATION: Synthetic fluorescent sensor, mutant

<400> SEQUENCE: 136

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
        195                 200                 205

Asn Phe Lys Ile Arg His Asn Val Glu Asp Gly Ser Val Gln Leu Ala
    210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
                245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
        275                 280                 285

Gly Gly Thr Gly Ser Lys Gly Glu Glu Leu Phe Thr Gly Val Val Pro
    290                 295                 300

Ile Leu Val Glu Leu Asp Gly Asp Val Asn Gly His Lys Phe Ser Val
305                 310                 315                 320
```

```
Ser Gly Glu Gly Glu Gly Asp Ala Thr Tyr Gly Lys Leu Thr Leu Lys
                325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
        355                 360                 365

Met Lys Gln His Asp Phe Phe Lys Ser Ala Met Pro Glu Gly Tyr Val
    370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
                405                 410                 415

Lys Gly Ile Gly Phe Lys Glu Asp Gly Asn Ile Leu Gly His Lys Leu
            420                 425                 430

Glu Tyr Asn Gly Thr Leu Ala Gly Leu Thr Arg Leu Ser Phe Ala Ile
        435                 440                 445

Leu Asn Pro Lys Trp Arg Glu Glu Met Met Gly
    450                 455


<210> SEQ ID NO 137
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 137

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
            180                 185                 190

Asn Ser Asp Asn Val Tyr Ile Met Ala Asp Lys Gln Lys Asn Gly Ile
        195                 200                 205

Lys Ala Asn Phe Lys Ile Arg His Asn Val Glu Asp Gly Ser Val Gln
    210                 215                 220
```

```
Leu Ala Asp His Tyr Gln Gln Asn Thr Pro Ile Gly Asp Gly Pro Val
225                 230                 235                 240

Leu Leu Pro Asp Asn His Tyr Leu Ser Phe Gln Ser Val Leu Ser Lys
                245                 250                 255

Asp Pro Asn Glu Lys Arg Asp His Met Val Leu Leu Glu Phe Val Thr
            260                 265                 270

Ala Ala Gly Ile Thr Leu Gly Met Asp Glu Leu Tyr Asn Val Asp Gly
        275                 280                 285

Gly Ser Gly Gly Thr Gly Ser Lys Gly Glu Glu Leu Phe Thr Gly Val
    290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
            340                 345                 350

Leu Val Thr Thr Leu Gly Tyr Gly Leu Lys Cys Phe Ala Arg Tyr Pro
        355                 360                 365

Asp His Met Lys Gln His Asp Phe Phe Lys Ser Ala Met Pro Glu Gly
    370                 375                 380

Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
            420                 425                 430

Lys Leu Glu Tyr Asn Gly Leu Ala Gly Leu Thr Arg Leu Ser Phe Ala
        435                 440                 445

Ile Leu Asn Pro Lys Trp Arg Glu Glu Met Met Gly
    450                 455                 460


<210> SEQ ID NO 138
<211> LENGTH: 459
<212> TYPE: PRT
<213> ORGANISM: artificial sequence
<220> FEATURE:
<223> OTHER INFORMATION: Synthetic fluorescent sensor, mutant

<400> SEQUENCE: 138

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125
```

```
His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
        355                 360                 365

His Met Lys Gln His Asp Phe Phe Lys Ser Ala Met Pro Glu Gly Tyr
    370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415

Leu Lys Gly Ile Gly Phe Lys Glu Asp Gly Asn Ile Leu Gly His Lys
            420                 425                 430

Leu Glu Tyr Asn Gly Leu Ala Gly Leu Thr Arg Leu Ser Phe Ala Ile
        435                 440                 445

Leu Asn Pro Lys Trp Arg Glu Glu Met Met Gly
    450                 455
```

<210> SEQ ID NO 139
<211> LENGTH: 458
<212> TYPE: PRT
<213> ORGANISM: artificial sequence
<220> FEATURE:
<223> OTHER INFORMATION: Synthetic fluorescent sensor, mutant

<400> SEQUENCE: 139

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30
```

```
Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
        195                 200                 205

Asn Phe Lys Ile Arg His Asn Val Glu Asp Gly Ser Val Gln Leu Ala
    210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
                245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
        275                 280                 285

Gly Gly Thr Gly Ser Lys Gly Glu Glu Leu Phe Thr Gly Val Val Pro
    290                 295                 300

Ile Leu Val Glu Leu Asp Gly Asp Val Asn Gly His Lys Phe Ser Val
305                 310                 315                 320

Ser Gly Glu Gly Glu Gly Asp Ala Thr Tyr Gly Lys Leu Thr Leu Lys
                325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
        355                 360                 365

Met Lys Gln His Asp Phe Phe Lys Ser Ala Met Pro Glu Gly Tyr Val
    370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
                405                 410                 415

Lys Gly Ile Gly Phe Lys Glu Asp Gly Asn Ile Leu Gly His Lys Leu
            420                 425                 430

Glu Tyr Asn Gly Leu Ala Gly Leu Thr Arg Leu Ser Phe Ala Ile Leu
        435                 440                 445

Asn Pro Lys Trp Arg Glu Glu Met Met Gly
```

450 455

<210> SEQ ID NO 140
<211> LENGTH: 459
<212> TYPE: PRT
<213> ORGANISM: artificial sequence
<220> FEATURE:
<223> OTHER INFORMATION: Synthetic fluorescent sensor, mutant

<400> SEQUENCE: 140

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
            180                 185                 190

Asn Ser Asp Asn Val Tyr Ile Met Ala Asp Lys Gln Lys Asn Gly Ile
        195                 200                 205

Lys Ala Asn Phe Lys Ile Arg His Asn Val Glu Asp Gly Ser Val Gln
    210                 215                 220

Leu Ala Asp His Tyr Gln Gln Asn Thr Pro Ile Gly Asp Gly Pro Val
225                 230                 235                 240

Leu Leu Pro Asp Asn His Tyr Leu Ser Phe Gln Ser Val Leu Ser Lys
                245                 250                 255

Asp Pro Asn Glu Lys Arg Asp His Met Val Leu Leu Glu Phe Val Thr
            260                 265                 270

Ala Ala Gly Ile Thr Leu Gly Met Asp Glu Leu Tyr Asn Val Asp Gly
        275                 280                 285

Gly Ser Gly Gly Thr Gly Ser Lys Gly Glu Glu Leu Phe Thr Gly Val
    290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
            340                 345                 350

Leu Val Thr Thr Leu Gly Tyr Gly Leu Lys Cys Phe Ala Arg Tyr Pro
```

```
        355                 360                 365

Asp His Met Lys Gln His Asp Phe Phe Lys Ser Ala Met Pro Glu Gly
    370                 375                 380

Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
            420                 425                 430

Lys Leu Glu Tyr Asn Leu Ala Gly Leu Thr Arg Leu Ser Phe Ala Ile
        435                 440                 445

Leu Asn Pro Lys Trp Arg Glu Glu Met Met Gly
    450                 455


<210> SEQ ID NO 141
<211> LENGTH: 458
<212> TYPE: PRT
<213> ORGANISM: artificial sequence
<220> FEATURE:
<223> OTHER INFORMATION: Synthetic fluorescent sensor, mutant

<400> SEQUENCE: 141

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
```

```
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
        355                 360                 365

His Met Lys Gln His Asp Phe Phe Lys Ser Ala Met Pro Glu Gly Tyr
    370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415

Leu Lys Gly Ile Gly Phe Lys Glu Asp Gly Asn Ile Leu Gly His Lys
            420                 425                 430

Leu Glu Tyr Asn Leu Ala Gly Leu Thr Arg Leu Ser Phe Ala Ile Leu
        435                 440                 445

Asn Pro Lys Trp Arg Glu Glu Met Met Gly
    450                 455


<210> SEQ ID NO 142
<211> LENGTH: 457
<212> TYPE: PRT
<213> ORGANISM: artificial sequence
<220> FEATURE:
<223> OTHER INFORMATION: Synthetic fluorescent sensor, mutant

<400> SEQUENCE: 142

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
```

```
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
        195                 200                 205

Asn Phe Lys Ile Arg His Asn Val Glu Asp Gly Ser Val Gln Leu Ala
    210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
                245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
        275                 280                 285

Gly Gly Thr Gly Ser Lys Gly Glu Glu Leu Phe Thr Gly Val Val Pro
    290                 295                 300

Ile Leu Val Glu Leu Asp Gly Asp Val Asn Gly His Lys Phe Ser Val
305                 310                 315                 320

Ser Gly Glu Gly Glu Gly Asp Ala Thr Tyr Gly Lys Leu Thr Leu Lys
                325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
        355                 360                 365

Met Lys Gln His Asp Phe Phe Lys Ser Ala Met Pro Glu Gly Tyr Val
    370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
                405                 410                 415

Lys Gly Ile Gly Phe Lys Glu Asp Gly Asn Ile Leu Gly His Lys Leu
            420                 425                 430

Glu Tyr Asn Leu Ala Gly Leu Thr Arg Leu Ser Phe Ala Ile Leu Asn
        435                 440                 445

Pro Lys Trp Arg Glu Glu Met Met Gly
    450                 455


<210> SEQ ID NO 143
<211> LENGTH: 387
<212> TYPE: PRT
<213> ORGANISM: artificial sequence
<220> FEATURE:
<223> OTHER INFORMATION: Synthetic fluorescent sensor, mutant

<400> SEQUENCE: 143

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
```

```
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
        115                 120                 125

Gln Lys Asn Gly Ile Lys Ala Asn Phe Lys Ile Arg His Asn Val Glu
    130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
        195                 200                 205

Tyr Asn Val Asp Gly Gly Ser Gly Gly Thr Gly Ser Lys Gly Glu Glu
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
        275                 280                 285

Phe Ala Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
            340                 345                 350

Asn Ile Leu Gly His Lys Leu Glu Tyr Asn Gly Thr Gly Leu Ala Gly
        355                 360                 365

Leu Thr Arg Leu Ser Phe Ala Ile Leu Asn Pro Lys Trp Arg Glu Glu
    370                 375                 380

Met Met Gly
385


<210> SEQ ID NO 144
<211> LENGTH: 386
<212> TYPE: PRT
<213> ORGANISM: artificial sequence
<220> FEATURE:
<223> OTHER INFORMATION: Synthetic fluorescent sensor, mutant

<400> SEQUENCE: 144

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
```

```
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190

Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335

Val Asn Arg Ile Glu Leu Lys Gly Ile Gly Phe Lys Glu Asp Gly Asn
            340                 345                 350

Ile Leu Gly His Lys Leu Glu Tyr Asn Gly Thr Gly Leu Ala Gly Leu
        355                 360                 365

Thr Arg Leu Ser Phe Ala Ile Leu Asn Pro Lys Trp Arg Glu Glu Met
    370                 375                 380

Met Gly
385
```

<210> SEQ ID NO 145
<211> LENGTH: 385
<212> TYPE: PRT
<213> ORGANISM: artificial sequence
<220> FEATURE:
<223> OTHER INFORMATION: Synthetic fluorescent sensor, mutant

<400> SEQUENCE: 145

```
Met Asn Arg Lys Trp Gly Leu Cys Ile Val Gly Met Gly Arg Leu Gly
```

```
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Gly Tyr Asn Ser Asp Asn Val Tyr Ile Met Ala Asp Lys Gln Lys
        115                 120                 125

Asn Gly Ile Lys Ala Asn Phe Lys Ile Arg His Asn Val Glu Asp Gly
    130                 135                 140

Ser Val Gln Leu Ala Asp His Tyr Gln Gln Asn Thr Pro Ile Gly Asp
145                 150                 155                 160

Gly Pro Val Leu Leu Pro Asp Asn His Tyr Leu Ser Phe Gln Ser Val
                165                 170                 175

Leu Ser Lys Asp Pro Asn Glu Lys Arg Asp His Met Val Leu Leu Glu
            180                 185                 190

Phe Val Thr Ala Ala Gly Ile Thr Leu Gly Met Asp Glu Leu Tyr Asn
        195                 200                 205

Val Asp Gly Gly Ser Gly Gly Thr Gly Ser Lys Gly Glu Glu Leu Phe
    210                 215                 220

Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
                245                 250                 255

Lys Leu Thr Leu Lys Leu Ile Cys Thr Thr Gly Lys Leu Pro Val Pro
            260                 265                 270

Trp Pro Thr Leu Val Thr Thr Leu Gly Tyr Gly Leu Lys Cys Phe Ala
        275                 280                 285

Arg Tyr Pro Asp His Met Lys Gln His Asp Phe Phe Lys Ser Ala Met
    290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Gly Thr Gly Leu Ala Gly Leu Thr
        355                 360                 365

Arg Leu Ser Phe Ala Ile Leu Asn Pro Lys Trp Arg Glu Glu Met Met
    370                 375                 380

Gly
385
```

<210> SEQ ID NO 146
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 146

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Gly Thr Gly Leu Ala Gly Leu Thr Arg
        355                 360                 365

Leu Ser Phe Ala Ile Leu Asn Pro Lys Trp Arg Glu Glu Met Met Gly
    370                 375                 380
```

<210> SEQ ID NO 147

<211> LENGTH: 386
<212> TYPE: PRT
<213> ORGANISM: artificial sequence
<220> FEATURE:
<223> OTHER INFORMATION: Synthetic fluorescent sensor, mutant

<400> SEQUENCE: 147

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
        115                 120                 125

Gln Lys Asn Gly Ile Lys Ala Asn Phe Lys Ile Arg His Asn Val Glu
    130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
        195                 200                 205

Tyr Asn Val Asp Gly Gly Ser Gly Gly Thr Gly Ser Lys Gly Glu Glu
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
        275                 280                 285

Phe Ala Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
            340                 345                 350

Asn Ile Leu Gly His Lys Leu Glu Tyr Asn Gly Thr Leu Ala Gly Leu
        355                 360                 365

Thr Arg Leu Ser Phe Ala Ile Leu Asn Pro Lys Trp Arg Glu Glu Met
    370                 375                 380
```

```
Met Gly
385


<210> SEQ ID NO 148
<211> LENGTH: 385
<212> TYPE: PRT
<213> ORGANISM: artificial sequence
<220> FEATURE:
<223> OTHER INFORMATION: Synthetic fluorescent sensor, mutant

<400> SEQUENCE: 148

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
        115                 120                 125

Gln Lys Asn Gly Ile Lys Ala Asn Phe Lys Ile Arg His Asn Val Glu
    130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
        195                 200                 205

Tyr Asn Val Asp Gly Gly Ser Gly Gly Thr Gly Ser Lys Gly Glu Glu
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
        275                 280                 285

Phe Ala Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
            340                 345                 350
```

```
Asn Ile Leu Gly His Lys Leu Glu Tyr Asn Gly Leu Ala Gly Leu Thr
        355                 360                 365

Arg Leu Ser Phe Ala Ile Leu Asn Pro Lys Trp Arg Glu Glu Met Met
    370                 375                 380

Gly
385


<210> SEQ ID NO 149
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 149

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
        115                 120                 125

Gln Lys Asn Gly Ile Lys Ala Asn Phe Lys Ile Arg His Asn Val Glu
    130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
        195                 200                 205

Tyr Asn Val Asp Gly Gly Ser Gly Gly Thr Gly Ser Lys Gly Glu Glu
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
        275                 280                 285

Phe Ala Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320
```

```
Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
            340                 345                 350

Asn Ile Leu Gly His Lys Leu Glu Tyr Asn Leu Ala Gly Leu Thr Arg
        355                 360                 365

Leu Ser Phe Ala Ile Leu Asn Pro Lys Trp Arg Glu Glu Met Met Gly
    370                 375                 380


<210> SEQ ID NO 150
<211> LENGTH: 385
<212> TYPE: PRT
<213> ORGANISM: artificial sequence
<220> FEATURE:
<223> OTHER INFORMATION: Synthetic fluorescent sensor, mutant

<400> SEQUENCE: 150

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190

Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300
```

Met Pro Glu Gly Tyr Val Gln Glu Arg Thr Ile Phe Phe Lys Asp Asp
305 310 315 320

Gly Asn Tyr Lys Thr Arg Ala Glu Val Lys Phe Glu Gly Asp Thr Leu
325 330 335

Val Asn Arg Ile Glu Leu Lys Gly Ile Gly Phe Lys Glu Asp Gly Asn
340 345 350

Ile Leu Gly His Lys Leu Glu Tyr Asn Gly Thr Leu Ala Gly Leu Thr
355 360 365

Arg Leu Ser Phe Ala Ile Leu Asn Pro Lys Trp Arg Glu Glu Met Met
370 375 380

Gly
385

<210> SEQ ID NO 151
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 151

Met Asn Arg Lys Trp Gly Leu Cys Ile Val Gly Met Gly Arg Leu Gly
1 5 10 15

Ser Ala Leu Ala Asp Tyr Pro Gly Phe Gly Glu Ser Phe Glu Leu Arg
20 25 30

Gly Phe Phe Asp Val Asp Pro Glu Lys Val Gly Arg Pro Val Arg Gly
35 40 45

Gly Val Ile Glu His Val Asp Leu Leu Pro Gln Arg Val Pro Gly Arg
50 55 60

Ile Glu Ile Ala Leu Leu Thr Val Pro Arg Glu Ala Ala Gln Lys Ala
65 70 75 80

Ala Asp Leu Leu Val Ala Ala Gly Ile Lys Gly Ile Leu Asn Phe Ala
85 90 95

Pro Val Val Leu Glu Val Pro Lys Glu Val Ala Val Glu Asn Val Asp
100 105 110

Phe Gly Tyr Asn Ser Asp Asn Val Tyr Ile Met Ala Asp Lys Gln Lys
115 120 125

Asn Gly Ile Lys Ala Asn Phe Lys Ile Arg His Asn Val Glu Asp Gly
130 135 140

Ser Val Gln Leu Ala Asp His Tyr Gln Gln Asn Thr Pro Ile Gly Asp
145 150 155 160

Gly Pro Val Leu Leu Pro Asp Asn His Tyr Leu Ser Phe Gln Ser Val
165 170 175

Leu Ser Lys Asp Pro Asn Glu Lys Arg Asp His Met Val Leu Leu Glu
180 185 190

Phe Val Thr Ala Ala Gly Ile Thr Leu Gly Met Asp Glu Leu Tyr Asn
195 200 205

Val Asp Gly Gly Ser Gly Gly Thr Gly Ser Lys Gly Glu Glu Leu Phe
210 215 220

Thr Gly Val Val Pro Ile Leu Val Glu Leu Asp Gly Asp Val Asn Gly
225 230 235 240

His Lys Phe Ser Val Ser Gly Glu Gly Glu Gly Asp Ala Thr Tyr Gly
245 250 255

Lys Leu Thr Leu Lys Leu Ile Cys Thr Thr Gly Lys Leu Pro Val Pro
260 265 270

```
Trp Pro Thr Leu Val Thr Thr Leu Gly Tyr Gly Leu Lys Cys Phe Ala
        275                 280                 285

Arg Tyr Pro Asp His Met Lys Gln His Asp Phe Phe Lys Ser Ala Met
    290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Gly Thr Leu Ala Gly Leu Thr Arg
        355                 360                 365

Leu Ser Phe Ala Ile Leu Asn Pro Lys Trp Arg Glu Glu Met Met Gly
    370                 375                 380


<210> SEQ ID NO 152
<211> LENGTH: 383
<212> TYPE: PRT
<213> ORGANISM: artificial sequence
<220> FEATURE:
<223> OTHER INFORMATION: Synthetic fluorescent sensor, mutant

<400> SEQUENCE: 152

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255
```

```
Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Gly Thr Leu Ala Gly Leu Thr Arg Leu
        355                 360                 365

Ser Phe Ala Ile Leu Asn Pro Lys Trp Arg Glu Glu Met Met Gly
    370                 375                 380
```

```
<210> SEQ ID NO 153
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 153
```

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190

Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240
```

```
Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335

Val Asn Arg Ile Glu Leu Lys Gly Ile Gly Phe Lys Glu Asp Gly Asn
            340                 345                 350

Ile Leu Gly His Lys Leu Glu Tyr Asn Gly Leu Ala Gly Leu Thr Arg
        355                 360                 365

Leu Ser Phe Ala Ile Leu Asn Pro Lys Trp Arg Glu Glu Met Met Gly
    370                 375                 380


<210> SEQ ID NO 154
<211> LENGTH: 383
<212> TYPE: PRT
<213> ORGANISM: artificial sequence
<220> FEATURE:
<223> OTHER INFORMATION: Synthetic fluorescent sensor, mutant

<400> SEQUENCE: 154

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Gly Tyr Asn Ser Asp Asn Val Tyr Ile Met Ala Asp Lys Gln Lys
        115                 120                 125

Asn Gly Ile Lys Ala Asn Phe Lys Ile Arg His Asn Val Glu Asp Gly
    130                 135                 140

Ser Val Gln Leu Ala Asp His Tyr Gln Gln Asn Thr Pro Ile Gly Asp
145                 150                 155                 160

Gly Pro Val Leu Leu Pro Asp Asn His Tyr Leu Ser Phe Gln Ser Val
                165                 170                 175

Leu Ser Lys Asp Pro Asn Glu Lys Arg Asp His Met Val Leu Leu Glu
            180                 185                 190

Phe Val Thr Ala Ala Gly Ile Thr Leu Gly Met Asp Glu Leu Tyr Asn
        195                 200                 205

Val Asp Gly Gly Ser Gly Gly Thr Gly Ser Lys Gly Glu Glu Leu Phe
    210                 215                 220
```

```
Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
                245                 250                 255

Lys Leu Thr Leu Lys Leu Ile Cys Thr Thr Gly Lys Leu Pro Val Pro
            260                 265                 270

Trp Pro Thr Leu Val Thr Thr Leu Gly Tyr Gly Leu Lys Cys Phe Ala
        275                 280                 285

Arg Tyr Pro Asp His Met Lys Gln His Asp Phe Phe Lys Ser Ala Met
    290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Gly Leu Ala Gly Leu Thr Arg Leu
        355                 360                 365

Ser Phe Ala Ile Leu Asn Pro Lys Trp Arg Glu Glu Met Met Gly
    370                 375                 380


<210> SEQ ID NO 155
<211> LENGTH: 382
<212> TYPE: PRT
<213> ORGANISM: artificial sequence
<220> FEATURE:
<223> OTHER INFORMATION: Synthetic fluorescent sensor, mutant

<400> SEQUENCE: 155

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205
```

```
Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Gly Leu Ala Gly Leu Thr Arg Leu Ser
        355                 360                 365

Phe Ala Ile Leu Asn Pro Lys Trp Arg Glu Glu Met Met Gly
    370                 375                 380


<210> SEQ ID NO 156
<211> LENGTH: 383
<212> TYPE: PRT
<213> ORGANISM: artificial sequence
<220> FEATURE:
<223> OTHER INFORMATION: Synthetic fluorescent sensor, mutant

<400> SEQUENCE: 156

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190
```

```
Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335

Val Asn Arg Ile Glu Leu Lys Gly Ile Gly Phe Lys Glu Asp Gly Asn
            340                 345                 350

Ile Leu Gly His Lys Leu Glu Tyr Asn Leu Ala Gly Leu Thr Arg Leu
        355                 360                 365

Ser Phe Ala Ile Leu Asn Pro Lys Trp Arg Glu Glu Met Met Gly
    370                 375                 380
```

```
<210> SEQ ID NO 157
<211> LENGTH: 382
<212> TYPE: PRT
<213> ORGANISM: artificial sequence
<220> FEATURE:
<223> OTHER INFORMATION: Synthetic fluorescent sensor, mutant

<400> SEQUENCE: 157

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Gly Tyr Asn Ser Asp Asn Val Tyr Ile Met Ala Asp Lys Gln Lys
        115                 120                 125

Asn Gly Ile Lys Ala Asn Phe Lys Ile Arg His Asn Val Glu Asp Gly
    130                 135                 140

Ser Val Gln Leu Ala Asp His Tyr Gln Gln Asn Thr Pro Ile Gly Asp
145                 150                 155                 160

Gly Pro Val Leu Leu Pro Asp Asn His Tyr Leu Ser Phe Gln Ser Val
                165                 170                 175
```

```
Leu Ser Lys Asp Pro Asn Glu Lys Arg Asp His Met Val Leu Leu Glu
            180                 185                 190

Phe Val Thr Ala Ala Gly Ile Thr Leu Gly Met Asp Glu Leu Tyr Asn
        195                 200                 205

Val Asp Gly Gly Ser Gly Gly Thr Gly Ser Lys Gly Glu Glu Leu Phe
    210                 215                 220

Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
                245                 250                 255

Lys Leu Thr Leu Lys Leu Ile Cys Thr Thr Gly Lys Leu Pro Val Pro
            260                 265                 270

Trp Pro Thr Leu Val Thr Thr Leu Gly Tyr Gly Leu Lys Cys Phe Ala
        275                 280                 285

Arg Tyr Pro Asp His Met Lys Gln His Asp Phe Phe Lys Ser Ala Met
    290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Leu Ala Gly Leu Thr Arg Leu Ser
        355                 360                 365

Phe Ala Ile Leu Asn Pro Lys Trp Arg Glu Glu Met Met Gly
    370                 375                 380
```

<210> SEQ ID NO 158
<211> LENGTH: 381
<212> TYPE: PRT
<213> ORGANISM: artificial sequence
<220> FEATURE:
<223> OTHER INFORMATION: Synthetic fluorescent sensor, mutant

<400> SEQUENCE: 158

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160
```

```
Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Leu Ala Gly Leu Thr Arg Leu Ser Phe
        355                 360                 365

Ala Ile Leu Asn Pro Lys Trp Arg Glu Glu Met Met Gly
    370                 375                 380


<210> SEQ ID NO 159
<211> LENGTH: 629
<212> TYPE: PRT
<213> ORGANISM: artificial sequence
<220> FEATURE:
<223> OTHER INFORMATION: Synthetic fluorescent sensor, mutant

<400> SEQUENCE: 159

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140
```

```
Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Tyr Asn Ser Asp Asn Val Tyr Ile
                245                 250                 255

Met Ala Asp Lys Gln Lys Asn Gly Ile Lys Ala Asn Phe Lys Ile Arg
            260                 265                 270

His Asn Val Glu Asp Gly Ser Val Gln Leu Ala Asp His Tyr Gln Gln
        275                 280                 285

Asn Thr Pro Ile Gly Asp Gly Pro Val Leu Leu Pro Asp Asn His Tyr
    290                 295                 300

Leu Ser Phe Gln Ser Val Leu Ser Lys Asp Pro Asn Glu Lys Arg Asp
305                 310                 315                 320

His Met Val Leu Leu Glu Phe Val Thr Ala Ala Gly Ile Thr Leu Gly
                325                 330                 335

Met Asp Glu Leu Tyr Asn Val Asp Gly Gly Ser Gly Gly Thr Gly Ser
            340                 345                 350

Lys Gly Glu Glu Leu Phe Thr Gly Val Val Pro Ile Leu Val Glu Leu
        355                 360                 365

Asp Gly Asp Val Asn Gly His Lys Phe Ser Val Ser Gly Glu Gly Glu
    370                 375                 380

Gly Asp Ala Thr Tyr Gly Lys Leu Thr Leu Lys Leu Ile Cys Thr Thr
385                 390                 395                 400

Gly Lys Leu Pro Val Pro Trp Pro Thr Leu Val Thr Thr Leu Gly Tyr
                405                 410                 415

Gly Leu Lys Cys Phe Ala Arg Tyr Pro Asp His Met Lys Gln His Asp
            420                 425                 430

Phe Phe Lys Ser Ala Met Pro Glu Gly Tyr Val Gln Glu Arg Thr Ile
        435                 440                 445

Phe Phe Lys Asp Asp Gly Asn Tyr Lys Thr Arg Ala Glu Val Lys Phe
    450                 455                 460

Glu Gly Asp Thr Leu Val Asn Arg Ile Glu Leu Lys Gly Ile Gly Phe
465                 470                 475                 480

Lys Glu Asp Gly Asn Ile Leu Gly His Lys Leu Glu Tyr Asn Gly Thr
                485                 490                 495

Met Thr Asp Val Ile Leu Ile Gly Val Gly Asn Leu Gly Thr Ala Phe
            500                 505                 510

Leu His Tyr Asn Phe Thr Lys Asn Asn Asn Thr Lys Ile Ser Met Ala
        515                 520                 525

Phe Asp Ile Asn Glu Ser Lys Ile Gly Thr Glu Val Gly Gly Val Pro
    530                 535                 540

Val Tyr Asn Leu Asp Asp Leu Glu Gln His Val Lys Asp Glu Ser Val
545                 550                 555                 560
```

-continued

```
Ala Ile Leu Thr Val Pro Ala Val Ala Ala Gln Ser Ile Thr Asp Arg
                565                 570                 575

Leu Val Ala Leu Gly Ile Lys Gly Ile Leu Asn Phe Thr Pro Ala Arg
            580                 585                 590

Leu Asn Val Pro Glu His Ile Arg Ile His His Ile Asp Leu Ala Val
        595                 600                 605

Glu Leu Gln Ser Leu Val Tyr Phe Leu Lys His Tyr Ser Val Leu Glu
    610                 615                 620

Glu Ile Glu Lys Leu
625
```

NICOTINAMIDE ADENINE DINUCLEOTIDE INDICATORS, METHODS OF PREPARATION AND APPLICATION THEREOF

CROSS-REFERENCE TO RELATED APPLICATIONS

The present application is a divisional of U.S. Ser. No. 14/347,575, which has issued as U.S. Pat. No. 9,606,121 on Mar. 28, 2017, and which is the U.S. National Stage of PCT/CN2012/081977, filed Sep. 26, 2012, which claims the priority benefit of Chinese Application No. 201110288807.6, filed Sep. 26, 2011, incorporated by reference in their entireties herein.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF INVENTION

The invention relates to a sensor for detecting nicotinamide adenine dinucleotide, especially, relates to a recombinant fluorescent fusion protein sensor for detecting nicotinamide adenine dinucleotide. In one specific aspect, this invention relates to a recombinant fluorescent fusion protein sensor for detecting reduced nicotinamide adenine dinucleotide (NADH); in another specific aspect, this invention relates to a recombinant fluorescent fusion protein sensor for detecting oxidized nicotinamide adenine dinucleotide ($NAD^+$); in another aspect, the invention further relates to a recombinant fluorescent fusion protein sensor for detecting the ratio of reduced to oxidized nicotinamide adenine dinucleotide. This invention also relates to a process for preparing the sensors, and uses of the sensors in detecting NADH, $NAD^+$ and NADH/$NAD^+$ ratio.

BACKGROUND OF INVENTION

As coenzymes, $NAD^+$ and NADH are important components of the respiratory chain, and involved in the electron transfer process in the respiratory chain (Rich, P. R. et al., Biochem Soc Trans. 2003, V.31 (6), pp. 1095-1105). In redox reactions of the respiratory chain, $NAD^+$ acts as a proton carrier and transforms from its initial oxidation state to reduction state upon reception of an electron from other molecules; NADH, the product of this transformation, can act as a reducing agent providing electron for other molecules (Belenky. P. et al., Trends in Biochemical Sciences. 2007, V.32 (1), pp. 12-19). Recent studies have shown that, NAD(H) is not only involved in energy metabolism, substance synthesis, and antioxidation, but also relates to, inter alia, in vivo calcium homeostasis, gene expression, immunization, cell ageing and death, wherein NAD(H) plays vital roles. Accordingly, NAD(H) itself and numerous enzymes relating to NAD(H) metabolism have become targets for drug design (Sauve, A. A. et al., J Pharmacol Exp Ther. 2008, V.324(3), pp. 883-893).

However, in most living cells, the total amount of NAD (H) is about $10^{-6}$ M~$10^{-3}$ M, while the $NAD^+$/NADH ratio also varies depending on intracellular states (Lin, S. J. et al., Current Opinion in Cell Biology. 2003, V.15(2), pp. 241-246), therefore, it is difficult to determine NAD(H). Earlier detecting methods mainly utilize the characteristic UV absorption of NADH at 340 nm, which leads to the UV spectrophotometry assay. This method has two main flaws: 1, the effective sensitivity is about $10^{-7}$ M, limited by the instrument precision; 2, effective differentiation between NADH and NADPH is not possible in complicated systems. A series of enzymatic assay are later developed based on the characteristic of $NAD^+$ as a coenzyme which accepts an electron during electron transport and transforms to NADH. Other methods, such as HPLC analysis, the electrochemical assay, capillary electrophoresis, fluorescence imaging, etc., are also commonly reported in literatures. However, most of the methods either lack sensitivity towards target molecules in individual cells or lack capacity for localization to subcellular organelles. It is noteworthy that, a major common defect in these available methods is the need of sample processing including lysis, separation, and purification. As NADH itself is prone to oxidization, and errors are readily introduced, the cumbersome operations would lead to experimental results deviated from the bona fide values. In addition, these existing methods can not be applied to living animals or cells and can not detect in real time, which limits the applications in clinical diagnosis and prodrugs research. At present, NADH detection in living animals or cells can only be achieved by using NADH autofluorescence (Zhang, Q. H. et al., Science. 2002, V.295 (5561), pp. 1895-1897), but this traditional method has serious flaws as follows: first, it is known that the regulations of $NAD^+$/NADH and $NADP^+$/NADPH in cells are relatively independent, normally, $NAD^+$/NADH ratio is about 700:1, while $NADP^+$/NADPH ratio is about 1:200; second, the vast different in redox potential between NADH and NADPH indicates the distinct roles in energy metabolism and anabolism played by them; third, with NADH and NADPH autofluorescence being completely indistinguishable, the result obtained through autofluorescence imaging measurement is the sum of NADH and NADPH, and the data essentially indicates the concentration of protein-bound NADPH instead because the content of NADPH is low and mostly presented in protein binding form (Zhang, Q. H. et al., Science. 2002, V.295 (5561), pp. 1895-1897); fourth, since NADH is excited with wavelength in the ultraviolet range (340 nm) and its autofluorescence is weak, sophisticated and expensive equipments such as CritiView for clinical monitoring are required; furthermore, UV light has a rather weak capability of penetrating through tissues and can cause cell damages, so these optical properties severely restrict the application of autofluorescence monitoring.

Therefore, there is an urgent need in the art to develop a specific NADH detecting technique, especially, a specific technique which is suitable for detecting NADH in physiological level and subcellular level.

Relative to traditional detection techniques involving small molecule dye and rapid developing detection techniques using quantom dot, fluorescent protein detection technique has a unique overwhelming advantage in the imaging of most living cells; fluorescent protein can be genetically introduced into cells, tissues, and even whole organs, therefore it can be used as a whole-cell marker or gene activation indicator.

Green fluorescent protein is originally isolated from *Aequorea victoria*, and the wild-type AvGFP is consisted of 238 amino acids and has a molecular weight of about 26 kD. Recent study confirms that, in native GFP protein, three amino acids from 65 to 67, Ser-Tyr-Gly, are able to spontaneously form a fluorescent chromogenic moiety, wherein p-hydroxy-benzylidene-imidazolinone is the main luminous feature. The wild-type AvGFP has rather complex spectral characteristics with its main fluorescent excitation peak at 395 nm, and a secondary peak at 475 nm, whose amplitude intensity is approximately ⅓ of the main peak. Under standard solution condition, 395 nm excitation can produce 508 nm emission, and 475 nm excitation produces maximal emission at 503 nm (Heim, R. et al., Proc Natl Acad Sci USA. 1994, V.91 (26), pp. 12501-12504).

Upon intensive studies on GFP protein mutations, a variety of prominent GFP derivatives have been developed using molecular biotechnology. Through various single-point mutations or combination thereof made to the wild-type GFP, mutants such as enhanced-type GFP (S65T, F64L), YFP (T203Y) and CFP (Y66W) can be obtained. By rearranging GFP protein sequence to shift the original amino acids 145-238 to the N terminal and the amino acids 1-144 to the C terminal of the new protein, and binding the two fragments through a flexible short peptide chain, a space sensitive circular permutation fluorescent protein is formed thereby, and a T203Y point mutation thereupon results in a circular permutation yellow fluorescent protein cpYFP (Nagai, T. et al., Proc Natl Acad Sci U.S.A. 2001, V.98 (6), pp. 3197-3202).

Fluorescence-based analytical techniques have further developed along with the progression in fluorescent protein studies. One example is fluorescent resonance energy transfer (FRET) technique that is routinely adopted nowadays, the key mechanism of which is, when two fluorophores are in sufficiently close proximity, a donor entity absorbs photon of suitable frequency and is excited to a higher energy state returns to the ground state upon transferring energy to nearby acceptor entity via dipole-dipole interaction (that is, the occurrence of resonance energy transfer). FRET is a non-radiation energy transfer through intermolecular dipole-dipole interaction transferring energy from donor in excited state to result in acceptor in excited state, so that the fluorescence intensity of the donor decreases while the acceptor may emit characteristic fluorescence (sensitized fluorescence) which is stronger than its basic fluorescence, or it may emit no fluorescence (fluorescence quenching). Further studies of the green fluorescent protein show that cyan fluorescent protein (CFP) and yellow fluorescent protein (YFP) derived from green fluorescent protein mutants constitute a prominent donor/acceptor pair. Emission spectrum of CFP substantially overlaps absorption spectrum of YFP, when CFP and YFP are in sufficiently close proximity and upon the excitation with the absorption wavelength of CFP, the chromophore of CFP will effectively resonance transfer energy to the chromophore of YFP, so CFP emitted fluorescence will be weakened or disappeared, and the main emission is YFP fluorescence. The efficiency of energy transfer between the two chromophores is inversely proportional to sixth power of the spatial distance between them, and is very sensitive to changes in spatial position. Therefore, existing studies report the use of genetically engineering recombinant methods for expression of a novel fusion protein having both termini of the protein of interest fused with CFP and YFP, respectively, such that spatial change caused by binding of the protein with its specific target molecule will be visualized by the fluorescent change.

So the fluorescent protein sequence used herein may come from *Aequorea victoria* fluorescent protein and its derivatives, including, but not limited to sequences of the following mutants: yellow fluorescent protein (YFP), green fluorescent protein (GFP), cyan fluorescent protein (CFP), and the likes, the sequence of yellow fluorescent protein YFP is preferable, and the sequence of circular permutation yellow fluorescent protein cpYFP is particularly preferable.

The technique described herein involves another protein, YdiH protein (also known as Rex protein), a bacterial transcriptional repressor protein already known in the art, which has a molecular weight of 23 kDa and can regulate fermentation and anaerobic respiration. Generally, YdiH proteins are derived from *Thermus aquaticus* (SEQ ID NO: 1 NCBI GenBank: AF061257.1), *Streptomyces coelicolor* (SEQ ID NO: 2 NCBI GenBank: AL9391.1) or *Bacillus subtilis* (SEQ ID NO: 3 NCBI GenBank: AL009126.3). YdiH protein is initially identified in 2003 from *Streptomyces coelicolor* by Brekasis and Paget et al., which is a redox-sensitive regulatory protein that widely presents in Gram-positive bacteria. The study on YdiH (Rex) protein of *Streptomyces coelicolor* indicates that it is a typical NAD(H) binding protein with Rossmann domain. The key Rossmann domain is a super-secondary protein structure mainly exists in nucleotide binding proteins, and it is a typical cofactor NAD(H) binding domain, represented by various cofactor NAD(H) binding proteins. The structure is essentially comprised of 6 β-pleated sheets linked through two pairs of α-helixes in the form of β-α-β-α-β. Since each Rossmann domain can bind one nucleotide molecule only, there are two Rossmann segments presented pairwise in dinucleotide binding proteins such as these for NAD. Current studies have shown that the *Streptomyces coelicolor* YdiH (Rex) protein can directly probe changes in cytoplasmic NADH/$NAD^+$ ratio, while under aerobic conditions, the YdiH (Rex) protein can inhibit the transcription of its target genes (cydABC, nuoA-D and rexhemACD) when intracellular NADH/$NAD^+$ ratio is at low level, but dissociates from its operon region at elevated NADH/$NAD^+$ ratio, and during this dynamic process, the steric configuration of YdiH (Rex) protein transforms upon environmental change (Brekasis, D. et al., EMBO J., 2003, V.22 (18), pp. 4856-4865). Therefore, Rex protein is a good candidate for intracellular NADH sensor. Meanwhile, Wang et al. recently crystallized the *Bacillus subtilis* YdiH (Rex) protein and investigated its mechanism and function. Their results show that YdiH(Rex) protein from *Bacillus subtilis* is a homodimer protein having two functional domains, wherein the N-terminal domain (residues 1-85) is a DNA-binding domain, while the C-terminal domain (residues 86-215) is a typical Rossmann fold that can bind NADH (Wang, E. et al., Mol Microbiol 2008, V.69 (2), pp. 466-478).

Although YdiH (Rex) protein per se is sensitive to the redox state of the environment, the changes thereof are not intuitively exhibited and can not be captured externally. While by means of the fluorescent protein, we can ideally obtain a novel genetically encoded fluorescent sensor by fusioned expression of YdiH (Rex) and fluorescent protein, YdiH (Rex) is utilized for probing environmental redox state change and relaying the change to the fluorescent protein, which will visualize the change in environmental redox state in real-time and intuitively by the presence/absence or the intensity of the fluorescence generated thereby.

In summary, we believe that the use of recombinant fluorescent fusing protein which contains YdiH protein is able to meet the urgent need to detect NADH in physiological level and subcellular level.

The citation or discussion of any reference in this specification should not be construed as an admission that such reference is available as "Prior Art" to the present invention.

SUMMARY OF INVENTION

On one aspect, this invention provides a genetically encoded fluorescent sensor for NADH, comprising a polypeptide which is sensitive to environmental NADH, and a segment that exhibits the environmental NADH by change in its spectral characteristics. In one embodiment, the segment that exhibits the environmental NADH by change in the spectral characteristic is a fluorescent protein sequence or a derivative thereof. In another embodiment, the NADH-sensitive polypeptide is a polypeptide or its functional fragment or NADH binding domains having following characteristics:

(1) comprising Rossman domain with NADH binding feature; and/or (2) derived from an NADH sensitive protein of transcription regulatory factor Rex family.

In a preferred embodiment, the polypeptide sensitive to NADH described herein may have following characteristics:

(1) containing polypeptide derived from bacterial transcription factor Rex protein gene ydiH, wherein the polypeptide may be encoded by a sequence selected from SEQ ID NO: 1, 2 or 3;

(2) a homologous or non-homologous sequence that is 95% identical to the sequence describe in (1) in at least 85 amino acid residues;

(3) any homologous or non-homologous sequence that is 90% identical to the sequence describe in (1) in at least 85 amino acid residues;

(4) any homologous or non-homologous sequence that is 70% identical to the sequence describe in (1) in at least 85 amino acid residues;

(5) any homologous or non-homologous sequence that is 50% identical to the sequence describe in (1) in at least 85 amino acid residues;

(6) any homologous or non-homologous sequence that is 40% identical to the sequence describe in (1) in at least 85 amino acid residues; or (7) any homologous or non-homologous sequence that is 35% identical to the sequence describe in (1) in at least 85 amino acid residues.

In another embodiment, the fluorescent sensor of this invention may contain Rossman domain B characterized by NADH binding property and fluorescent protein sequence A, A1 and/or A2, which may be combined in a form of:

(1) B-A-B;

(2) B-A-B-B;

(3) A1-B-A2, wherein A1 and A2 can be identical or different; A1 can be an amino acid sequence derived from *Aequorea Victoria* fluorescent protein or a derivative thereof, and A2 can be an amino acid sequence derived from another *Aequorea victoria* fluorescent protein or a derivative thereof;

(4) a first portion of B-A-a second portion of B; wherein A is inserted in the flexible region of B such that B is segmented into the first portion and the second portion, while the first portion of B and the second portion of B constitute a complete B domain; or (5) a first portion of B-A-a second portion of B-B; wherein A is inserted in the flexible region of B such that B is segmented into the first portion and the second portion of B, while the first portion of B and the second portion of B constitute a complete B domain.

In yet another embodiment, the fluorescent sensor in this invention may also have the following structure:

$A_1$-$B_1$-$Linker_1$-FM-$Linker_2$-$B_2$, wherein $A_1$ is a first domain of YdiH protein, preferably containing amino acids 1-84 of *Bacillus subtilis* YdiH protein sequence (SEQ ID NO: 14), or amino acids 1-79 of *Thermus aquaticus* YdiH protein sequence (SEQ ID NO: 15), or variant thereof; $B_1$ is a second domain of YdiH protein, preferably containing amino acids 85-194 of *Bacillus subtilis* YdiH protein sequence (SEQ ID NO: 16), or amino acids 80-189 of *Thermus aquaticus* YdiH protein sequence (SEQ ID NO: 17), or variant thereof; $B_2$ is a third domain of YdiH protein, preferably containing amino acids 120-215 of *Bacillus subtilis* YdiH protein sequence (SEQ ID NO: 18), or amino acids 114-211 of *Thermus aquaticus* YdiH protein sequence (SEQ ID NO: 19), or variant thereof;

FM is a fluorophore, and it can be YFP, GFP, CFP and variants derived from these proteins, wherein YFP is preferable, and cpYFP is more preferable;

$Linker_1$ may be present or absent; if present, $Linker_1$ can be any amino acid sequence, preferably not longer than 4 amino acids, for example, it may contain amino acids T, S, A, G, or may be any combination of any 1 to 4 amino acids of them, e.g., amino acid sequence SAG or TS or the likes, but not limited thereto;

$Linker_2$ may be present or absent; if present, $Linker_2$ can be any amino acid sequence, preferably not longer than 3 amino acids, for example, it may contain amino acids G, T, G, or may be any combination of any 1 to 3 amino acids of them, e.g., amino acid sequence GTG, but not limited thereto.

In one embodiment, this invention also provides a fluorescent sensor containing a fluorophore, and a YdiH protein or any one of protein fragments, derivatives or analogs of YdiH. In another embodiment, the invention also provides a fluorescent sensor containing a fluorophore and a YdiH protein variant. The invention also provides a fluorescent sensor containing a fluorophore and a soluble fragment of YdiH protein.

In one embodiment, this invention provides a fluorescent sensor comprising the amino acid sequence of SEQ ID NO: 4, 5, 6, 7 or 8. In a preferred embodiment, this invention provides a fluorescent sensor comprising a homologous and non-homologous sequence having 99%, 95%, 90%, 80%, 70% or 50% identity with amino acid sequence SEQ ID NO: 4, 5, 6, 7 or 8 in at least 85 amino acid residues. In a preferred embodiment, this invention provides a fluorescent sensor comprising a homologous or non-homologous sequence that is substantially similar or identical to amino acid sequence SEQ ID NO: 4, 5, 6, 7 or 8 in at least 85 amino acid residues. In a preferred embodiment, this invention provides a fluorescent sensor comprising a mutant or derivative of amino acid sequence SEQ ID NO: 4, 5, 6, 7 or 8.

In another embodiment, the invention also provides a genetically encoded fluorescent sensor for $NAD^+$, comprising a polypeptide which is sensitive to environmental $NAD^+$, and a segment that exhibits the environmental $NAD^+$ by change in its spectral characteristics. In a specific embodiment, the fluorescent sensor for $NAD^+$ comprises SEQ ID NO: 129.

In another embodiment, the invention also provides a genetically encoded fluorescent sensor for NADH/$NAD^+$ ratio, comprising a polypeptide sensitive to environmental NADH/$NAD^+$ ratio, and a segment that exhibits the environmental NADH/$NAD^+$ ratio by change in its spectral characteristics. In a specific embodiment, the fluorescent sensor for NADH/$NAD^+$ ratio comprises SEQ ID NO: 148.

In another aspect, the invention provides a fusion protein comprising the fluorescent sensor of this invention. In one embodiment, the fusion protein comprises the fluorescent sensor of this invention and various specific signal for subcellular localization, wherein the signal allows localization of a target protein into a specified subcellular organelle.

In another aspect, the invention provides a nucleic acid sequence comprising the nucleotide sequence that encodes the fluorescent sensor or the fusion protein of the invention. In a specific embodiment, the invention provides a nucleic acid sequence comprising the nucleotide sequence encoding a fluorescent protein and a nucleotide sequence encoding a NADH sensitive protein.

In a preferred embodiment, the nucleotide sequence encoding the NADH sensitive protein is a nucleotide sequence encoding a polypeptide or its functional fragments or NADH binding domain having following characteristics:

(1) comprising a Rossman domain with NADH binding feature; and/or (2) derived from an NADH sensitive protein of transcription factor Rex family.

In another preferred embodiment, the nucleic acid sequence of the invention may comprise a coding sequence b for a Rossman domain having NADH binding feature and coding sequences a, a1 and/or a2 for fluorescent protein(s), in an arrangement of the following:

(1) b-a-b;

(2) b-a-b-b;

(3) a1-b-a2, wherein a1 and a2 can be the identical or not; a1 can be a coding sequence of a fluorescent protein from *Aequorea victoria* or a derivative thereof, a2 can be a coding sequence of another fluorescent protein from *Aequorea victoria* or a derivative thereof;

(4) a first portion of b-a-a second portion of b; wherein a is inserted in the flexible region of b such that b is segmented into the first portion of b and the second portion of b, while the first portion of b and the second portion of b constitute a complete b domain;

(5) a first portion of b-a-a second portion of b-b; wherein a is inserted in the flexible region of b such that b is divided into the first portion of b and the second portion of b, while the first portion of b and the second portion of b constitute a complete b domain.

In another preferred embodiment, the invention provides a nucleic acid sequence comprising nucleotide sequence SEQ ID NO: 9, 10, 11, 12, or 13. In a preferred embodiment, the invention provides a nucleic acid sequence comprising any homologous and non-homologous sequences having 99%, 95%, 90%, 80%, 70% or 50% identity with the nucleotide sequence SEQ ID NO: 9, 10, 11, 12 or 13 in at least 85 bases in length. In another preferred embodiment, the invention provides a nucleic acid sequence comprising nucleotide sequence that is substantially similar or identical to the nucleotide sequence of SEQ ID NO: 9, 10, 11, 12 or 13 in at least 85 bases; in a preferred embodiment, the invention provides a nucleic acid sequence comprising a variant or derivative of the nucleotide sequence of SEQ ID NO: 9, 10, 11, 12 or 13.

The present invention also relates to a complementary sequence and a variant of the aforementioned nucleic acid sequence, which may include a nucleic acid sequence or a complement of the sequences encoding fragments, analogues, derivatives, soluble fragments and variants of the fluorescent sensor or fusion protein of the invention.

In yet another aspect, the invention also provides an expression vector comprising the nucleic acid sequence of the invention operably linked to a expression control sequence. The expression control sequence can be an origin of replication, a promoter, an enhancer, an operon, a terminator, or a ribosome binding sites, etc.

In yet another aspect, the present invention also provides a host cell containing the expression vector of the invention.

In yet another aspect, the present invention also provides a method for preparing the fluorescent sensor or the fusion protein of this invention, comprising the following steps:

a. transferring the expression vector of the invention into a host cell, b. culturing the host cell under conditions suitable for the expression in the host cell, and c. separating the fluorescent sensor or fusion protein from host cells.

The invention also provides uses of the fluorescent sensor or the fusion protein of the invention in detecting NADH. In one embodiment, the invention provides uses of the fluorescent sensor or the fusion protein of the invention in detecting NADH in vitro or in vivo. In one embodiment, the invention provides uses of the fluorescent sensor or the fusion protein of the invention in detecting NADH at subcellular level. In one embodiment, the invention provides uses of the fluorescent sensor or the fusion protein in dectecting NADH in situ. In another embodiment, the invention provides uses of the fluorescent sensor or the fusion protein of the invention in drug screening, wherein the drugs may be used to adjust NADH level in a subject. In another embodiment, the invention provides uses of the fluorescent sensor or the fusion protein of the invention in diagnosis of diseases which are associated with the level of NADH.

The invention also provides a kit for NADH detection, which comprises the fluorescent sensor or the fusion protein of the invention. The detection can be conducted in vitro, in vivo, in situ, or at subcellular level. The invention also provides a kit for screening drug which can be used to adjust the NADH level in a subject, wherein the kit comprises an effective amount of fluorescent sensor or fusion protein of the invention. The invention also provides a kit for diagnosing diseases associated with the level of NADH, wherein the kit comprises an effective amount of the fusion protein of the invention. For said uses, one skilled in the art can readily determine the effective amount based on the activity of the fusion protein of the invention.

The protein and nucleic acid sequences of the invention are preferably provided in isolated form, and more preferably purified to homogeneity.

BRIEF DESCRIPTION OF THE FIGURES

The invention is further described with reference to the following figures and examples.

FIG. 7A shows changes of NADH in the cytoplasm of HEK293FT cells after the treatment of 3-NP and AOA.

FIG. 7B shows changes of NADH in the mitochondria of HEK293FT cells after the treatment of 3-NP and AOA.

FIG. 7C shows changes of NADH in the nucleus of HEK293FT cells after the treatment of 3-NP and AOA.

FIG. 7D shows changes of NADH in the membrane of HEK293FT cells after the treatment of 3-NP and AOA.

FIG. 7E shows changes of NADH in the Golgi of HEK293FT cells after the treatment of 3-NP and AOA.

FIG. 7F shows changes of NADH in the endoplasmic reticulum of HEK293FT cells after the treatment of 3-NP and AOA.

FIG. 7G shows changes of NADH in the peroxisomes of HEK293FT cells after the treatment of 3-NP and AOA.

FIG. 8-1A shows the real-time measurements of the NADH change within cells treated with exogenous NADH using a sensor for NADH/NAD$^+$ ratio over time.

FIG. 8-1B shows the real-time measurements of the NADH change within cells treated with exogenous NADH using a sensor for NADH/NAD$^+$ ratio compared to NADH concentration.

FIG. 8-1C shows the real-time measurements of the NADH change within cells treated with exogenous NADH using a sensor for NADH/NAD$^+$ ratio over time.

FIG. 8-1D shows the real-time measurements of the NADH change within cells treated with exogenous NADH using a sensor for NADH/NAD$^+$ ratio compared to NAD$^+$ concentration.

FIG. 8-1E shows the real-time measurements of the NADH change within cells treated with exogenous NADH using a sensor for NADH/NAD$^+$ ratio compared to NADPH concentration.

FIG. 8-2A shows the real-time measurements of the NADH change within cells treated with glucose using a sensor for NADH/NAD$^+$ ratio.

FIG. 8-2B shows the real-time measurements of the NADH change within cells treated with pyruvic acid using a sensor for NADH/NAD$^+$ ratio.

FIG. 8-2C shows the real-time measurements of the NADH change within cells treated with lactic acid using a sensor for NADH/NAD$^+$ ratio.

FIG. 8-2D shows the real-time measurements of the NADH change within cells treated with 25 mM of glucose using a sensor for NADH/NAD$^+$ ratio.

FIG. 8-3A shows the real-time measurements of the NADH level change within mitochondrias using a sensor for NADH/NAD$^+$ ratio.

FIG. 8-3B shows real-time measurements of the control protein cpYFP expressed in mitochondrias.

FIG. 8-3C shows the real-time measurements of the effect of other complex inhibitors on NADH level within mitochondrias using a sensor for NADH/NAD$^+$ ratio.

FIG. 9-1 shows the detection of cytosolic NAD$^+$ change using an NAD$^+$ sensor.

FIG. 9-2 shows the change of the response of NAD$^+$ sensor to NAD$^+$ in vitro.

FIG. 9-3 shows the response of NAD$^+$ sensor to pyridine nucleotide analogs under simulated physiological conditions in vitro.

FIG. 10-1 shows the characteristics of the sensor for NADH/NAD$^+$ ratio in response to the combination of NADH and NAD$^+$.

FIG. 10-2 shows the measurement results using the sensor for NADH/NAD$^+$ ratio at various NADH/NAD$^+$ ratios.

FIG. 10-3 shows the detection of the effect of pyridine nucleotide analogs to the sensor for NADH/NAD$^+$ ratio under simulative physiological conditions in vitro.

DESCRIPTION OF THE EMBODIMENTS

I. Definitions

Figure 1:
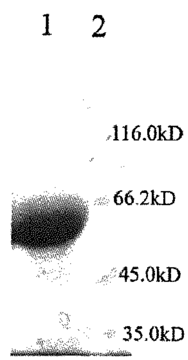
FIG. 1 shows SDS-PAGE characterizing F-rex1 separated and purified from *E. coli.*

When a numerical value or range is indicated, the term "about" used herein means the value or range is within 20%, 10% and 5% of the indicated value or range.

Terms such as "containing", "comprising" and its equivalents used herein shall be read as encompasses the meaning of "having" and "consisting of . . . ", for example, a composition "containing" X may consist exclusively of X or may include other substances, like X+Y.

In the invention, the term "YdiH protein" refers to protein YdiH (also known as Rex protein), which is a bacterial transcriptional inhibiting protein already known in the art. YdiH has a molecular weight of 23 kDa and regulates the fermentation and anaerobic respiration. It is a type of redox-sensitive regulatory protein which widely exists in Gram-positive bacteria, and is a typical NAD(H)-binding protein that containing Rossmann domain. The key Rossmann domain therein is a super secondary protein structure mainly presents in nucleotide binding proteins, a typical region active in binding cofactor NAD(H), and is represented by various cofactor NAD binding proteins. The structure is essentially comprised of 6 β-sheets linked through two pairs of α-helixes in the form of β-α-β-α-β. Since each Rossmann domain could bind one nucleotide molecule only, there are two Rossmann segments presented pairwise in dinucleotide-binding protein domains such as these for NAD. YdiH (Rex) protein can directly probe changes in cytoplasmic NADH/NAD$^+$ ratio, but under aerobic conditions, YdiH (Rex) protein can inhibit transcription of its target genes (cydABC, nuoA-D and rexhemACD) when intracellular NADH/NAD$^+$ ratio is at low level, while dissociates from its operon region at elevated NADH/NAD$^+$ ratio, and the steric configuration of YdiH (Rex) protein transforms upon the environment changes during this dynamic process. The "YdiH protein" involved in the invention may contain amino acid sequence encoded by nucleotide sequence of SEQ ID NO: 1 or SEQ ID NO: 2 or SEQ ID NO: 3. The "flexible region" referred to in the invention means specific structure, such as Loop configuration, presents in advanced protein structure. These structures exhibit better mobility and flexibility than other advanced structures of proteins, and are capable of causing dynamic change of domains, while proteins also exhibit significant tendency of undergo spatial conformational change in such regions. The flexible region referred to in the invention mainly means the V113-G119 region and D188-G192 region of T-rex (the Rex protein from *Thermus aquaticus*).

The term "fluorescent sensor" used herein refers to a polypeptide sensitive to environmental NADH and fused with a fluorescent protein, specifically, the polypeptide sensitive to environmental NADH can be a YdiH protein. The sensor utilizes the conformational changes of the fluorescent protein caused by binding of the NADH-specific binding structure Rossman domain in YdiH with NADH, and thus lead to the generation or reduction of fluorescence, or changes in the generated fluorescence; plotting standard curve based on the fluorescence of fluorescent protein measured under different NADH concentrations would, in turn, allow the detection and analy the presence and/or level of NADH.

The term "fusion protein" is synonymous with the terms "fluorescent fusion protein" and "recombinant fluorescent fusion protein", refers a polypeptide or protein comprising an amino acid sequence of a first polypeptide or protein, or fragment, analog or derivative thereof, and an amino acid sequence of a heterologous polypeptide or protein (that is, a second polypeptide or protein, or fragment, analog or derivative thereof, which differs from the first polypeptide or protein, or fragment, analog or derivative thereof). In one embodiment, the fusion protein comprises a fluorescent protein fused with the heterologous protein, polypeptide or peptide. According to this embodiment, the heterologous protein, polypeptide or peptide may or may not be a fluorescent protein of different type. In one embodiment, the fusion protein maintains or enhances its activity relative to the activity of the original polypeptide or protein prior to the fusion with heterologous protein, polypeptide or peptide. In a specific embodiment, the fusion protein comprises a fluorescent sensor fused with a heterologous protein, polypeptide or peptide, wherein the heterologous protein, polypeptide or peptide can be a specific subcellular localization signal.

The term "fluorophore" used here is synonymous with "fluorescent protein", representing a protein exhibits autofluorescence or emits fluorescence under illumination. Fluorescent proteins are often used as detection means, for instance, green fluorescent protein GFP and BFP, CFP, YFP, etc, derived therefrom GFP are routinely used in the biotechnology arts.

The term "GFP" used herein refers to green fluorescent protein, which is originally isolated from *Aequorea victoria*. The wild type AvGFP is consisted of 238 amino acids and has a molecular weight of about 26 kD, and amino acid sequence SEQ ID No: 20. Recent study confirms that Ser-Tyr-Gly, the three amino acids 65-67 in native GFP protein, are able to spontaneously form a fluorescent chromophore: p-hydroxybenzylideneimidazolinone, which is the primary emitting site. The wild-type AvGFP exhibits very complex spectral characteristics with its main fluorescence excitation peak at 395 nm and a secondary peak at 475 nm, whose amplitude intensity is about ⅓ of the main peak. Under standard solution condition, 395 nm excitation can produce 508 nm emission, and 475 nm excitation produces maximum emission at 503 nm wavelength.

The term "YFP" used herein refers to yellow fluorescent protein, which is derived from green fluorescent protein GFP, the amino acid sequence of which is up to 90% or more homologous to GFP, and the key change of YFP from GFP is that the substitution of amino acid 203 from threonine to tyrosine (T203Y). Compared to original AvGFP, the main excitation peak of YFP is red-shifted to 514 nm wavelength and emission wavelength shifted to 527 nm. Site-directed mutation of amino acid no. 65 of the YFP (S65T) thereupon will obtain the fluorescence enhanced yellow fluorescent protein EYFP, and typical EYFP amino acid sequence is SEQ ID NO: 21. And sequence rearrangement of the EYFP protein by having the original amino acids 145-238 as the N terminus, and the original amino acid 1-144 as the C terminus of the new protein, with the two fragments linked through a short flexible peptide chain VDGGSGGTG forms cpYFP (circular permutation yellow fluorescent protein) that is sensitive to spacial changes, and typical cpYFP amino acid sequence is SEQ ID NO: 22.

In this invention, the YdiH protein that fused with fluorophore can be a full length native YdiH protein, or a fragment thereof, isolated from *Bacillus subtilis* or *Thermus aquaticus* or *Streptomyces coelicolor*; amino acids 1-215 of native YdiH protein from *Bacillus subtilis* or amino acids 1-211 of YdiH protein from *Thermus aquaticus*, or amino acids 1-259 of YdiH protein from *Streptomyces coelicolor* are preferable; while amino acids 1-215 of YdiH protein from *Bacillus subtilis* or amino acids 1-211 of YdiH protein from *Thermus aquaticus* are more preferable.

"Linker" means an amino acid or nucleic acid sequence linking the two segments within a polypeptide, protein or nucleic acid in the invention. When linking for a polypeptide or protein of the invention, the length of the linker is no longer than 6 amino acids, preferably, no longer than four amino acids, more preferably, 3 amino acids. When linking for a nucleic acids of the invention, the length of the linker is no longer than 18 nucleotides, preferably no longer than 12 nucleotides, more preferably 9 nucleotides.

When referring to a polypeptide or protein, the term "variant" used herein includes variants of the polypeptide or protein with the same function but differ in sequence. These variants include, but not limited to, sequences obtained by deleting, inserting and/or substituting one or more (typically 1-30, preferably 1-20, more preferably 1-10, and most preferably 1-5) amino acid(s) in the sequence of the polypeptide or protein, and by adding one or more (usually less than 20, preferably less than 10, and more preferably within 5) amino acid(s) to its C-terminus and/or N-terminus. For example, in the art, substitution with amino acids of comparable or similar properties usually does not change the function of the polypeptide or protein. Amino acids with similar properties usually refer to a family of amino acids having similar side chains and have been clearly defined in the art. These families include amino acids with basic side chains (e.g., lysine, arginine, histidine), amino acids with acidic side chains (e.g., aspartate, glutamate), amino acids with uncharged polar side chain (e.g., glycine, asparagine, glutamine, serine, threonine, tyrosine, cysteine), amino acids with non-polar side chains (e.g., alanine, valine, leucine, isoleucine, proline, phenylalanine, methionine, tryptophan), amino acids with β-branched side chains (e.g., threonine, valine, isoleucine), and amino acids with aromatic side chains (e.g., tyrosine, phenylalanine, tryptophan, histidine). As another example, adding one or more amino acids to the C-terminus and/or N-terminus usually does not change the function of the polypeptide or protein either. As known to a person skilled in the art, genetic cloning process often requires design of suitable endonuclease sites, which will eventually introduce one or more irrelevant residues to the terminus of the polypeptide or protein to be expressed, but this does not affect the activity of the target polypeptide or protein. For another example, in order to construct a fusion protein, to promote the expression of a recombinant protein, to obtain a recombinant protein that can secrete itself into the extracellular environment of the host cells, or to facilitate the purification of a recombinant protein, it is often desirable to have the N-terminus, C-terminus, or other suitable regions of the protein added with some amino acids, for example, including, but not limited to, suitable connecting peptides, signal peptides, leader peptides, the terminal extensions, the glutathione S-transferase (GST), maltose E binding protein, Protein A, tags such as 6His or Flag, or factor Xa or thrombin or enterokinase protease cleavage sites. Variants of the polypeptide or protein may include: homologous sequences, conservative variants, allelic variants, natural mutants, induced mutants, polypeptide or protein encoded by a DNA which could hybridize with the DNA for said polypeptide or protein under high or low stringent conditions, as well as the polypeptide or protein derived from antiserum against said polypeptide or protein. These variants may also comprise polypeptide or protein whose sequence is at least about 70%, at least about 75%, at least about 80%, at least about 85%, at least about 90%, at least about 95%, at least about 98%, at least about 99%, or 100% sequence identity with said polypeptide or protein.

In the context of two or more polypeptides or nucleic acid sequences, the term "identical" or "percent identity" means, when compared and aligned for maximum correspondence over a comparing window or designated region using available methods such as comparing algorithms known in the art or by manual alignment and visual inspection, two or more sequences or sub-sequences are the same or have a specified percentage of amino acid residues or nucleotides that are the same (e.g., 60%, 65%, 70%, 75%, 80%, 85%, 90%, 91%, 92%, 93%, 94%, 95%, 96%, 97%, 98%, 99% or 100% are the same). For example, preferred algorithms that are suitable for determining the percent sequence identity or similarity are the BLAST and BLAST 2.0 algorithms, which can be found in Altschul (1977) Nucleic Acids Res. 25:3389 and Altschul (1990) J. Mol Biol. 215:403, respectively.

The term "soluble fragment" used herein generally refers to fragments having at least about 10 consecutive amino acids of the full-length protein sequence, usually at least about 30 consecutive amino acids, preferably at least about 50 consecutive amino acids, more preferably at least about 80 consecutive amino acids, and optimally at least about 100 consecutive amino acids.

The terms "functional fragment", "derivative" and "analog" mean proteins retain substantially the same biological function or activity of the native YdiH protein in the invention. Functional fragments, derivatives or analogs of YdiH in the invention may be (i) proteins with one or more conservative or non-conservative amino acid substitution (preferably conservative), where the substituted amino acid residues may or may not be one encoded by the genetic code, or (ii) proteins containing substitutions of one or more amino acid residues having a substituent group, or (iii) proteins formed having the mature protein fused with another compound (such as compounds that extend half-life of the protein, for example, polyethylene glycol), or (iv) proteins formed by having said protein fused with additional amino acid sequence (such as leader sequence or secretory sequence, or sequence used for purification of the protein or proprotein sequence, or fusion protein formed with fragment of antigen IgG). In accordance with the teachings provided herein, these functional fragments, derivatives and analogs are well known to a person skilled in the art.

The differences between analogs and the native YdiH protein may be the difference in amino acid sequences, and may also be the difference in the forms of modifications that will not affect the sequence, or both. These proteins include natural or induced genetic variants. Induced variants can be obtained by a variety of techniques, such as generating random mutagenesis by irradiation or exposure to mutagens, and can also be obtained by directed mutagenesis or other known molecular biology techniques.

Analogs mentioned herein also include analogs with residue(s) different from natural L-amino acid (e.g., D-amino acids), as well as analogs with a non-naturally occurred or synthetic amino acid (such as β, γ-amino acids). It should be understood that the YdiH protein of the invention is not limited to the representative proteins, fragments, derivatives and analogs exemplified above. Forms of modification (usually without change of the primary structure): chemical derivatization of the protein in vivo or in vitro, such as acetylation or carboxylation. The modifications also include glycosylation, such as proteins generated by conducting glycosylation during protein synthesis and processing or further processing steps. This modification can be achieved by exposure of the protein to an enzyme that glycosylates (such as mammalian glycosylase or deglycosylase). The modifications also include sequences with phosphorylated amino acid residues (e.g. phosphotyrosine, phosphoserine, phosphothreonine), and further include protein modified to improve its anti-proteolytic properties, or to optimize the solubility.

The term "nucleic acid" used herein be in the form of DNA or RNA. Forms of DNA includes cDNA, genomic DNA or artificially synthesized DNA. The DNA may be single-stranded or double-stranded. The DNA may be coding strand or non-coding strand. The coding sequence that encodes the mature protein can be identical with the sequence shown in the coding region of SEQ ID NO: 9, 10, 11, 12 or 13, or its degenerate variants. "Degenerate variant" used in the invention refers to a nucleic acid sequence that encodes the fluorescent fusion protein of the invention, but is different from the coding region sequence shown in SEQ ID NO: 9, 10, 11, 12 or 13.

In the context of nucleic acid, the term "variants" used herein may be naturally occurring allelic variants or non-naturally occurring variants. These nucleotide variants include degenerate variants, substituted variants, deletion variants, and insertion variants. As known in the art, allelic variant is an alternate form of a nucleic acid, it may be caused by one or more nucleotide substitution, deletion or insertion, but does not substantially alter the function of the encoded protein. The nucleic acid of the invention may include nucleotide sequences with at least about 70%, at least about 75%, at least about 80%, at least about 85%, at least about 90%, at least about 95%, at least about 98%, at least about 99%, or 100% identity with said nucleic acid sequence.

As used herein, the term "hybridizing under stringent conditions" is used to describe conditions for hybridization and washing under which nucleotide sequences at least 60% homologous to each other typically remain hybridized to each other. Preferrably, stringent conditions are the conditions that under which sequences at least 65%, more preferably at least 70%, and even more preferably at least 80% or higher homologous to each other typically remain hybridized to each other. The stringent condition is known to a person of ordinary skills in the art. In one preferred, non-limiting example, the stringent conditions are: (1) hybridization and elution under relatively low ionic strength and relatively high temperature, such as 0.2×SSC, 1% SDS, 0° C.; or (2) hybridization at the addition of denaturing agent, 50% (v/v) methyl amide, 0.1% fetal calf serum/0.1% Ficoll, 42° C., etc; or (3) hybridization occurred only between two sequences at least 90%, more preferably no less than 95% homologous to each other. Furthermore, the protein encoded by the nucleic acid sequences capable of hybridization has the same biological function and activity as the mature protein shown in SEQ ID NO: 4, 5, 6, 7 or 8.

The present invention also relates to a nucleic acid fragment hybridizes with the sequence described above. As used here, the length of "nucleic acid fragment" contains at least 15 nucleotides, preferably at least 30 nucleotides, more preferably at least 50 nucleotides, and most preferably at least 100 or more nucleotides. The nucleic acid fragment can be used for nucleic acid amplification techniques (e.g. PCR).

Generally, the full-length sequences or the fragments of the fluorescent sensor or fusion protein in the invention can be obtained by PCR amplification method, recombination method or artificially synthetic method. For PCR amplification, primers can be designed according to the relevant nucleotide sequence disclosed by the invention, and in particular, the sequence of the open reading frame, and commercially available cDNA library, or cDNA library prepared by person skilled in the art using routine methods could be used as template, thereby, obtaining the corresponding sequences by amplification. For longer sequences, two or more individual PCR amplifications are typically desired, which are followed by ligating the separately amplified fragment together in a proper order.

Once the corresponding sequence is obtained, a large quantities of the sequences can be achieved by recombination. Typically, the sequences is cloned into a vector, which is subsequently transferred into cell, and then the corresponding polypeptide or protein can be obtained from the proliferated host cells by routine isolation and purification methods.

Furthermore, artificial synthesis can also be used to synthesize the corresponding sequence, especially when the fragment is short. Typically, multiple smaller fragments are synthesized first, and later linked together to produce a fragment with much longer sequence.

So far, the DNA sequence that encoding the protein herein (or its fragment, derivative, analog or variant) can be obtained solely by chemical synthesis. Said DNA sequence can be introduced subsequently into various available DNA molecules (e.g. vectors) and cells that are already known in the art. Through mutant PCR or chemical synthesis methods, a mutation can be introduced into the sequence of the protein of the invention.

As used herein, the terms "expression vector" and "recombinant vector" may be used interchangeably, and refer to a prokaryotic or eukaryotic expression vector known in the art, such as a bacterial plasmid, bacteriophage, yeast plasmid, plant cell virus, mammalian cell virus such as adenovirus, retroviral or other vectors, which can replicate and stabilize in the host organism. One important feature of these recombinant vectors is that they typically comprise expression control sequences. As used herein, the term "expression control sequence" refers to an element that regulates transcription, translation and expression of a target gene, and may be operably linked with the target gene, said element may be an origin of replication, a promoter, a marker gene or translation control elements, including enhancers, operons, terminators, ribosome binding sites, etc., and the selection of expression control sequence depends on the host cell used. In present invention, suitable recombinant vector includes, but not limited to, bacterial plasmid. In the context of recombinant expression vector, "operably linked" means the target nucleotide sequence and the regulatory sequence are linked in a way that allows expression of the nucleotide sequence. Suitable methods for constructing expression vector which comprises the coding sequence of the fusion protein and appropriate transcriptional/translational control signals are well known to the person skilled in the art. These methods include in vitro recombinant DNA techniques, DNA synthesis techniques, in vivo recombination techniques, etc. Said DNA sequence may be effectively linked to a proper promoter in the expression vector to direct mRNA synthesis. Representative examples of promoters include *E. coli* lac or trp promoter; λ phage PL promoter; eukaryotic promoters include CMV immediate early promoter, HSV thymidine kinase promoter, early and late SV40 promoter, retrovirus LTR, and some other promoters known to control expression of genes in prokaryotic or eukaryotic cells or their viruses. Expression vector further comprises a ribosome binding site for the initiation of translation, and a transcription terminator.

A person of ordinary skills in the art will understand that design of the recombinant expression vector can vary depending on the host cell to be transformed, desired expression level of the protein and other factors. In addition, the recombinant expression vector preferably contains one or more selective marker genes to provide phenotypic traits, such as dihydrofolate reductase, neomycin resistance in eukaryotic cells, or tetracycline or ampicillin resistance in *E. coli*, for the selection of transformed host cells.

In one embodiment, the coding sequence of the fluorescent sensor or fusion protein in present invention is double digested with BamHI and HindIII and ligated into the $pRSET_b$ vector digested with BamHI and HindIII to obtain an *E. coli* recombinant expression vector. The expression vector of the present invention can be transferred into a host cell to produce a protein or peptide comprising the fusion protein. This transfer process may be carried out using routine transformation or transfection techniques well known to a person skilled in the art.

As used herein, the term "host cell", also known as recipient cells, refers to cells capable of receiving and accommodating recombinant DNA molecule(s), which is the place for recombinant gene amplification. An ideal recipient cell should satisfy two criteria: easily available and proliferating. The "host cell" in present invention may include prokaryotic cells and eukaryotic cells, specifically, include bacterial cells, yeast cells, insect cells and mammalian cells.

The expression vector in present invention can be used to express the fluorescent sensor or fusion proteins in prokaryotic or eukaryotic cells. Accordingly, the present invention relates to a host cell, preferably *E. coli*, having the expression vector of the invention incorporated therein. The host cell can be any prokaryotic or eukaryotic cell, representative examples include: bacterial cells including *E. coli, Streptomyces, Salmonella typhimurium*, fungal cells such as yeast, plant cells, insect cells as *Drosophila* S2 or Sf9, animal cells as CHO, COS, 293 cells or Bowes melanoma cells, etc., host cells described above are inclusive but not limiting. Said host cells are preferably those advantageous for expression of the gene product or the fermentative production, such cells are well known and routinely used in the art, for example, various *E. coli* cells and yeast cells. In one embodiment of the present invention, *E. coli BL*21 is selected to construct a host cell that expresses the fusion protein of present invention. The choice of appropriate carrier, promoter, enhancer and host cells is evident to a person of ordinary skills in the art.

As used herein, the term "transformation" and "transfection", "incorporating" and "transduction" refer to various techniques, already known in the art, to introduce exogenous nucleic acid (e.g., linear DNA or RNA (e.g., linearized vector or individual gene construct without vector)) or nucleic acid in the form of carrier (e.g., plasmids, cosmids, phage, phagemid, phasmid, transposon or other DNA) into a host cell, including calcium phosphate or calcium chloride coprecipitation, DEAE-mannan-mediated transfection, lipid transfection, natural competent cells, chemical-mediated transfer, or electroporation. When the host is a prokaryote such as *E. coli*, competent cells capable of absorbing DNA can be harvested after exponential growth phase, and treated with $CaCl_2$ method, the steps used therein are well known in the art. Another method uses $MgCl_2$. If necessary, the transformation can also be conducted by electroporation. When the host cell is a eukaryotic cell, DNA transfection methods can be used are as follows: calcium phosphate co-precipitation method, conventional mechanical methods such as microinjection, electroporation, liposome packaging, etc.

Transformed cell obtained thereby may be cultured using routine methods which are suitable for the expression in the host cells in order to express the fusion protein of the present invention. Depending on the host cells, the medium used for culture can be various conventional media. The culture is performed under conditions suitable for the growth of the host cells. When the host cells have grown to an appropriate cell density, the selected promoter is induced by an appropriate method (such as temperature shift or chemical induction), and the cells are further incubated for another period of time.

In the above method, the recombinant protein can be expressed within the cell, or on the cell membrane or secreted into extracellular environment. If desired, the recombinant protein can be isolated or purified using various separation methods based on its physical, chemical and other characteristics. These methods are well known to a person skilled in the art. Examples of such methods include, but not limited to: conventional refolding treatment, treatment with a protein precipitating agent (salting out), centrifugation, osmotic lysis of bacteria, ultra treatment, ultra centrifugation, molecular sieve chromatography (gel filtration), adsorption chromatography, ion exchange chromatography, high performance liquid chromatography (HPLC) and various other liquid chromatography techniques, and combinations thereof.

In one embodiment, the fluorescence sensor or a fusion protein of present invention is produced by fermentation of *E. coli* comprising the coding sequence of the fusion protein, followed by ammonium sulfate sedimentation, ion exchange chromatography, and purification using gel filtration chromatography to obtain the fluorescent sensor or a fusion protein of the invention in a pure form.

Uses of the fluorescent sensor or fusion protein of the present invention include, but not limited to, detection of NADH, detection of NADH in physiological state, detection of NADH in subcellular level, in situ detection of NADH, screening of drugs, diagnostics of diseases associated with NADH level.

Concentrations, contents, percentages, and other numerical values may be presented herein in a range format. It is to be understood that such range format is used merely for convenience and brevity, and it should be interpreted flexibly to include not only the numerical values explicitly recited as the upper and lower limits of the range, but also to include all the individual numerical values or sub-ranges encompassed within said range as if each numerical values or sub range is explicitly recited.

EXAMPLES

The invention is further illustrated by the specific examples described below. It should be understood that these examples are merely illustrative, and do not limit the scope of the present invention.

Unless otherwise indicated, experimental protocols in the following examples generally adopt customary conditions, such as those described in Sambrook et al., *Molecular Cloning: A Laboratory Guide*" (New York, USA: Cold Spring Harbor Laboratory Press, 1989); or the conditions according to the manufacturer's recommendations. Unless otherwise indicated herein, all percentages and parts are by weight.

I. Experimental Materials and Reagents

Reagents: Unless otherwise indicated, all reagents were purchased from Shanghai Sinopharm Chemical Reagent Co. Ltd. (Shanghai, China).

Tag enzymes, buffer, dNTP for PCR amplification; protease, buffer, T4 DNA ligase, T4 DNA ligase buffer, T4 polynucleotide kinase (PNK), T4 PNK buffer used in molecular biological experiments were all from Fermentas (Vilnius, Lithuania).

Example 1 Construction and Expression of pRSET$_b$-ydiH-YFP-ydiH (D2)

1. Amplification of Nucleic Acid Sequence of cpYFP

The coding sequence of yellow fluorescent protein (cpYFP) was amplified using pMD19-cpYFP (Nagai, T. et al., Proc Natl Acad Sci U.S.A. 2001, V.98(6), pp. 3197-3202) (obtained from Protein Chemistry Laboratory, East China University of Science and Technology (Shanghai, China)) as the template, and cpYFP F and cpYFP R as primers, where the primer sequences (primers were synthesized by Sangon Biotech (Shanghai) Co. Ltd., Shanghai, China) are as follows:

P1: SpeI
(SEQ ID NO: 23)
GAAATCGAA*ACTAGT*TACAACAGCCACAACGTCTATATC

P2: KpnI
(SEQ ID NO: 24)
CCAAGCTTCGG*GGTACC*GTTGTACTCCAGCTTGTG

PCR Reaction System

| PCR system | |
|---|---|
| Template | 1 μl |
| Forward primer | 0.5 μl |
| Reverse primer | 0.5 μl |
| 10× Taq buffer | 5 μl |
| Taq enzyme | 1 μl |
| dNTP (10 mM) | 1 μl |
| $ddH_2O$ | 41 μl |
| total | 50 μl |

PCR Reaction Conditions:

| | | |
|---|---|---|
| | 95° C | 5 min |
| 30 cycles | 95° C. | 40 s |
| 30 cycles | 55° C. | 40 s |
| | 72° C. | 1 min |
| | 72° C. | 10 min |

PCR amplification product was electrophoresed on a 1% agarose gel for 30 minutes to obtain cpYFP fragments of about 750 bp. cpYFP fragments were recovered and purified from the gel using Sangon DNA fragment recovery kit (Sangon Biotech (Shanghai) Co. Ltd., Shanghai, China) according to the manufacturer's instructions.

2. Extraction of Desired Gene Sequence from *Bacillus subtilis* 168 Cells a. Sample Processing (i) *Bacillus subtilis* 168 was obtained from China General Microbiological Culture Collection Center (Cat. No. 1.1656).

(ii) According to the conditions as described, 100 μl cultured *Bacillus subtilis* 168 was taken to measure the optical density of the broth at 600 nm, where $OD_{600}$=0.1 refers to a density of $1\times10^7$~$5\times10^7$ cells/ml, the actual number of cells was calculated thereby. Then 1 ml TRIzol reagent (Invitrogen, California, USA) would be added per $1\times10^7$ cells for processing.

(iii) A proper amount of broth was taken, centrifuged at 4° C., 5000 rpm for 10 minutes, and the supernatant was discarded.

(iv) Bacterial pellet was washed with 100 μl×TE buffer (10 mM Tris-HCl, 1 mM EDTA pH8.0, reagents were from Armco corporation (Amresco, Ohio, USA)), and centrifuged at 5000 rpm for 10 minutes, and the supernatant was discarded.

(v) The bacterial pellet was resuspend in 100 μl 1×TE buffer (comprising 2 mg/ml lysozyme (from Majorbio Biotech Co. Ltd., Shanghai, China)) and incubated at 37° C. for 30 minutes.

b. Phase Separation (i) One milliliter of TRIzol reagent (Invitrogen) was added thereto and mixed by pipetting, and the mixture was allowed to stand at room temperature for 5 minutes.

(ii) Two hundred microliter of chloroform was added thereto and vortexed for 15 seconds, and the mixture was allowed to stand at room temperature for 2 to 3 minutes prior to centrifugation at 4° C., 12,000 g for 15 minutes.

(iii) The solution was segmented into layers upon centrifugation, comprising about 40% of upper aqueous phase containing RNA, and about 60% of lower organic phase containing DNA and protein. The upper aqueous phase was carefully pipetted out and removed.

c. Removal of Impurities

Fifty microliter of 10% SDS and 250 μl saturated aqueous sodium chloride solution were added into the organic phase, and vortexed to homogenous prior to centrifugation at 4° C., 12,000 g for 5 minutes, and the upper aqueous phase was discarded.

d. Ethanol Precipitation of DNA

Seven hundred and fifty microliter of precooled 95% ethanol was added into the organic phase and inverted to mix, and stand at −80° C. for 15 minutes to allow the DNA to precipitate.

e. DNA Washing (i) The upper organic phase was carefully discarded.

(ii) The precipitate was washed several times with 1 ml of 0.1 M sodium citrate/10% ethanol solution, centrifugation at 4° C., 12,000 g for 5 minutes was conducted after each wash.

(iii) A final wash was conducted with 75% ethanol and followed by centrifugation at 4° C., 12 000 g for 5 minutes.

(iv) The ethanol was evaporated through air dry at room temperature.

f. Dissolving DNA

DNA pellet was dissolved into 50 μl of 8 mM NaOH solution, and stored at 4° C. or −20° C.

The gene for YdiH protein of *Bacillus subtilis* 168 (ydiH), in full length or fragment thereof (for amino acids 85-215), was amplified using genomic material extracted above as the template, and primers ydiH-1F and ydiH 1R, ydiH(D2) 2F and ydiH 2R, respectively, wherein amplification with ydiH-1F and ydiH 1R produced ydiH1, the full length YdiH protein gene (ydiH) having BaHI restriction site at 5' end and SpeI restriction site at 3' end; amplification with ydiH (D2) 2F and ydiH 2R produced ydiH(D2) 2, a fragment of YdiH Protein gene (ydiH) (for amino acids 85-215) having KpnI restriction site at 5' end and HindIII restriction site at 3' end. Sequences of the primers ydiH 1F, ydiH 1R, ydiH (D2) 2F and ydiH 2R are as follows:

```
ydiH 1F: BamHI
                                   (SEQ ID NO: 25)
CCGGATCCATGAATAAGGATCAATCAAAAATTC

ydiH 1R: SpeI
                                   (SEQ ID NO: 26)
GCTGTTGTAACTAGTTTCGATTTCCTCTAAAACT

ydiH(D2) 2F: KpnI
                                   (SEQ ID NO: 27)
CGGGGTACCATGACAGACGTCATCTTGATTGGTG

ydiH 2R: HindIII
                                   (SEQ ID NO: 28)
CCCAAGCTTCTATTCGATTTCCTCTAAAAC
```

PCR Reaction System:

| PCR system | |
|---|---|
| Template | 1 μl |
| Forward primer | 0.5 μl |
| Reverse primer | 0.5 μl |
| 10× Taq buffer | 5 μl |
| Taq enzyme | 1 μl |
| dNTP (10 mM) | 1 μl |
| $ddH_2O$ | 41 μl |
| total | 50 μl |

PCR Reaction Conditions:

| | | |
|---|---|---|
| | 95° C. | 5 min |
| 30 cycles | 95° C. | 40 s |
| | 55° C. | 40 s |
| | 72° C. | 1 min |
| | 72° C. | 10 min |

PCR amplification product was purified on 1% agarose gel by electrophoresis for 30 minutes to obtain the ydiH 1 of about 700 bp and ydiH (D2) 2 fragment of about 450 bp. The amplified ydiH 1 and ydiH (D2) 2 fragments were recovered and purified from the gel using Sangon DNA fragment recovery and purification kit (Sangon Biotech (Shanghai) Co. Ltd., Shanghai, China) according to the manufacturer's instructions.

3. Ligation of the Target Gene Fragment to the Vector

Overlap extension PCR was conducted using ydiH 1 and cpYFP as templates, and ydiH 1F and cpYFP 1R as primers with the following PCR system:

| PCR system | |
|---|---|
| Template 1(1) | 1 μl |
| Template 2(1) | 1 μl |
| Forward primer(2) | 0.5 μl |
| Reverse primer(2) | 0.5 μl |

-continued

| PCR system | |
|---|---|
| 10× pfu buffer | 5 μl |
| pfu enzyme | 1 μl |
| dNTP (10 mM) | 1 μl |
| $ddH_2O$ | 40 μl |
| total | 50 μl |

PCR Reaction Conditions:

| PCR reaction conditions | | |
|---|---|---|
| | 95° C. | 5 min |
| 10 cycles | 95° C. | 40 s |
| | 55° C. | 40 s |
| | 72° C. | 1 min 15 s |
| 20 cycles | 95° C. | 40 s |
| | 58° C. | 40 s |
| | 72° C. | 2 min 10 s |
| | 72° C. | 10 min |

(1) Template fragments need to be purified.

(2) The forward and reverse primers were initially absent in the reaction system but added after 10 cycles.

PCR amplification product was subjected to electrophoresis on 1% agarose gel for 40 minutes for the ydiH-cpYFP fragment of about 1400 bp. The recovered and purified PCR fragment ydiH-YFP and vector plasmid $pRSET_b$ were double digested separately with the following digestion systems:

| Double enzyme digestion system | |
|---|---|
| DNA fragment ydiH-YFP | 15 μl |
| BamHI | 1 μl |
| HindIII | 2 μl |
| 10× BamHI buffer | 5 μl |
| $ddH_2O$ | 27 μl |
| Total | 50 μl |

| Double enzyme digestion system | |
|---|---|
| Vector plasmid $pRSET_b$ | 10 μl |
| BamHI | 1 μl |
| HindIII | 2 μl |
| 10× BamHI buffer | 5 μl |
| $ddH_2O$ | 32 μl |
| total | 50 μl |

Reaction conditions: 37° C., 5 hours.

After the reaction was concluded, 10 μl of 6× loading buffer was added to the 50 μl reaction system to stop the reaction. Then target fragments were isolated by agarose gel electrophoresis, recovered and purified using Sangon DNA fragment recovery kit (Sangon Biotech (Shanghai) Co. Ltd., Shanghai, China) according to the manufacturer's instructions.

The double digested fragment of ydiH-cpYFP and the double digested fragment of vector plasmid $pRSET_b$ recovered above were ligated using the following systems:

| Ligation system | |
|---|---|
| DNA fragment ydiH-YFP | 4 |
| Fragment $pRSET_b$ vector | 1 |
| T4 DNA ligase | 0.5 |
| 10× T4 DNA ligase buffer | 1 |
| $ddH_2O$ | 3.5 |
| total | 10 |

Reaction conditions: 16° C., overnight. Ligated product $pRSET_b$-ydiH-YFP was formed thereby.

Finally, ydiH (D2) 2 described above and validated $pRSET_b$-ydiH-YFP were double digested as following:

| Double enzyme digestion system | |
|---|---|
| Vector plasmid $pRSET_b$-ydiH-YFP | 10 μl |
| KpnI | 1 μl |
| HindIII | 2 μl |
| 10× KpnI buffer | 5 μl |
| $ddH_2O$ | 32 μl |
| total | 50 μl |

| Double enzyme digestion system | |
|---|---|
| DNA fragment ydiH(D2) 2 | 15 μl |
| KpnI | 1 μl |
| HindIII | 3 μl |
| 10× KpnI buffer | 5 μl |
| $ddH_2O$ | 26 μl |
| Total | 50 μl |

Reaction conditions: 37° C. for 5 hours.

When the reaction was concluded, 10 μl of 6× loading buffer was added to the 50 μl reaction system to terminate the reaction. Target fragments were then isolated by agarose gel electrophoresis, recovered and purified using Sangon DNA fragment recovery kit (Sangon Biotech (Shanghai) Co. Ltd., Shanghai, China) according to the manufacturer's instructions.

As described above, the double digested product of ydiH (D2) 2 and $pRSET_b$-ydiH-YFP were recovered and ligated to form the final ligation product $pRSET_b$-ydiH-YFP-ydiH (D2).

Positive colonies identified by PCR identification were selected, and sequenced using universal primers at the Shanghai Branch of Beijing Liuhe BGI Technology Co., Ltd. The sequence data was analysed and compared using Vector NTI 8.0. The results showed that the plasmid was actually comprising inserted nucleotide sequence of ydiH-cpYFP-ydiH (D2) (sequence shown as SEQ ID NO: 9 in the sequence listing), which encodes the protein shown as SEQ ID NO: 4 in the sequence listing.

4. Transformation

The recombinant plasmid $pRSET_b$-ydiH-cpYFP-ydiH (D2) was transformed into competent *E. coli* BL21 (DE3) pLysS (purchased from Tiangen Biotech Co. Ltd., Beijing, China) to obtain recombinant *E. coli* BL-Frex, the detailed process is as follows:

(i) One microliter of plasmid or 10 μl of ligation product was added to 100 μl competent bacteria under sterile condition, then kept in ice bath for 45 minutes;

(ii) After ice bathing, the mixture was immediately heat shocked in a 42° C. water bath for 90 to 120 seconds;

(iii) Subjected to ice bath for another 5 minutes;

(iv) Recovered by adding 800 μl LB liquid medium and incubating at, 150 rpm on a shaker for 1 hour;

(v) Centrifuged at 4000 rpm for 5 minutes at room temperature, the supernatant was discarded;

(vi) The pellet was resuspended into a small amount of fresh LB, the entire suspension was then evenly spreaded on LB plates, which were inverted and incubated overnight at 37° C.

Positive colonies were selected using conventional Colony PCR, transferred to 5 ml LB liquid medium containing the appropriate selective pressure, and cultured overnight at 37° C., 220 rpm. The recombinant strain BL-Perex was cultured in LB medium at 37° C., and 0.1 mM IPTG was added when the OD for cell concentration reached 0.8. The expression was induced at 18° C. for 20 hours, and F-rex1 protein was isolated and purified from the bacterial lysate using $Ni^{2+}$ affinity chromatography column (General Electric Company, Uppsala, Sweden). The SDS-PAGE identified only one protein band at approximately 66.5 kD, which was the F-rex1 protein (FIG. 1). As shown in FIG. 1, band 1 is the F-rex protein purified by $Ni^{2+}$ affinity chromatography column, and band 2 is the marker.

Example 2 Construction and Expression of pRSET$_b$-ydiH(189)-YFP-ydiH(190)

1. Amplification the Nucleic Acid Sequence of cpYFP:

The coding sequence of yellow fluorescent protein (cpYFP) was amplified using pMD19-cpYFP as the template, and cpYFP F and cpYFP R as primers, where the primer sequences (primers were synthesized by Sangon Biotech (Shanghai) Co. Ltd., Shanghai, China) are as follows:

```
P1: PstI
                                        (SEQ ID NO: 29)
GAATCTGCAGGCTACAACAGCCACAACGTCTATATC

P2: KpnI
                                        (SEQ ID NO: 30)
CCAAGCTTCGGGGTACCGTTGTACTCCAGCTTGTG
```

PCR Reaction System

| PCR system | |
|---|---|
| Template | 1 μl |
| Forward primer | 0.5 μl |
| Reverse primer | 0.5 μl |
| 10× Pfu buffer | 5 μl |
| Pfu enzyme | 1 μl |
| dNTP (10 mM) | 1 μl |
| ddH$_2$O | 41 μl |
| total | 50 μl |

PCR Reaction Conditions:

| | | |
|---|---|---|
| | 95° C. | 5 min |
| 30 cycles | 95° C. | 30 s |
| | 55° C. | 30 s |
| | 72° C. | 1 min 15 s |
| | 72° C. | 10 min |

PCR amplification product was electrophoresed on 1% agarose gel for 20 minutes to obtain cpYFP fragment of approximately 750 bp. cpYFP fragments were recovered and purified from the gel using Sangon DNA fragment recovery kit (Sangon Biotech (Shanghai) Co., Ltd., Shanghai, China) according to the manufacturer's instructions.

2. Amplification of Target Gene Sequence for YdiH Protein of *Thermus aquaticus*

The gene T-ydiH for YdiH protein of *Thermus aquaticus* was synthesized by Shanghai Generay Biotech Co. Ltd. (Shanghai, China) (synthesized according to the full-length gene sequence deposited in NCBI GenBank, NCBI Genbank AF061257.1).

Then the full length T-ydiH sequence for YdiH protein of *Thermus aquaticus* was amplified using the gene described above as the template, and ydiH IF and ydiH 2R as primers. The amplification using primers ydiH IF and ydiH 2R produced YdiH in full length for T-YdiH protein and having BamHI digestion site at 5' end and HindIII digestion site at 3' end, wherein the sequences of primer ydiH F and ydiH of 2R are as follows:

```
P3: BamHI
                                        (SEQ ID NO: 31)
CCGGATCCGATGAATAAGGATCAATCAAAAATTC

P4: HindIII
                                        (SEQ ID NO: 32)
CCCAAGCTTCTATTCGATTTCCTCTAAAAC
```

PCR Reaction System

| PCR system | |
|---|---|
| Template | 1 μl |
| Forward Primer | 0.5 μl |
| Reverse Primer | 0.5 μl |
| 10× Pfu buffer | 5 μl |
| Pfu enzyme | 1 μl |
| dNTP (10 mM) | 1 μl |
| ddH$_2$O | 41 μl |
| total | 50 μl |

PCR Reaction Conditions:

| | | |
|---|---|---|
| | 95° C. | 5 min |
| 30 cycles | 95° C. | 40 s |
| | 55° C. | 40 s |
| | 72° C. | 1 min |
| | 72° C. | 10 min |

PCR amplification products was purified on 1% agarose gel by electrophoresis for 30 minutes to obtain the T-ydiH1 fragment of about 700 bp. The amplified T-ydiH fragment was recovered and purified using Sangon DNA fragment recovery purification kit (Sangon Biotech (Shanghai) Co. Ltd., Shanghai, China) according to the manufacturer's instructions.

3. Ligation of the Target Gene to the Vector

The recovered and purified PCR fragment T-ydiH and vector plasmid pRSET$_b$ were double digested separately with the following system:

| Double enzyme digestion system | |
|---|---|
| DNA fragment T-ydiH | 15 μl |
| BamHI | 1 μl |
| HindIII | 2 μl |
| 10× BamHI buffer | 5 μl |
| $ddH_2O$ | 27 μl |
| total | 50 μl |

| Double enzyme digestion system | |
|---|---|
| Vector plasmid $pRSET_b$ | 10 μl |
| BamHI | 1 μl |
| HindIII | 2 μl |
| 10× BamHI buffer | 5 μl |
| $ddH_2O$ | 32 μl |
| Total | 50 μl |

Reaction conditions: 37° C. for 5 hours.

After the reaction was concluded, 10 μl of 6× loading buffer was added to the 50 μl reaction system to stop the reaction. Then target fragments were isolated by agarose gel electrophoresis, recovered and purified using Sangon DNA fragment recovery kit (Sangon Biotech (Shanghai) Co. Ltd., Shanghai, China) according to the manufacturer's instructions.

The double digested fragment of T-ydiH and the double digested fragment of vector plasmid $pRSET_b$ as recovered above were ligated using the following system:

| Ligation system | |
|---|---|
| DNA fragment T-ydiH-YFP | 4 |
| Fragment $pRSET_b$ vector | 1 |
| T4 DNA ligase | 0.5 |
| 10× T4 DNA ligase buffer | 1 |
| $ddH_2O$ | 3.5 |
| total | 10 |

Reaction conditions: 16° C. overnight. Ligated product $pRSET_b$-ydiH was formed thereby.

The full length pRSETb-ydiH sequence was amplified using the validated PRSETb-ydiH as a template, T-ydiH (L190) F and T-ydiH (F189) R as primers. The amplification using primers T-ydiH(L190) F and T-ydiH (F189) R produced a full length fragment ydiH-pRSETb of the pRSETb-ydiH having PstI digestion site at 5' end and KpnI digestion site at 3' end, wherein the sequences of primers T-ydiH (L190) F and T-ydiH (F189) R are as follows:

```
P5: KpnI
                                        (SEQ ID NO: 33)
ATAGGTACCGGCCTGGCCGGCCTGACCCGGCTG

P6: PstI
                                        (SEQ ID NO: 34)
ATACTGCAGAGAAGTCCACGTTCTCCACGGCCACCTC
```

Finally, the yidH-$pRSET_b$ fragment produced thereby, and validated cpYFP fragment were double digested under following conditions:

| Double enzyme digestion system | |
|---|---|
| DNA fragment cpYFP | 15 μl |
| KpnI | 1.5 μl |
| PstI | 1.5 μl |
| 10× BamHI buffer | 5 μl |
| $ddH_2O$ | 27 μl |
| total | 50 μl |

| Double enzyme digestion system | |
|---|---|
| DNA fragment yidH-$pRSET_b$ | 10 μl |
| KpnI | 1.5 μl |
| PstI | 1.5 μl |
| 10×BamHI buffer | 5 μl |
| $ddH_2O$ | 32 μl |
| total | 50 μl |

Reaction conditions: 37° C., 5 hours.

After the reaction was concluded, 10 μl of 6× loading buffer was added to the 50 μl reaction system to terminate the reaction. Then target fragments were isolated by agarose gel electrophoresis, recovered and purified using Sangon DNA fragment recovery kits (Sangon Biotech (Shanghai) Co. Ltd., Shanghai, China) according to the manufacturer's instructions.

The double digested fragments of yidH-$pRSET_b$ and cpYFP as recovered above were ligated to form the final product $pRSET_b$-ydiH (189)-YFP-ydiH (190).

Positive colonies identified by Colony PCR were selected, sequenced using universal primers at the Shanghai Brance of Beijing Liuhe BGI Technology Co. Ltd. The determined sequence was compared and analysed using Vector NTI 8.0. The result showed that this plasmid was actually comprising inserted nucleotide sequence of ydiH (189)-YFP-ydiH (190) (sequence shown as SEQ ID NO: 13), and which encodes the protein shown as SEQ ID NO: 8 in the sequence listing.

4. Transformation

Recombinant plasmid $pRSET_b$-ydiH(189)-YFP-ydiH (190) was transformed into competent *E. coli* BL21 (DE3) pLysS (purchased from TIANGEN Biotech Co. Ltd., Beijing, China) to obtain the recombinant strain BL-Frex, the detailed process is as follows:

(i) One microliter of plasmid or 10 μl of ligation product was added to 100 μl of competent bacteria under sterile condition, then kept in ice bath for 45 minutes;

(ii) After ice bathing, the mixture was immediately heat shocked in a 42° C. water bath for 90 to 120 seconds;

(iii) Subjected to ice bath for another 5 minutes;

(iv) Recovered by adding 800 μl LB liquid medium, and incubating at 37° C., 220 rpm on a shaker for 1 hour;

(v) Centrifuged at 4000 rpm for 5 minutes at room temperature, and the supernatant was discarded;

(vi) The pellet was resuspended into a small amount of fresh LB, and the entire suspension was then evenly spreaded on LB plates, which were inverted and incubated overnight at 37° C.

Figure 2:
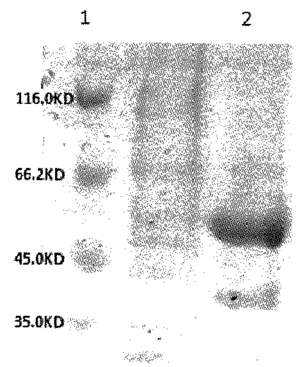
FIG. 2 shows SDS-PAGE characterizing F-rex2 separated and purified from *E. coli.*
Figures 12A, 12B, 12C:
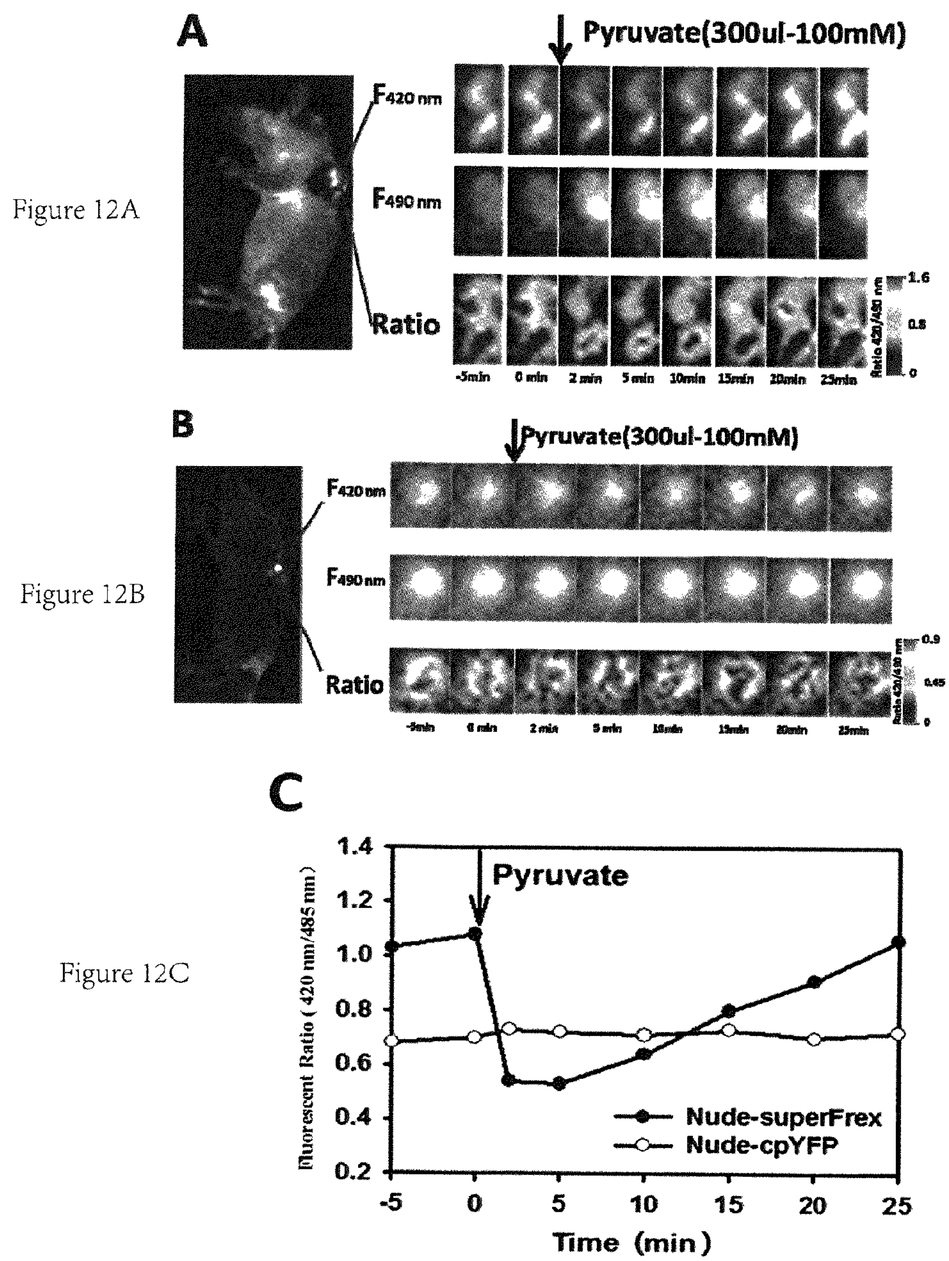
FIG. 12A shows a real-time detection of the metabolite levels of NADH/NAD$^+$ ratio in tumors by sensor for NADH/NAD$^+$ ratio fluorescence.
FIG. 12B shows a second real-time detection of the metabolite levels of NADH/NAD$^+$ ratio in tumors by sensor for NADH/NAD$^+$ ratio fluorescence.
FIG. 12C is a graph of real-time detection of the metabolite levels of NADH/NAD$^+$ ratio in tumors by sensor for NADH/NAD$^+$ ratio fluorescence as compared to control protein cyYFP.

Positive colonies were selected using conventional Colony PCR, transferred to 5 ml LB liquid medium containing the appropriate selective pressure, and cultured overnight at 37° C., 220 rpm. The recombinant strain BL-Perex was cultured at 37° C., and 0.1 mM IPTG was added when the OD of cell concentration reached 0.8. The expression was induced at 18° C. for 20 hours, and F-rex2 protein was isolated and purified from the bacterial lysate using $Ni^{2+}$ affinity chromatography column (General Electric Company, Uppsala, Sweden). The SDS-PAGE identified only one protein band at approximately 50 kD, which was the F-rex2 protein (FIG. 2). As shown in FIG. 12, band 1 is the F-rex2 protein purified by $Ni^{2+}$ affinity chromatography column, while band 2 is the marker.

Example 3. Derivatives of YdiH-YFP-ydiH (D2) Sensors

Principle for Sensor Construction

Derivative sensors were engineered using intermediate plasmids for the construction of $pRSET_b$-ydiH-YFP-ydiH and other sensors as templates, and following the principle of site-directed mutagenesis.

Truncated mutant sequences are shown below:

| Original sequence | 206 KHYSVLEEIE 215-TS-YFP-GT-ydiH | SEQ ID NO |
|---|---|---|
| Del T(2) | 206 KHYSVLEEIE 215-TS-YFP-G-ydiH | 104 |
| Del G | 206 KHYSVLEEIE 215-TS-YFP-T-ydiH | 103 |
| Del GT | 206 KHYSVLEEIE 215-TS-YFP-ydiH | 102 |
| Del S | 206 KHYSVLEEIE 215-T-YFP-GT-ydiH | 126 |
| Del T(1) | 206 KHYSVLEEIE 215-S-YFP-GT-ydiH | 101 |
| Del TS | 206 KHYSVLEEIE 215-YFP-GT-ydiH | 159 |
| C9 | 206 KHYSVLEEI 214-YFP-GT-ydiH | 100 |
| C8 | 206 KHYSVLEE 213-YFP-GT-ydiH | 99 |
| C2 | 206 KH 207-YFP-GT-ydiH | 93 |
| C1 | 206 K-YFP-GT-ydiH | 92 |

Establishment of the Mutant Library

1. Primer Design (Shanghai Sangon)

| SEQ ID No | Remark | Sequence (5'-3') |
|---|---|---|
| 35 | C9 Reverse | GATTTCCTCTAAAACTGAATAATGCTTC |
| 36 | C8 Reverse | TTCCTCTAAAACTGAATAATGCTTC |
| 37 | C6 Reverse | TAAAACTGAATAATGCTTCAAAAAATAA ACCAG |
| 38 | C5 Reverse | AACTGAATAATGCTTCAAAAAATAAACCAG |
| 39 | C4 Reverse | TGAATAATGCTTCAAAAAATAAACCAG |
| 40 | C3 Reverse | ATAATGCTTCAAAAAATAAACCAGTG |
| 41 | C2 Reverse | ATGCTTCAAAAAATAAACCAGTGACTG |
| 42 | C1 Reverse | CTTCAAAAAATAAACCAGTGACTGAAGC |
| 43 | C9 Forward (general forward primer for C series) | TACAACAGCGACAACGTC |
| 44 | C7 Reverse | CTCTAAAACTGAATAATGCTTC |
| 45 | Del GT Forward | ATGACAGACGTCATCTTGATTG |
| 46 | Del GT Reverse | GTTGTACTCCAGCTTGTGCC |
| 47 | Del TS Forward | TACAACAGCGACAACGTCTATATCATG |
| 48 | Del TS Reverse | TTCGATTTCCTCTAAAACTGAATAATGC |
| 49 | Del T(1) Forward | AGTTACAACAGCGACAACGTCTATATCATG |
| 50 | Del S-deletion Reverse | AGTTTCGATTTCCTCTAAAACTGAATAATGC |
| 51 | Del G-deletion Forward | ACCATGACAGACGTCATCTTGATTG |
| 52 | Del T(2)-deletion Reverse | ACCGTTGTACTCCAGCTTGTGCC |
| 53 | D118K Forward | TTTTAAGATAAATGAGAGTAAAATAGG |
| 54 | 118/120 mutation Reverse | GCCATAGAAATTTTTGTGTTATTG |
| 55 | D118R Forward | TTTTCGGATAAATGAGAGTAAAATAGG |
| 56 | N120K Forward | TTTTGATATAAAGGAGAGTAAAATAGG |
| 57 | N120R Forward | TTTTGATATACGGGAGAGTAAAATAGG |
| 58 | N120E Forward | TTTTGATATAGAAGAGAGTAAAATAGG |
| 59 | N120D Forward | TTTTGATATAGATGAGAGTAAAATAGG |
| 60 | D193N Forward | TAAATTTAGCAGTTGAGCTTCAG |
| 61 | 193/194 mutation Reverse | TATGATGAATTCGAATGTGTTC |
| 62 | D193K Forward | TAAAGTTAGCAGTTGAGCTTCAG |
| 63 | D193R Forward | TACGGTTAGCAGTTGAGCTTCAG |
| 64 | L194E Forward | TAGATGAAGCAGTTGAGCTTCAG |
| 65 | L194D Forward | TAGATGATGCAGTTGAGCTTCAG |
| 66 | L194K Forward | TAGATAAGGCAGTTGAGCTTCAG |
| 67 | L194R Forward | TAGATCGGGCAGTTGAGCTTCAG |

2. PCR Amplification

Truncated mutation and site-directed mutation were conducted using site-directed mutagenesis PCR.

Amplification system for PCR mutation (primer, enzyme, dNTP and others purchased from Fermentas):

| PCR sampling system | |
|---|---|
| Template | 0.1 μl |
| Forward Primer | 0.5 μl |
| Reverse Primer | 0.5 μl |
| 5× PrimeStar Buffer | 10 μl |
| PrimeStar polymerase | 0.5 μl |
| dNTP mix (10 mM) | 4 μl |
| $ddH_2O$ | 33.5 μl |
| Total | 50 μl |

| PCR reaction conditions | | |
|---|---|---|
| | 98° C. | 5 min |
| 30 cycles | 98° C. | 10 sec |
| 30 cycles | 55° C. | 5 sec |
| 30 cycles | 72° C. | 4.5 min |
| | 72° C. | 10 min |

3. Separation, Purification of DNA Fragments

DpnI digestion

The PCR amplified fragment was first treated with DpnI enzyme (from Fermentas) for 3 hours at 37° C. to remove the potential template plasmid contamination. The reaction system was then denatured and deactivated at 80° C. for 20 minutes. The deactivated mixture could be directly used for subsequent molecular biological experiments.

Phosphorylation of DNA Fragment

At the presence of ATP, the DNA fragment was treated with T4 polynucleotide kinase (T4 PNK) (from Fermentas) at 37° C. for 1 h to phosporylate the 5'-OH of DNA ribose ring, in order to allow the fragments to cyclize by self-ligation. Then the reaction system was denatured and deactivated at 75° C. for 10 minutes. The deactivated mixture could be directly used for subsequent molecular biological experiments.

Ligation

The phosphorylated DNA fragments (mutated DNA fragments: $pRSET_b$-ydiH-YFP or $pRSET_b$-YFP-ydiH) were cyclized by self ligation overnight at 16° C. with T4 DNA ligase enzyme (from Fermentas).

Double-Digestion of Mutant Plasmids

The extracted mutant plasmids $pRSET_b$-ydiH-YFP series and $pRSET_b$-YFP-ydiH series were double digested, respectively. The digestion systems are as follows:

| Double-digest system | |
|---|---|
| Mutant plasmid $pRSET_b$-ydiH-YFP series | 10 μl |
| BsrGI | 1 μl |
| HindIII | 2 μl |
| 10× Tango buffer | 5 μl |
| $ddH_2O$ | 32 μl |
| Total | 50 μl |

| Double-digest system | |
|---|---|
| Mutant plasmid $pRSET_b$-YFP-ydiH series | 10 μl |
| BsrGI | 1 μl |
| HindIII | 2 μl |
| 10× Tangobuffer | 5 μl |
| $ddH_2O$ | 32 μl |
| Total | 50 μl |

Reaction conditions: 37° C. for 5 h.

When the reaction was concluded, 10 μl of the 6× loading buffer was added to the 50 μl reaction system to terminate the reaction. The fragment was isolated by agarose gel electrophoresis, recovered and purified using adsorption column. Detailed steps are described in "Shanghai Sangon Gel Purification Kits/DNA Recovery Kits".

For truncated mutations, digested fragment of $pRSET_b$-ydiH-YFP from proper mutant plasmid of $pRSET_b$-ydiH-YFP series was selected as desired, and then ligated with normal fragment of sequence YFP-ydiH without mutation. For site-directed mutagenesis, digested fragment of $pRSET_b$-ydiH-YFP from proper mutant plasmid of $pRSET_b$-ydiH-YFP series was selected as desired, and then ligated with digested fragment YFP-ydiH of $pRSET_b$-ydiH-YFP series containing site-directed mutation as well.

Ligation

Recovered and purified fragments $pRSET_b$-ydiH-YFP and YFP-ydiH were ligated using the following system:

| Ligation system | |
|---|---|
| Fragment YFP-ydiH | 4 |
| Fragment $pRSET_b$-ydiH-YFP | 1 |
| T4 DNA Ligase enzyme | 0.5 |
| 10× T4 DNA Ligase buffer | 1 |
| $ddH_2O$ | 3.5 |
| Total | 10 |

Reaction conditions: 16° C., overnight.

The ligation products were labeled to form $pRSET_b$-ydiH-YFP-ydiH Truc v2.xx or $pRSET_b$-ydiH-YFP-ydiH.

Identification of Plasmid Mutations

Colonies identified as positive in Colony PCR were selected and sequenced using universal primers at the Shanghai Branch of Beijing Liuhe BGI Technology Co., Ltd. The determined sequences were then compared and analyzed by Vector NTI 8.0.

Construction of Sensor Series

Following sensors were produced according to the methods described above.

| Plasmid | NO. | SEQ ID NO |
|---|---|---|
| $pRSET_b$-ydiH-YFP-ydiH(D2)C1 | C1 | 92 |
| $pRSET_b$-ydiH-YFP-ydiH(D2)C2 | C2 | 93 |
| $pRSET_b$-ydiH-YFP-ydiH(D2)C3 | C3 | 94 |
| $pRSET_b$-ydiH-YFP-ydiH(D2)C4 | C4 | 95 |
| $pRSET_b$-ydiH-YFP-ydiH(D2)C5 | C5 | 96 |
| $pRSET_b$-ydiH-YFP-ydiH(D2)C6 | C6 | 97 |
| $pRSET_b$-ydiH-YFP-ydiH(D2)C7 | C7 | 98 |
| $pRSET_b$-ydiH-YFP-ydiH(D2)C8 | C8 | 99 |
| $pRSET_b$-ydiH-YFP-ydiH(D2)C9 | C9 | 100 |
| $pRSET_b$-ydiH-YFP-ydiH(D2)Del T | Del T(1) | 101 |
| $pRSET_b$-ydiH-YFP-ydiH(D2)Del GT | Del GT | 102 |
| $pRSET_b$-ydiH-YFP-ydiH(D2)Del G | Del G | 103 |
| $pRSET_b$-ydiH-YFP-ydiH(D2)Del T | Del T(2) | 104 |
| $pRSET_b$-ydiH-YFP-ydiH(D2)C3 D118R | C3 D118R | 105 |
| $pRSET_b$-ydiH-YFP-ydiH(D2)C3 N120K | C3 N120K | 106 |
| $pRSET_b$-ydiH-YFP-ydiH(D2)C3 N120R | C3 N120R | 107 |
| $pRSET_b$-ydiH-YFP-ydiH(D2)C3 N120E | C3 N120E | 108 |
| $pRSET_b$-ydiH-YFP-ydiH(D2)C3 N120D | C3 N120D | 109 |
| $pRSET_b$-ydiH-YFP-ydiH(D2)C3 D193N | C3 D193N | 110 |
| $pRSET_b$-ydiH-YFP-ydiH(D2)C3 D193K | C3 D193K | 111 |
| $pRSET_b$-ydiH-YFP-ydiH(D2)C3 L194K | C3 L194K | 112 |
| $pRSET_b$-ydiH-YFP-ydiH(D2)C3 L194R | C3 L194R | 113 |
| $pRSET_b$-ydiH-YFP-ydiH(D2)C3 L194E | C3 L194E | 114 |
| $pRSET_b$-ydiH-YFP-ydiH(D2)C3 L194D | C3 L194D | 115 |
| $pRSET_b$-ydiH-YFP-ydiH(D2)C8 D118R | C8 D118R | 116 |
| $pRSET_b$-ydiH-YFP-ydiH(D2)C8 N120K | C8 N120K | 117 |
| $pRSET_b$-ydiH-YFP-ydiH(D2)C8 N120R | C8 N120R | 118 |
| $pRSET_b$-ydiH-YFP-ydiH(D2)C8 N120E | C8 N120E | 119 |
| $pRSET_b$-ydiH-YFP-ydiH(D2)C8 N120D | C8 N120D | 120 |
| $pRSET_b$-ydiH-YFP-ydiH(D2)C8 D193N | C8 D193N | 121 |
| $pRSET_b$-ydiH-YFP-ydiH(D2)C8 D193K | C8 D193K | 122 |
| $pRSET_b$-ydiH-YFP-ydiH(D2)C8 L194K | C8 L194K | 123 |
| $pRSET_b$-ydiH-YFP-ydiH(D2)C8 L194R | C8 L194R | 124 |
| $pRSET_b$-ydiH-YFP-ydiH(D2)C8 L194E | C8 L194E | 125 |

Example 4. Derivative Sensors of ydiH(189)-YFP-ydiH(190)

Principle for Sensor Construction

Derivative sensors were engineered using intermediate plasmid for constructing sensors such as $pRSET_b$-ydiH(189)-YFP-ydiH(190) as templates and following the principle of site-directed mutagenesis.

Truncated mutant sequences are shown below:

| Name | Structure | SEQ ID NO |
|---|---|---|
| Original sequence | F189-SAG-YFP-GGC-L190 | 127 |
| 189/190-N1 | F189-AG-YFP-GGC-L190 | 128 |
| 189/190-N2 | F189-G-YFP-GGC-L190 | 129 |
| 189/190-N3 | F189-YFP-GGC-L190 | 130 |
| 189/190-C1 | F189-SAG-YFP-GG-L190 | 131 |
| 189/190-C2 | F189-SAG-YFP-G-L190 | 132 |
| 189/190-C3 | F189-SAG-YFP-L190 | 133 |
| 189/190-C1N1 | F189-AG-YFP-GG-L190 | 134 |
| 189/190-C1N2 | F189-G-YFP-GG-L190 | 135 |
| 189/190-C1N3 | F189-YFP-GG-L190 | 136 |
| 189/190-C2N1 | F189-AG-YFP-G-L190 | 137 |
| 189/190-C2N2 | F189-G-YFP-G-L190 | 138 |
| 189/190-C2N3 | F189-YFP-G-L190 | 139 |
| 189/190-C3N1 | F189-AG-YFP-L190 | 140 |
| 189/190-C3N2 | F189-G-YFP-L190 | 141 |
| 189/190-C3N3 | F189-YFP-L190 | 142 |

Establishment of Mutant Library

1. Primer Design (Shanghai Sangon)

| SEQ ID No | Remark | Sequence(5'-3') |
|---|---|---|
| 68 | 189/190-N1 (F) | GCAGGCTACAACAGCGACAACGTC |
| 69 | 189/190-N1 (R) | GAAGTCCACGTTCTCCACGGCCAC |
| 70 | 189/190-N2 (F) | GGCTACAACAGCGACAACGTCTATATCATG |
| 71 | 189/190-N3 (F) | TACAACAGCGACAACGTCTATATCATGGC |
| 72 | 189/190-C1 (F) | CTGGCCGGCCTGACCCGGCTGAG |
| 73 | 189/190-C1 (R) | GGTACCGTTGTACTCCAGCTTGTGCCCCAGG |
| 74 | 189/190-C2 (R) | ACCGTTGTACTCCAGCTTGTGCCCCAGGATG |
| 75 | 189/190-C3 (R) | GTTGTACTCCAGCTTGTGCCCCAGGATGTTGC |
| 76 | Trex(D2) (F) | ATGAACCGGAAGTGGGGCCTG |
| 77 | Trex(D2) (R) | CGGATCCTTATCGTCATCGTCGTAC |
| 78 | D112SV113H (F) | CATGACCCCGAGAAGGTGGGC |
| 79 | D112SV113H (R) | CGAGAAGAAGCCCCGCAGCTC |

2. PCR Amplification

Truncated mutation and site-directed mutation were conducted using site-directed mutagenesis PCR.

Amplification system for PCR mutation (Primer, enzyme, dNTP and others purchased from Fermentas):

| PCR amplification system | |
|---|---|
| Template | 0.1 μl |
| Forward Primer | 0.5 μl |
| Reverse Primer | 0.5 μl |
| 5× PrimeStar Buffer | 10 μl |
| PrimeStar polymerase | 0.5 μl |
| dNTP mix (10 mM) | 4 μl |
| $ddH_2O$ | 33.5 μl |
| Total | 50 μl |

| PCR reaction conditions | | |
|---|---|---|
| | 98° C. | 5 min |
| 30 cycles | 98° C. | 10 sec |
| | 55° C. | 5 sec |
| | 72° C. | 4.5 min |
| | 72° C. | 10 min |

3. Separation, Purification of DNA Fragments

DpnI Digestion

The PCR amplified fragment was first treated with DpnI enzyme (from Fermentas) for 3 hours at 37° C. to remove the potential template plasmid contamination. The reaction system was then denatured and deactivated at 80° C. for 20 minutes. The deactivated mixture could be directly used for subsequent molecular biological experiments.

Phosphorylation of DNA Fragment

At the presence of ATP, the DNA fragment was treated with T4 polynucleotide kinase (T4 PNK) (from Fermentas) at 37° C. for 1 h to phosphorylate the 5'-OH of DNA ribose ring, in order to allow the fragment to cyclize by self-ligation. Then the reaction system was denatured and deactivated at 75° C. for 10 minutes. The deactivated mixture could be directly used for subsequent molecular biological experiments.

Ligation

The phosphorylated DNA fragments (mutated DNA fragments: $pRSET_b$-ydiH-YFP or $pRSET_b$-YFP-ydiH) were cyclized by self ligation overnight at 16° C. with T4 DNA ligase enzyme (from Fermentas).

Identification of Plasmid Mutations

Colonies identified as positive in Colony PCR were selected and sequenced using universal primers at the Shanghai Branch of Beijing Liuhe BGI Technology Co., Ltd. The determined sequence was then compared and analyzed by Vector NTI 8.0.

Construction of Sensor Series

Following sensors were produced according to the methods described above, and numbered respectively.

| Plasmid | NO. | SEQ ID NO |
|---|---|---|
| $pRSET_b$-ydiH(189)-YFP-ydiH(190) | F-rex2-1.0 | 127 |
| $pRSET_b$-ydiH(189)-YFP-ydiH(190)-N1 | F-rex2-2.0 | 128 |
| $pRSET_b$-ydiH(189)-YFP-ydiH(190)-N2 | F-rex2-2.1 | 129 |
| $pRSET_b$-ydiH(189)-YFP-ydiH(190)-N3 | F-rex2-2.2 | 130 |
| $pRSET_b$-ydiH(189)-YFP-ydiH(190)-C1 | F-rex2-2.3 | 131 |
| $pRSET_b$-ydiH(189)-YFP-ydiH(190)-C2 | F-rex2-2.4 | 132 |
| $pRSET_b$-ydiH(189)-YFP-ydiH(190)-C3 | F-rex2-2.5 | 133 |
| $pRSET_b$-ydiH(189)-YFP-ydiH(190)-C1N1 | F-rex2-2.6 | 134 |
| $pRSET_b$-ydiH(189)-YFP-ydiH(190)-C1N2 | F-rex2-2.7 | 135 |
| $pRSET_b$-ydiH(189)-YFP-ydiH(190)-C1N3 | F-rex2-2.8 | 136 |
| $pRSET_b$-ydiH(189)-YFP-ydiH(190)-C2N1 | F-rex2-2.9 | 137 |
| $pRSET_b$-ydiH(189)-YFP-ydiH(190)-C2N2 | F-rex2-2.10 | 138 |
| $pRSET_b$-ydiH(189)-YFP-ydiH(190)-C2N3 | F-rex2-2.11 | 139 |
| $pRSET_b$-ydiH(189)-YFP-ydiH(190)-C3N1 | F-rex2-2.12 | 140 |
| $pRSET_b$-ydiH(189)-YFP-ydiH(190)-C3N2 | F-rex2-2.13 | 141 |
| $pRSET_b$-ydiH(189)-YFP-ydiH(190)-C3N3 | F-rex2-2.14 | 142 |
| $pRSET_b$-Trex(D2)-ydiH(189)-YFP-ydiH(190) | F-rex2-2.15 | 143 |
| $pRSET_b$-Trex(D2)-ydiH(189)-YFP-ydiH(190)-N1 | F-rex2-2.16 | 144 |
| $pRSET_b$-Trex(D2)-ydiH(189)-YFP-ydiH(190)-N2 | F-rex2-2.17 | 145 |
| $pRSET_b$-Trex(D2)-ydiH(189)-YFP-ydiH(190)-N3 | F-rex2-2.18 | 146 |
| $pRSET_b$-Trex(D2)-ydiH(189)-YFP-ydiH(190)-C1 | F-rex2-2.19 | 147 |
| $pRSET_b$-Trex(D2)-ydiH(189)-YFP-ydiH(190)-C2 | F-rex2-2.20 | 148 |
| $pRSET_b$-Trex(D2)-ydiH(189)-YFP-ydiH(190)-C3 | F-rex2-2.21 | 149 |
| $pRSET_b$-Trex(D2)-ydiH(189)-YFP-ydiH(190)-C1N1 | F-rex2-2.22 | 150 |
| $pRSET_b$-Trex(D2)-ydiH(189)-YFP-ydiH(190)-C1N2 | F-rex2-2.23 | 151 |
| $pRSET_b$-Trex(D2)-ydiH(189)-YFP-ydiH(190)-C1N3 | F-rex2-2.24 | 152 |

-continued

| Plasmid | NO. | SEQ ID NO |
|---|---|---|
| pRSET$_b$-Trex(D2)-ydiH(189)-YFP-ydiH(190)-C2N1 | F-rex2-2.25 | 153 |
| pRSET$_b$-Trex(D2)-ydiH(189)-YFP-ydiH(190)-C2N2 | F-rex2-2.26 | 154 |
| pRSET$_b$-Trex(D2)-ydiH(189)-YFP-ydiH(190)-C2N3 | F-rex2-2.27 | 155 |
| pRSET$_b$-Trex(D2)-ydiH(189)-YFP-ydiH(190)-C3N1 | F-rex2-2.28 | 156 |
| pRSET$_b$-Trex(D2)-ydiH(189)-YFP-ydiH(190)-C3N2 | F-rex2-2.29 | 157 |
| pRSET$_b$-Trex(D2)-ydiH(189)-YFP-ydiH(190)-C3N3 | F-rex2-2.30 | 158 |

Example 5. Spectral Characteristics of Fluorescent Sensors for NADH

Figure 3A:
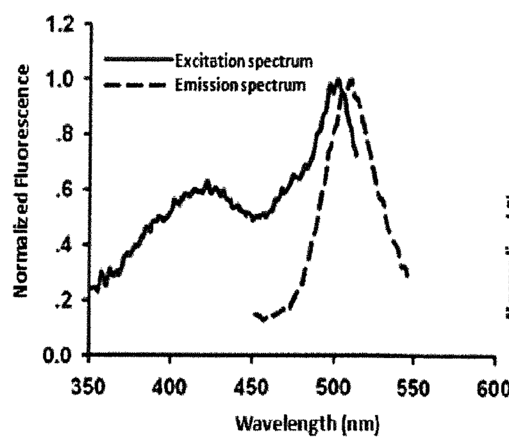
FIG. 3A shows absorption spectral characteristics of the nicotinamide adenine dinucleotide fluorescent sensor F-rex1.

The fluorescent sensors that prepared above were dissolved in assay buffer (100 mM KPi, pH7.4) to formulate fluorescent sensor solutions to a final concentration of 10 μM. Then their absorption spectra were measured using a Multi-functional Fluorescence Microplate Reader (Synergy2, Biotek) (FIG. 3A).

Figure 3B:
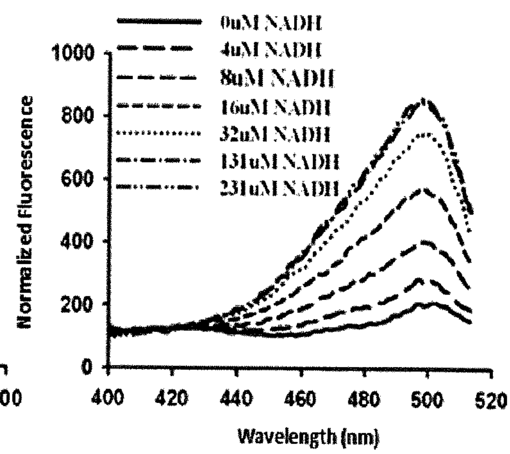
FIG. 3B shows excitation and emission spectral characteristics of the nicotinamide adenine dinucleotide fluorescent sensor F-rex1.

Their excitation and emission spectra were determined using a fluorescence spectrophotometer (Cary Eclipse Fluorescence spectrophotometer, Varian) (FIG. 3B).

Figure 4:
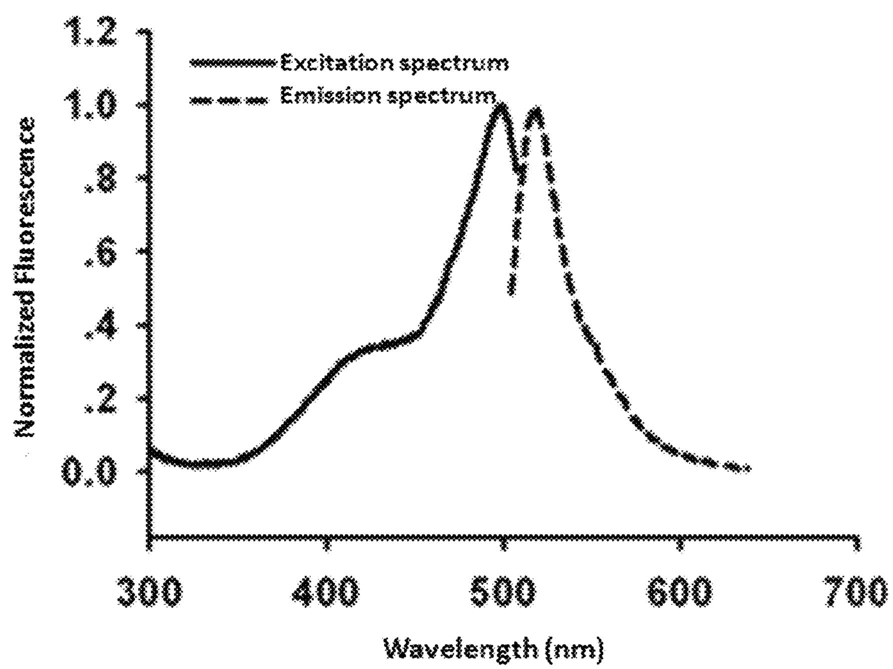
FIG. 4 shows basic spectral characteristics of the nicotinamide adenine dinucleotide fluorescent sensor F-rex2.

Experimental results indicated that, F-rex1 had two excitation peaks at 400 nm and 490 nm, respectively, and the latter exhibited an intensity five times of that of the former. However, F-rex1 had only one emission peak at 521 nm. Meanwhile, F-rex2 protein has two excitation peaks at 410 nm and 500 nm, respectively, and the latter exhibited an intensity about half of that of the former. However, F-rex2 had only one emission peak at 518 nm (FIG. 4).

Example 6. Characteristics of Fluorescent Sensors for NADH in Responses to Pyridine Nucleotide Analogs Under Physiological Conditions The fluorescent sensors prepared above were dissolved in assay buffer (100 mM KPi, pH7.4) to formulate protein solutions to a final concentration of 1 μM. Pyridine nucleotide analogs $NAD^+$, NADH, ATP, ADP, $NADP^+$ and NADPH (Merck Biosciences GmbH, Darmstadt, Germany) were prepared in assay buffer (100 mM KPi, pH7.4) for stock solutions at a final concentration of 8 mM, which were diluted to 80 μM before use.

Two hundred microliter of the 1 μM solution of fluorescent sensors was taken, and first titrated 5× with 4 μl of the 80 μM $NAD^+$ or NADH or ATP or ADP or $NADP^+$ or NADPH, then further titrated 5× with 4 μl of the 8 mM $NAD^+$ or NADH or ATP or ADP or $NADP^+$ or NADPH. After each titration, the solution was vortexed 5 seconds to allow the reaction to complete, then the fluorescent intensity of 528 nm emission upon 485 nm excitation was measured using a Multi-functional Fluorescence Microplate Reader (Synergy2, Biotek).

Figure 5:
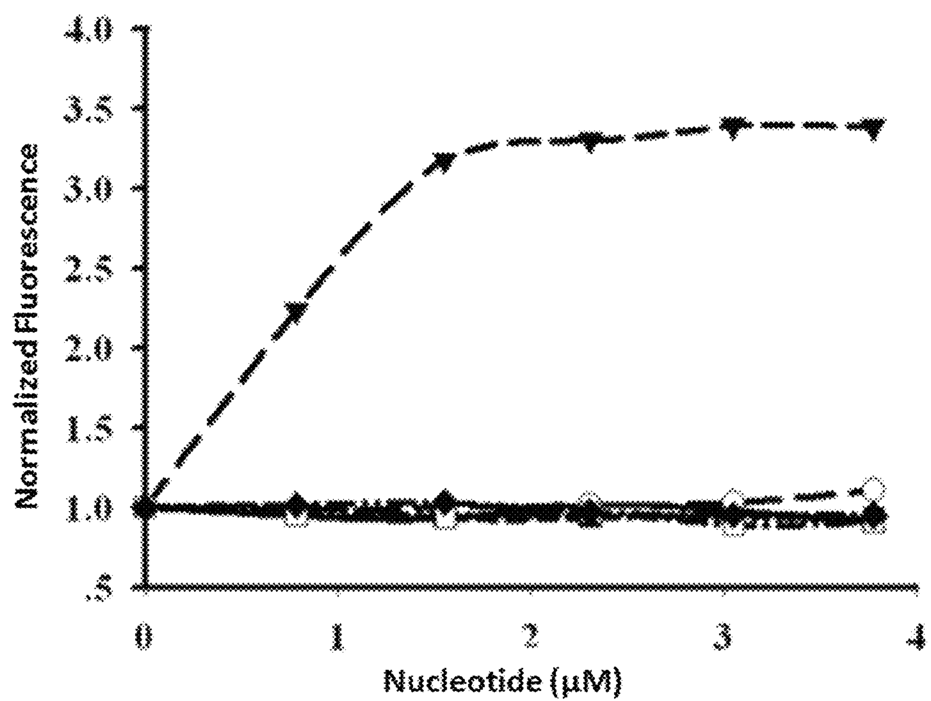
FIG. 5 shows response of fluorescent sensor F-rex1 for reduced nicotinamide adenine dinucleotide to pyridine nucleotide analogs under simulated physiological conditions in vitro.
Figure 6:
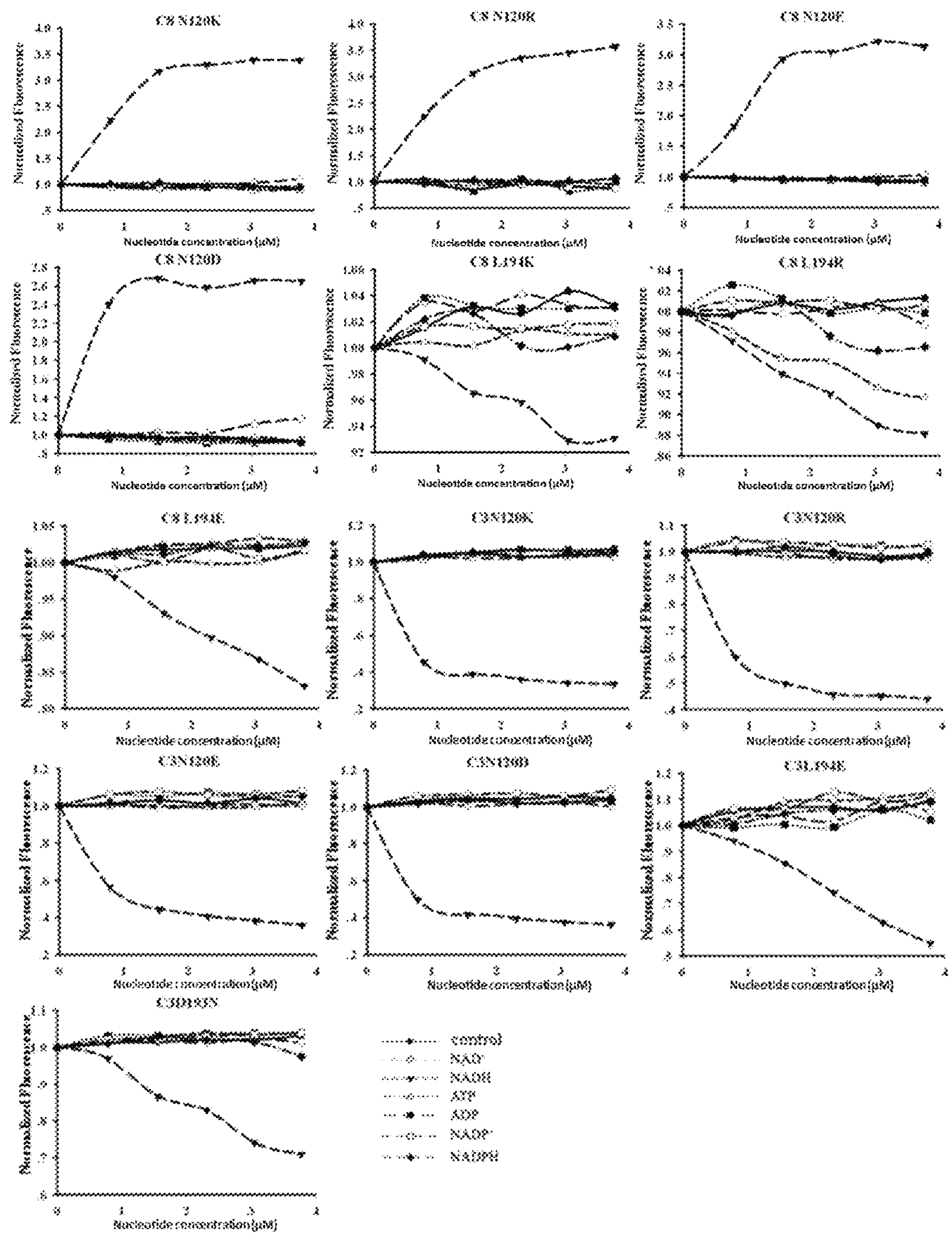
FIG. 6 shows response of the derivatized fluorescent sensor for reduced nicotinamide adenine dinucleotide to pyridine nucleotide analogs under simulated physiological conditions in vitro.

Measurements demonstrated that, NADH fluorescent sensors exhibited robust response to NADH at the physiological concentration (<100 μM NADH), but no notable response to other pyridine nucleotide was observed (FIGS. 5 and 6).

Example 7. Localization and Expression of Fluorescent Sensor for NADH in Different Subcellular Organelles The NADH fluorescence sensor gene (Frex) was obtained using pRSET$_b$-ydiH-cpYFP-ydiH(D2) as template, and double-digesting it with BamHI and HindIII. The digested fragment was recovered and ligated to the following vectors: pcDNA3.1-Hygro-Cyto, pcDNA3.1-Hygro-Mito, pcDNA3.1-Hygro-Nuc, pcDNA3.1-Hygro-Mem, pcDNA3.1-Hygro-Golgi, pcDNA3.1-Hygro-ER and pcDNA3.1-Hygro-Peroxi respectively (engineered in Protein Chemistry Laboratory of East China University of Science and Technology, Shanghai, China).

Preparation: unless otherwise indicated, all primers used herein were synthesized by Shanghai Sangon (Sangon Biotech (Shanghai Co. Ltd., Shanghai, China). First, vector pcDNA3.1-Hygro-Cyto was constructed based on pcDNA3.1-Hygro (+) (Invitrogen, California, U.S.A.). Two primers: Cyto Forward Primer and Cyto Reverse Primer, were designed.

```
Cyto Forward Primer:
                                  (SEQ ID No 80)
CTAGCATGGCGGATCCACTAGTAAGCTTAAGC

Cyto Reverse Primer:
                                  (SEQ ID No 81)
TCGAGCTTAAGCTTACTAGTGGATCCGCCATG
```

This primer pair contains restriction sites and the start codon ATG, and the structure was "NheI-ATG-GC-BamHI-HindIII-XhoI". Following steps for dual primer annealing with the obtained primers was carried out.

1. The primer powder was dissolved to 100 μM in specific buffer (10 mM Tris, pH7.5-8.0; 50 mM NaCl, 1 mM EDTA).
2. Equimolar amounts of the primer pair to be annealed were mixed to a total volume of no greater than 500 μl.
3. The mixture was heated to 95° C. and then slowly cooled to room temperature (below 30° C.), then stored at −20° C. before use.

For organelle targeting signal Mito (SEQ ID No 82) and Golgi (SEQ ID No 83), the signal was introduced into vector pcDNA3.1-Hygro(+) through double-digestion utilizing synthesized targeting signal containing NheI restriction site allocated at 5' end and BamHI restriction site allocated at 3' end.

| Double-digestion system | |
|---|---|
| DNA fragment | 10 μl |
| NheI | 1 μl |
| BamHI | 1 μl |
| 10× Tangobuffer | 5 μl |
| $ddH_2O$ | 33 μl |
| Total | 50 μl |

| Double-digestion system | |
|---|---|
| Vector:pcDNA3.1-Hygro(+) | 10 μl |
| NheI | 1 μl |
| BamHI | 1 μl |
| 10× Tangobuffer | 5 μl |
| $ddH_2O$ | 33 μl |
| Total | 50 μl |

Similarly, for organelle targeting signal Nuc, Mem, E R and Peroxi, a pair of restriction sites were allocated to their both ends, respectively. Synthesized primers were utilized in dual primer annealing for the formation of double-stranded DNA, double-stranded DNA fragment with sticky ends obtained directly thereby was subsequently ligated with double-digested vector pcDNA3.1-Hygro(+).

Nuc Forward Primer:
(SEQ ID No 84)
*AGCTT*GATCCAAAAAAGAAGAGAAAGGTAGATCCAAAAAAGAAGAGAA

AGGTAGATCCAAAAAAGAAGAGAAAGGTAG*C*

Nuc Reverse Primer:
(SEQ ID No 85)
*TCGAG*CTACCTTTCTCTTCTTTTTTGGATCTACCTTTCTCTTCTTTTTTG

GATCTACCTTTCTCTTCTTTTTTGGATC*A*

Mem Forward Primer:
(SEQ ID No 86)
*CTAGC*ATGGCGCTGTGCTGTATGAGAAGAACCAAACAGGTTGAAAAGAA

TGATGAGGACCAAAAGATCGC*G*

Mem Reverse Primer:
(SEQ ID No 87)
*GATCC*GCGATCTTTTGGTCCTCATCATTCTTTTCAACCTGTTTGGTTCTT

CTCATACAGCACAGCGCCAT*G*

ER Forward Primer:
(SEQ ID No 88)
*CTAGC*ATGGCGCTGCTATCCGTGCCGTTGCTGCTCGGCCTCCTCGGCCTG

GCCGTCGCCGC*G*

ER Reverse Primer:
(SEQ ID No 89)
*GATCC*GCGGCGACGGCCAGGCCGAGGAGGCCGAGCAGCAACGGCAC

GGATAGCAGCGCCAT*G*

Peroxi Forward Primer:
(SEQ ID No 90)
*AGCTT*TCCAAGCTGTAA*C*

Peroxi Reverse Primer:
(SEQ ID No 91)
*TCGAG*TTACAGCTTGGA*A*

Recombinant plasmids pcDNA3.1-Hygro-Cyto-Frex, pcDNA3.1-Hygro-mito-Frex, pcDNA3.1-Hygro-Frex-Nuc, pcDNA3.1-Hygro-mem-Frex, pcDNA3.1-Hygro-golgi-Frex, pcDNA3.1-Hygro-Frex-ER and pcDNA3.1-Hygro-Frex-peroxi were constructed, and then sequenced. The results demonstrated that the nucleotide sequences of Frex fragment were the same as SEQ ID NO: 9. HEK293 cells, HEK293FT cells and Cos7 cells were transfected with these recombinant plasmids, respectively. The transfected cells were observed under a laser scanning confocal microscope (Nikon, Japan) with two excitation wavelengths at 405 nm and 488 nm, while the emission wavelength was 500-550 nm.

Experimental results indicated that, in HEK293FT cells, Frex-Cyto was efficiently and accurately located in the cytoplasm (FIG. 7A); Frex-Mito was efficiently and accurately located in the mitochondria (FIG. 7B); Frex-Nuc was efficiently and accurately located in the nucleus (FIG. 7C); Frex-Mem was efficiently and accurately located in the membrane (FIG. 7D); Frex-Golgi was efficiently and accurately located in the Glogi (FIG. 7E); Frex-ER was efficiently and accurately located in the endoplasmic reticulum (FIG. 7F); Frex-Pero was efficiently and accurately located in the peroxisomes (FIG. 7G).

Example 8 Utilizing the Sensor Series to Indicate Changes of Intracellular Reduced Nicotinamide Adenine Dinucleotide (1) Fluorescent sensors for reduced nicotinamide adenine dinucleotide used in real-time measurements of increases of NADH levels in different subcellular compartments as the result of trans-membrane entrance of NADH into the cell.

As described in Example 7, the fluorescence sensors for reduced nicotinamide adenine dinucleotide were expressed in different subcellular organelles of 293FT cells. Results showed that this series of sensors are capable of detecting, in real time, the changes in intracellular NADH levels upon the addition of external NADH in cell culture medium (FIG. 8-1A). Following the addition of external NADH into cell culture medium, transfected cells were observed under a laser scanning confocal microscope (Nikon, Japan). The results indicated that, the emission fluorescence at 528 nm upon 485 nm excitation of the sensor was 2.5 times stronger than that of the control group, proving NADH could enter cells across the membrane and lead to the immediate increase of intracellular NADH levels; FIG. 8-1D and FIG. 8-1E showed that the fluorescence sensor for reduced nicotinamide adenine dinucleotide was not interfered by NADH analogs such as $NAD^+$, NADPH, etc. As to the control group in comparison, the cpYFP presented alone was not affected by extra NADH either. Therefore, effects of pH and the variation in cpYFP per se by environmental changes could be excluded. This series of sensors were further utilized to detect influences of extra NADH on other organelles, and observed that extra NADH could also increase the NADH levels in nucleus and mitochondria, the results for nucleus study are shown in FIG. 8-1B, and those for mitochondria study are shown in FIG. 8-1C. In conclusion, our results indicated that fluorescent sensors for nicotinamide adenine dinucleotide could serve as a good gauge for the increase of NADH levels in mammalian cells upon the transmembrane entrance of NADH.

(2) Fluorescent sensor for nicotinamide adenine dinucleotide used in real-time measurements of NADH levels in different subcellular compartments regulated by glucose, pyruvate and lactate.

Glycolysis is an important pathway of producing NADH and it plays a vital role in regulating intracellular NADH levels. The nicotinamide adenine dinucleotide fluorescent sensors were used to test how several important metabolites in this pathway, glucose, pyruvate and lactate, would influence the NADH levels in different subcellular compartments. FIG. 8-2A shows results within cytoplasm and FIG. 8-2D shows results within mitochondria. These results indicated that, as one source of cellular energy, glucose could lead to the increase the cytoplasmic and mitochondrial levels of NADH. As products of glycolysis pathway, pyruvate and lactate are presented in the cytoplasm with a dynamic balance between them. At increased intracellular levels of pyruvate, lactate dehydrogenase consumes NADH and produces lactate and $NAD^+$, and in turn, leads to the decrease of NADH levels in cytoplasm. At increased intracellular levels of lactate, lactate dehydrogenase consumes $NAD^+$ and produces pyruvate and NADH, and in turn, leads to the increase of NADH levels in cytoplasm. FIG. 8-2B shows that pyruvate could cause a rapid decline of NADH levels in cytoplasm, but it resumed to normal levels over time. FIG. 8-2C shows that lactate could cause a rapid increase of NADH levels in cytoplasm, but also resumed to normal levels over time. In conclusion, these results demonstrated that the fluorescence sensors for nicotinamide adenine dinucleotide could monitor, in real-time, the regulated dynamic balance of NADH levels in cytoplasm.

(3) Fluorescent sensors for reduced nicotinamide adenine dinucleotide used in real-time detection of NADH levels in mitochondria regulated by oxidative phosphorylation pathway.

NADH that produced via glycolysis pathway and tricarboxylic acid cycle pathway will be oxidized by the oxidative phosphorylation pathway of mitochondrial respiratory chain, and then generate ATP to provide energy for various life activities. Fluorescent sensors for nicotinamide adenine dinucleotide were used to measure changes of NADH levels in mitochondria when various complexes in the respiratory chain were inhibited. FIG. 8-3A shows a 6-minute dynamic profile of the NADH sensor, which was expressed in mitochondria, upon 3-NP treatment. FIG. 8-3B shows a 6-minute dynamic profile of the control protein cpYFP, which was expressed in mitochondria, upon 3-NP treatment. Time interval between the figures was 1 min. The cells were observed before and after treatment under a laser scanning confocal microscope (Nikon, Japan). Results showed that, complex II inhibitor 3-NP caused a greatly decline of NADH levels in mitochondrial because of inhibited TCA cycle, whereas in the control group, cpYFP showed no obvious change. FIG. 8-3C shows the measurement of the effect of other complex inhibitors on NADH levels in mitochondria using fluorescent sensor for nicotinamide adenine dinucleotide. Results showed that, upon treated with complex I inhibitor rotenone, complex III inhibitor antimycin A, and complex IV inhibitor NaCN, respectively, for 30 min, the fluorescence (ex 485, em 528) of the sensor was increased, indicating that these inhibitors prevented the oxidation of NADH by inhibiting oxidative phosphorylation pathway, thus, led to the increase of NADH levels in mitochondria (FIG. 8-3C).

Figures 1, 9:
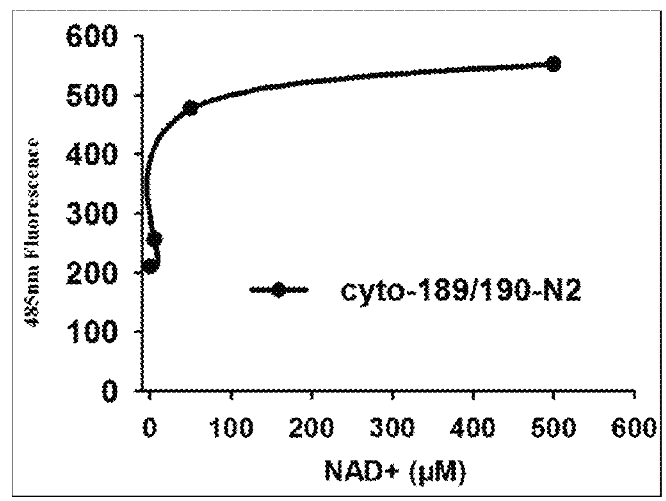
Figures 2, 9:
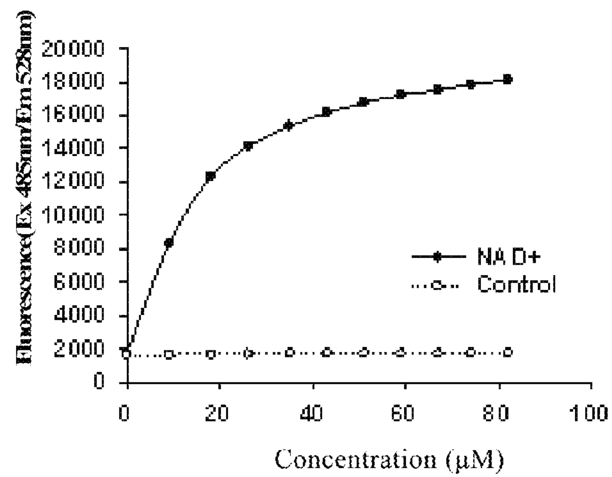

Example 9 Measurement of Changes in Intracellular $NAD^+$ Level by Fluorescent Sensors for Oxidized Nicotinamide Adenine Dinucleotide Fluorescent sensor for oxidized nicotinamideadenine dinucleotide has a structure with cpYFP inserted into Trex between two amino acids, F189 and L190. The sequence of said sensor is SEQ ID NO: 129. Said sensor was prepared as described in Example 4. By expressing said sensors in cytoplasm of 293FT cells, we found that real-time monitor of the effects on intracellular $NAD^+$ levels of adding $NAD^+$ into cell culture medium could be well achieved using this series of sensors (FIG. 9-1). As shown in FIG. 9-1, upon the addition of external $NAD^+$ into cell culture medium, the fluorescence of 528 nm emission upon 485 nm excitation was rapidly enhanced by about 2.8 times, proving that fluorescence sensor for oxidized nicotinamide adenine dinucleotide is a good gauge for the increase of $NAD^+$ levels in mammalian cells upon the transmembrane entrance of $NAD^+$. In protein detection with single channel 485 nm excitation and 528 nm emission, Frex-2 sensors responded to $NAD^+$ by about 1000% (FIG. 9-2), while they exhibited no response to NADP, NADPH, ADP and ATP (FIG. 9-3).

Figures 1, 10:
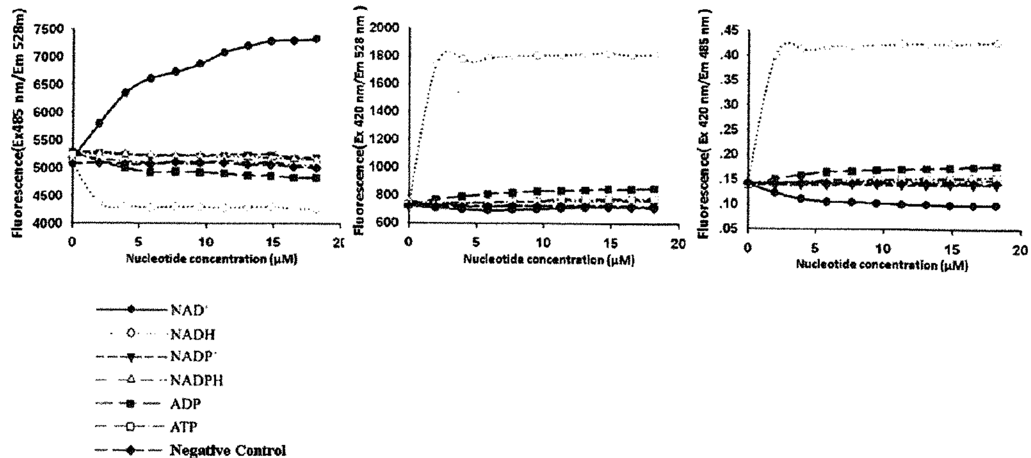
Figures 2, 10:
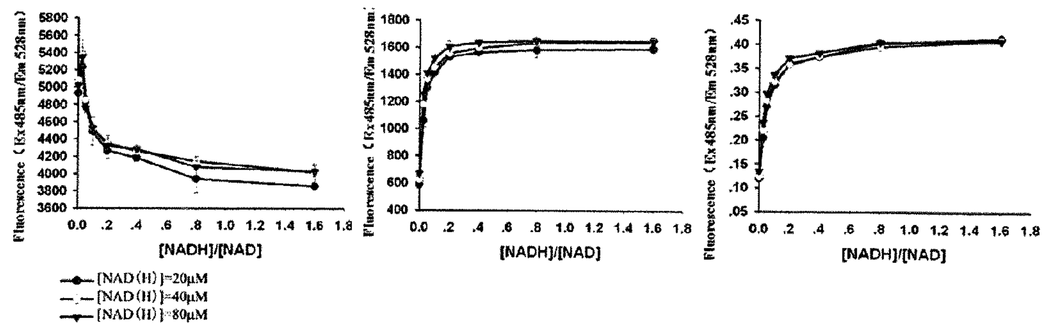
Figures 3, 10:
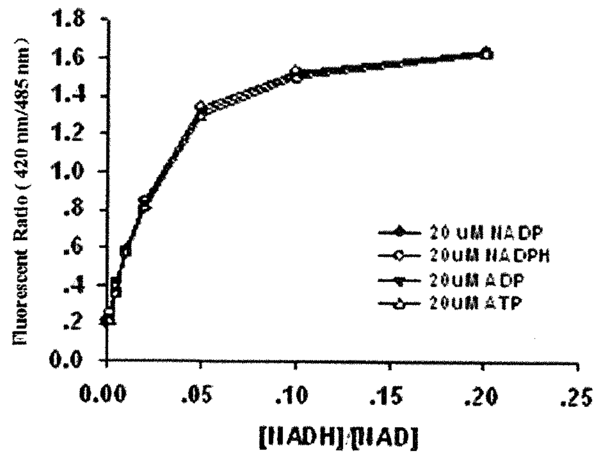

Example 10 Measurement of Changes in NADH/$NAD^+$ Ratio by Fluorescent Sensors for Reduced/Oxidized Nicotinamide Adenine Dinucleotide Ratio Fluorescent sensor for reduced/oxidized nicotinamide adenine dinucleotide ratio has a structure with cpYFP inserted into Trex between two amino acids, F189 and L190. The sequence of said sensor is SEQ ID NO: 148. Said sensor was prepared as described in Example 4. Said sensor exhibited response only to NADH and $NAD^+$, but no response to NADH analogs. Upon 485 nm excitation, binding with NADH and $NAD^+$ could both lead increased fluorescence emission at 528 nm. However, upon 420 nm excitation, said sensor could only respond to NADH binding. Since 420 nm and 485 nm excitation could both produce emission fluorescence at 528 nm, different excitation wavelengths could be used to measure the ratio of fluorescence intensity emitted at 528 nm (420 nm/485 nm), it has been found that NADH binding increases the response in said fluorescence ratio, while $NAD^+$ binding decreases the response in said fluorescence ratio (FIG. 10-1). This pattern is more evident when the total concentration of NADH and $NAD^+$ remained unchanged, but would not change with the total concentration per se (FIG. 10-2).

Figures 3, 9:
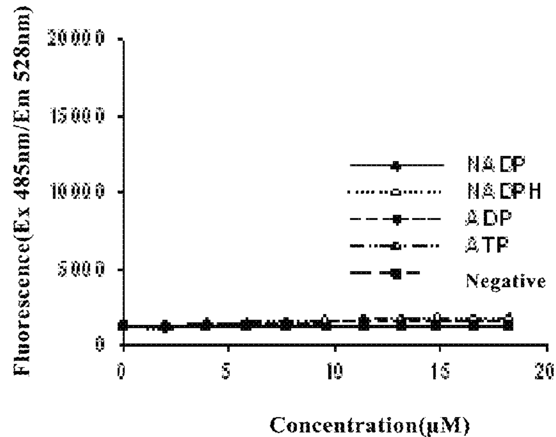

At the presence of 20 uM NADP, NADPH, ADP and ATP, titration of [NADH]/[$NAD^+$] at indicated ratio was conducted, we could find the responsive value and variation pattern were not affected, indicating that NADP, NADPH, ADP and ATP have no effect on the sensor (FIG. 10-3).

Therefore, said sensor could be used not only as a sensor for reduced/oxidized nicotinamide adenine dinucleotide ratio but also a sensor for reduced nicotinamide adenine dinucleotide alone.

Example 11 High-Throughput Drug Screening Based on Fluorescence Sensor for Reduced/Oxidized Nicotinamide Adenine Dinucleotide Ratio It is generally believed that there is a dynamic balance between the concentration of pyruvate and lactate in cytoplasm and the concentration of free NADH and $NAD^+$ in cytoplasm. In healthy tissues, pyruvate produced by glycolysis mainly enters mitochondria to participate TCA cycle and eventually generates a large amount of energy through oxidative phosphorylation. But in malignant tissues, pyruvate is mainly reduced to lactate by lactate dehydrogenase, accompanied by oxidizing NADH to $NAD^+$. We developed a new method of high-throughput drug screening based the metabolic variation using superFrex, a fluorescent sensor for reduced/oxidized nicotinamide adenine dinucleotide ratio.

Figure 11A:
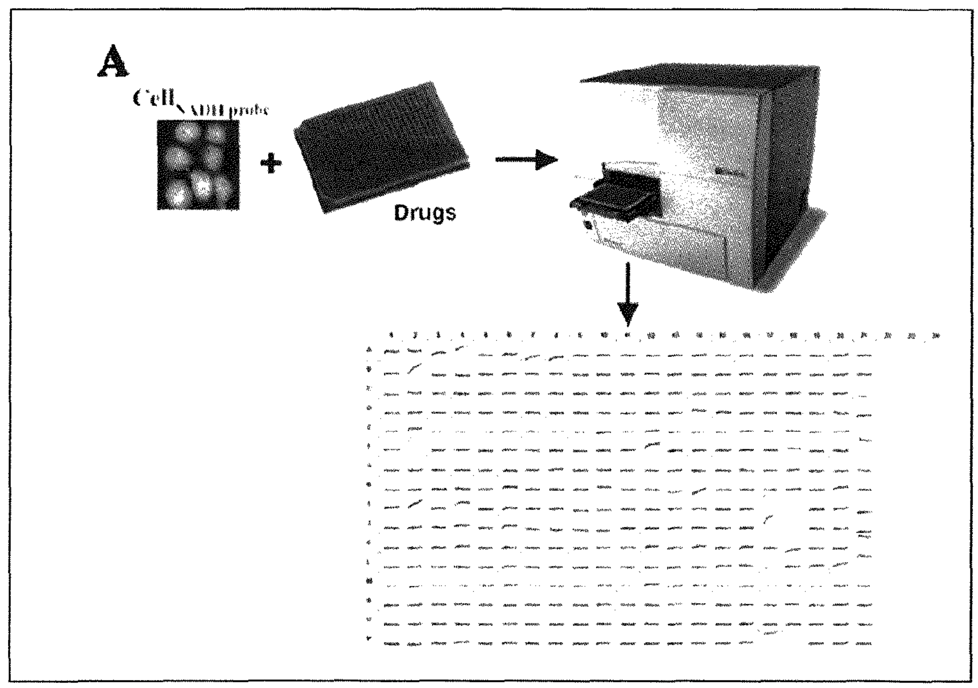
FIG. 11A shows a high-throughput drug screening scheme based on the sensor for NADH/NAD$^+$ ratio fluorescence.
Figure 11B:
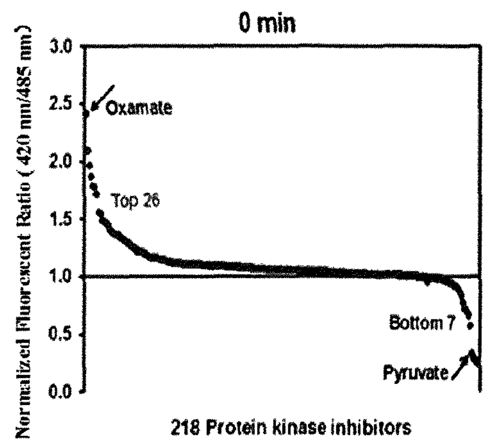
FIG. 11B shows results from high-throughput drug screening scheme using the sensor for NADH/NAD$^+$ ratio fluorescence identifying compounds increasing or reducing the ratio of intracellular lactate/pyruvate at time 0 min.
Figure 11C:
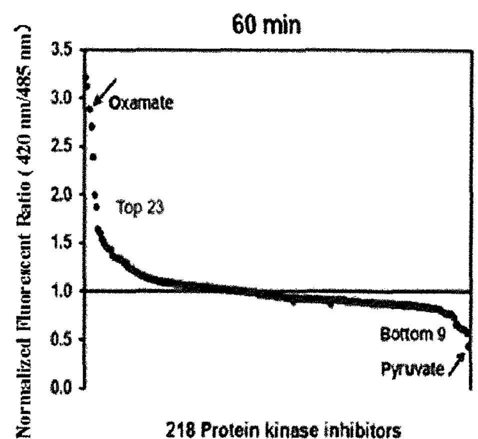
FIG. 11C shows a high-throughput drug screening scheme based on the sensor for NADH/NAD$^+$ ratio fluorescence identifying compounds increasing or reducing the ratio of intracellular lactate/pyruvate at time 60 min.

Stable cell lines expressing superFrex were mixed with different agents, then loaded into a black 384-well plate, and the fluorescence of superFrex was measured with a Multifunctional Microplate Reader (FIG. 11-A). For instance, from Merck's Protein kinase inhibitor compound library, we discovered 23-26 compounds increasing the ratio of intracellular lactate/pyruvate, and 7-9 compounds reducing the ratio of intracellular lactate/pyruvate (FIG. 11-B, 11-C). By further analyzing these compounds for the effect on the proliferation of normal cells and tumor cells, several lead compounds were eventually identified. These lead compounds could, at a certain dose range, effectively kill tumor cells but exhibited no toxicity to normal cells, therefore, has the potential to be developed as anticancer drugs.

Example 12 Measurement of NADH Metabolism in Tumor Cells Using Fluorescent Sensor for Reduced/Oxidized Nicotinamide Adenine Dinucleotide Ratio H1299 tumor cells were transfected with pcDNA3.1-cyt-superFrex, and then screened under Hygromycin B for 2 weeks. Single clones of H1299 stable cell lines that exhibiting robuse expression of superFrex were obtained by flow cytometry sorting (H1299-superFrex). Male nude mice of 5-6 weeks old were subcutaneously injected with 200 μl of H1299-superFrex cell suspension ($1.0\times10^7$ cells) into their right armpits and housed for 3-4 weeks at SPF Animal facility, tumors in the nude mice grew to 0.6-1.0 cm. The nude mice were anaesthetized and then injected with 300 μl of sodium pyruvate (100 mM) via the tail vein. Effects of the agent on tumor metabolism were observed immediately with Kodak multifunctional vivo imaging system (Carestream, USA). Experimental results showed that, pyruvate resulted a quick decrease in the fluorescence of 420 nm channel of superFrex in tumor tissues, and a quick increase in the fluorescence of 490 nm channel of superFrex, leading to a decrease in ratio 420/490 nm (FIG. 12-A). As the experimental control, tumor cells expressing cpYFP exhibited no difference caused thereby (FIG. 12-B), indicating pyruvate caused the decrease of $NADH/NAD^+$ ratios in tumor cells. Over time, pyruvate was gradually consumed metabolically, and the ratio of $NADH/NAD^+$ in tumor cells resumed the initial level (FIG. 12-C). In summary, superFrex, the fluorescent sensor for reduced/oxidized nicotinamide adenine dinucleotide ratio, works well in real-time monitoring of the NADH metabolism in tumor tissues.

OTHER EMBODIMENTS

A number of embodiments are described herein. However, it should be understood that, in view of this specification, variations and modifications will be apparent to those skilled in the art, without departing from the spirit and scope of the invention. Therefore, these alternative embodiments are also included within the scope of the appended claims.

The invention claimed is:

1. A genetically encoded fluorescent sensor for $NAD^+$, comprising a polypeptide sensitive to environmental $NAD^+$, and a segment that exhibits the environmental $NAD^+$ by change in its spectral characteristics, wherein the polypeptide sensitive to $NAD^+$ is:

(1) a polypeptide derived from ydiH, a bacterial transcription factor Rex protein, wherein the polypeptide is encoded by a sequence selected from SEQ ID NO: 1-3;

(2) a homologous or non-homologous sequence that is 95% identical to any of SEQ ID NO: 1-3; or (3) a homologous or non-homologous sequence that is 90% identical to any of SEQ ID NO: 1-3;

a $NAD^+$ binding fragment or $NAD^+$ binding domain thereof; and wherein the segment that exhibits the environmental $NAD^+$ by change in the spectral characteristic is a fluorescent protein sequence or a derivative thereof and is inserted between residue 189 and residue 190 of the polypeptide encoded by SEQ ID NO: 1, 2, or 3.

2. The fluorescent sensor according to claim 1, wherein the fluorescent sensor comprises:

(1) an amino acid sequence selected from the group consisting of SEQ ID NO: 127-158;

(2) a homologous or non-homologous sequence that is 95% identical to any of SEQ ID NO: 127-158; or (3) a homologous or non-homologous sequence that is 90% identical to any of SEQ ID NO: 127-158.

3. The fluorescent sensor according to claim 1, wherein the fluorescent sensor further comprises specific subcellular localization signal, wherein the localization signal allows localization of a target protein into a specified subcellular organelle.

4. A nucleic acid sequence encoding the fluorescent sensor according to claim 1.

5. A method of detecting $NAD^+$ or $NADH/NAD^+$, measuring $NAD^+$ or $NADH/NAD^+$ metabolism, drug screening or disease diagnosis, comprising contacting a sample with the fluorescent sensor according to claim 1;

measuring fluorescence of the fluorescent sensor.

6. The method according to claim 5, wherein the screening involves cells capable of expressing the fluorescent sensor according to claim 1, and active compounds are those capable of changing the ratio of lactate/pyruvate.

7. The method according to claim 6, wherein the screening takes a compound library of enzyme inhibitors or agonists as a pool of candidate agents.

8. The method according to claim 5, which is carried out in a mammalian system.

9. The method according to claim 8, wherein the system is a tumor bearing mammalian system.

10. A kit comprising the fluorescent sensor according to claim 1.

11. A genetically encoded fluorescent sensor for reduced/oxidized nicotinamide adenine dinucleotide ratio ($NADH/NAD^+$), comprising a polypeptide sensitive to environmental $NADH/NAD^+$, and a segment that exhibits the environmental $NADH/NAD^+$ by change in its spectral characteristics, wherein the polypeptide sensitive to $NADH/NAD^+$ is:

(1) a polypeptide derived from ydiH, a bacterial transcription factor Rex protein, wherein the polypeptide comprises amino acids 78-211 encoded by any one of SEQ ID NO: 1, 2 or 3;

(2) a homologous or non-homologous sequence that is 95% identical to any one of the polypeptides of (1); or (3) a homologous or non-homologous sequence that is 90% identical to any one of the polypeptides of (1);

a $NADH/NAD^+$ binding fragment or $NADH/NAD^+$ binding domain thereof; and wherein the segment that exhibits the environmental $NADH/NAD^+$ by change in the spectral characteristic is a fluorescent protein sequence or a derivative thereof and is inserted between residue 189 and residue 190 of said polypeptide sensitive to $NADH/NAD^+$.

12. The fluorescent sensor according to claim 11, wherein the fluorescent sensor comprises:

(1) an amino acid sequence selected from the group consisting of SEQ ID NO: 127-158;

(2) a homologous or non-homologous sequence that is 95% identical to any of SEQ ID NO: 127-158; or (3) a homologous or non-homologous sequence that is 90% identical to any of SEQ ID NO: 127-158.

13. The fluorescent sensor according to claim 11, wherein the fluorescent sensor further comprises specific subcellular localization signal, wherein the localization signal allows localization of a target protein into a specified subcellular organelle.

14. A nucleic acid sequence encoding the fluorescent sensor according to claim 11.

15. A method of detecting $NAD^+$ or $NADH/NAD^+$, measuring $NAD^+$ or $NADH/NAD^+$ metabolism, drug screening or disease diagnosis, comprising contacting a sample with the fluorescent sensor according to claim 11;

measuring fluorescence of the fluorescent sensor.

16. The method according to claim 15, wherein the screening involves cells capable of expressing the fluorescent sensor according to claim 11, and active compounds are those capable of changing the ratio of lactate/pyruvate.

17. The method according to claim 16, wherein the screening takes a compound library of enzyme inhibitors or agonists as a pool of candidate agents.

18. The method according to claim 15, which is carried out in a mammalian system.

19. The method according to claim 18, wherein the system is a tumor bearing mammalian system.

20. A kit comprising the fluorescent sensor according to claim 11.

21. A genetically encoded fluorescent sensor for reduced/oxidized nicotinamide adenine dinucleotide ratio (NADH/$NAD^+$), comprising a polypeptide sensitive to environmental NADH/$NAD^+$, and a segment that exhibits the environmental NADH/$NAD^+$ by change in its spectral characteristics, wherein the polypeptide sensitive to NADH/$NAD^+$ is:

(1) a polypeptide derived from ydiH, a bacterial transcription factor Rex protein, wherein the polypeptide comprises amino acids 78-211 encoded by SEQ ID NO: 1, 2 or 3;

(2) a homologous or non-homologous sequence that is 95% identical to amino acids 78-211 encoded by SEQ ID NO: 1, 2 or 3 of (1); or (3) a homologous or non-homologous sequence that is 90% identical to amino acids 78-211 encoded by SEQ ID NO: 1, 2 or 3 of (1);

a NADH/$NAD^+$ binding fragment or NADH/$NAD^+$ binding domain thereof; and wherein the segment that exhibits the environmental NADH/$NAD^+$ by change in the spectral characteristic is a fluorescent protein sequence or a derivative thereof and is inserted between residue 189 and residue 190 of the polypeptide comprising amino acids 78-211 encoded by SEQ ID NO: 1, 2 or 3.

* * * * *